United States Patent
McKenna et al.

(10) Patent No.: US 10,918,647 B2
(45) Date of Patent: Feb. 16, 2021

(54) SELECTIVE BROMODOMAIN INHIBITION OF FUNGAL BDF1

(71) Applicants: University of Southern California, Los Angeles, CA (US); CNRS, Paris (FR); Universite Grenoble Alpes, Saint Martin d'Heres (FR); INSERM, Paris (FR)

(72) Inventors: Charles E. McKenna, Los Angeles, CA (US); Carlo Petosa, Paris (FR); Jerome Govin, Paris (FR); Boris A. Kashemirov, Los Angeles, CA (US); Elena Ferri, Los Angeles, CA (US); Flore Mietton, Saint Martin d'Heres (FR)

(73) Assignees: University of Southern California, Los Angeles, CA (US); CNRS, Paris (FR); Universite Grenoble Alpes, Saint Martin d'Heres (FR); INSERM, Paris (FR)

( * ) Notice: Subject to any disclaimer, the term of this patent is extended or adjusted under 35 U.S.C. 154(b) by 0 days.

(21) Appl. No.: 16/320,412

(22) PCT Filed: Jul. 26, 2017

(86) PCT No.: PCT/US2017/044026
§ 371 (c)(1),
(2) Date: Jan. 24, 2019

(87) PCT Pub. No.: WO2018/022802
PCT Pub. Date: Feb. 1, 2018

(65) Prior Publication Data
US 2019/0240232 A1   Aug. 8, 2019

Related U.S. Application Data

(60) Provisional application No. 62/366,973, filed on Jul. 26, 2016.

(51) Int. Cl.
```
C07D 281/14    (2006.01)
C07D 281/16    (2006.01)
A61K 31/554    (2006.01)
A61K 45/06     (2006.01)
A61K 31/437    (2006.01)
C07D 471/04    (2006.01)
C07D 417/12    (2006.01)
A61K 47/10     (2017.01)
A61K 9/48      (2006.01)
A61K 47/02     (2006.01)
C07D 417/14    (2006.01)
A61K 47/26     (2006.01)
A61K 31/454    (2006.01)
A61K 9/20      (2006.01)
C07D 513/04    (2006.01)
A61K 9/00      (2006.01)
```
(Continued)

(52) U.S. Cl.
CPC .......... A61K 31/554 (2013.01); A61K 9/008 (2013.01); A61K 9/0014 (2013.01); A61K 9/0019 (2013.01); A61K 9/06 (2013.01); A61K 9/2018 (2013.01); A61K 9/2027 (2013.01); A61K 9/2054 (2013.01); A61K 9/2059 (2013.01); A61K 9/485 (2013.01); A61K 9/4858 (2013.01); A61K 9/4866 (2013.01); A61K 31/437 (2013.01); A61K 31/454 (2013.01); A61K 45/06 (2013.01); A61K 47/02 (2013.01); A61K 47/10 (2013.01); A61K 47/12 (2013.01); A61K 47/26 (2013.01); A61P 31/10 (2018.01); C07D 281/14 (2013.01); C07D 417/12 (2013.01); C07D 417/14 (2013.01); C07D 471/04 (2013.01); C07D 513/04 (2013.01); C07B 2200/07 (2013.01); C07B 2200/13 (2013.01)

(58) Field of Classification Search
CPC .......................... C07D 281/14; C07D 281/16
See application file for complete search history.

(56) References Cited

U.S. PATENT DOCUMENTS

2,973,354 A    2/1961  Werner
3,367,930 A *  2/1968  Schmutz .............. C07D 267/20
                                                    540/461

(Continued)

FOREIGN PATENT DOCUMENTS

CH    442312 A    8/1967
CH    500223 A    12/1970

(Continued)

OTHER PUBLICATIONS

Jaques et al. (Helvetica Chinnica Acta (1959), 42, 1265-78). Abstract.*

(Continued)

*Primary Examiner* — Bruck Kifle
(74) *Attorney, Agent, or Firm* — Haukaas Fortius PLLC; Michael H. Haukaas

(57) ABSTRACT

The invention provides antifungal compounds, antifungal compositions, and intermediates for the preparation of antifungal compounds and antifungal compositions. The invention also provides methods of inhibiting fungi and methods of treating fungal infections, for example, with a compound or composition described herein. The antifungal compositions can include antifungal adjuvants such as essential oils or essential oil extracts, which adjuvants further improve the antifungal activity of the compositions.

7 Claims, 41 Drawing Sheets

(51) Int. Cl.
  *A61K 9/06*     (2006.01)
  *A61K 47/12*    (2006.01)
  *A61P 31/10*    (2006.01)

(56) References Cited

U.S. PATENT DOCUMENTS

| | | |
|---|---|---|
| 4,728,735 A | 3/1988 | Belanger et al. |
| 5,550,122 A | 8/1996 | Hargrave et al. |
| 5,607,929 A | 3/1997 | Nicol et al. |
| 8,557,984 B2 | 10/2013 | Bouillot et al. |
| 8,993,554 B2 | 3/2015 | Amans et al. |
| 9,023,842 B2 | 5/2015 | Gosmini et al. |
| 9,029,395 B2 | 5/2015 | Amans et al. |
| 9,085,582 B2 | 7/2015 | Bailey |
| 9,249,161 B2 | 2/2016 | Albrecht et al. |
| 9,315,487 B2 | 4/2016 | Amans et al. |
| 9,360,482 B2 | 6/2016 | Bamborough et al. |
| 9,662,311 B2 | 5/2017 | Liu et al. |
| 9,675,697 B2 | 6/2017 | Wang et al. |
| 10,166,215 B2 | 1/2019 | Liu et al. |
| 2012/0202799 A1 | 8/2012 | Crowe et al. |
| 2012/0208800 A1 | 8/2012 | Chung et al. |
| 2012/0277249 A1 | 11/2012 | Andersson et al. |
| 2015/0133436 A1 | 5/2015 | Chung et al. |
| 2015/0232465 A1 | 8/2015 | Bair et al. |
| 2017/0145021 A1 | 5/2017 | Bailey et al. |
| 2017/0197972 A1 | 7/2017 | Gosmini et al. |

FOREIGN PATENT DOCUMENTS

| | | |
|---|---|---|
| WO | 2006116157 A2 | 11/2006 |
| WO | 2006120565 A3 | 8/2007 |
| WO | 2008036139 A2 | 3/2008 |
| WO | 2008036139 A3 | 12/2008 |
| WO | 2010080712 A2 | 7/2010 |
| WO | 2010080712 A3 | 11/2010 |
| WO | 2015017412 A1 | 2/2015 |
| WO | 2015129927 A1 | 9/2015 |
| WO | 2017053510 A1 | 3/2017 |

OTHER PUBLICATIONS

Kalandadze et al. (Izvestiya Vysshikh Uchebnykh Zavedenii, Khimiya i Khimicheskaya Tekhnologiya (2007), 50(1), 78-81). Abstract.*

Kalandadze et al. (Izvestiya Vysshikh Uchebnykh Zavedenii, Khimiya i Khimicheskaya Tekhnologiya (2007), 50(9), 3-6). Abstract.*

International Search Report and Written Opinion of the ISA/US dated Nov. 17, 2017 in International Application No. PCT/US2017/044026; 11pgs.

Mietton, Flore et al., Selective BET bromodomain inhibition as an antifungal therapeutic strategy, Nature Communications, 8:15482, May 18, 2017, 15 pages.

Substance Record for SID 106347312; Pubchem Open Chemistry Database; Feb. 2011, 6pgs.

Substance Record for SID 109560187; Pubchem Open Chemistry Database; Feb. 2011, 6pgs.

Substance Record for SID 165182368; Pubchem Open Chemistry Database; Nov. 2013, 7pgs.

Bigioni et al., "Set-Up of a New Series of HDAC Inhibitors: The 5,11-dihydrodibenzo[b,e]azepin-6-ones As Privileged Structures," Bioorg. Med. Chem. Lett., 22(17):5360-5362, Sep. 2012.

Chemical Abstracts Plus STN REGISTRY Database, Record for AN 1989: 407255, 1989.

Chemical Abstracts Plus STN REGISTRY Database, Record for AN 1991: 559089, 1991.

Chemical Abstracts Plus STN REGISTRY Database, Record for AN 1994: 133355, 1994.

Chemical Abstracts Plus STN REGISTRY Database, Record for AN 1994: 217538, 1994.

Chemical Abstracts Plus STN REGISTRY Database, Record for AN 1994: 409193, 1994.

Chemical Abstracts Plus STN REGISTRY Database, Record for AN 1999: 607184, 1999.

Chemical Abstracts Plus STN REGISTRY Database, Record for AN 2000: 487671, 2000.

Laha et al., "Palladium-Catalyzed Regio- and Chemoselective Ortho-Benzylation of C—H Bond Using a Functionalizable Primary Amide Directing Group: A Concise Synthesis of Dibenzo[b,e]azepin-6-ones," Chem Commun (Camb)., 49(69):7623-7625, Sep. 2013.

Morelock et al., "Estimation and Correlation of Drug Water Solubility with Pharmacological Parameters Required for Biological Activity," J Pharm Sci., 83(7):948-952, Jul. 1994.

Partial Supplementary Search Report of the European Patent Office dated Mar. 2, 2020 in EP Application No. 17835234.0; 19pgs.

Warawa et al., "Behavioral Approach to Nondyskinetic Dopamine Antagonists: Identification of Seroquel," J Med Chem., 44(3):372-389, Feb. 2001.

Werner et al., "Derivatives of Morphanthridine," J. Med. Chem., 8(1):74-80, Jan. 1965.

Binaschi et al., "Antiproliferative and Differentiating Activities of a Novel Series of Histone Deacetylase Inhibitors," ACS Med. Chem. Lett., 1(8):411-415, Jul. 2010.

Chemical Abstracts STN REGISTRY Database, Record for RN 1189644-14-1, Oct. 2009.

Chemical Abstracts STN REGISTRY Database, Record for RN 1189961-72-5, Oct. 2009.

Chemical Abstracts STN REGISTRY Database, Record for RN 1358800-25-5, Feb. 2012.

Chemical Abstracts STN REGISTRY Database, Record for RN 1358831-12-5, Feb. 2012.

Chemical Abstracts STN REGISTRY Database, Record for RN 1358915-86-2, Mar. 2012.

Chemical Abstracts STN REGISTRY Database, Record for RN 1358915-94-2, Mar. 2012.

Chemical Abstracts STN REGISTRY Database, Record for RN 1359492-28-6, Mar. 2012.

Chemical Abstracts STN REGISTRY Database, Record for RN 1359492-68-4, Mar. 2012.

Fisher et al., "Imidazo[1,2-a]pyridine Anthelmintic and Antifungal Agents," J. Med. Chem., 15(9):982-985, Sep. 1972.

Sapegin et al., "Synthesis of N-Substituted pyrido[3,2-B][1,4]benzothiazepin-(L 1H)-One Derivatives by Denitrocyclisation Reaction," Russian Chem Bulletin, Intl Ed., 58(7):1542-1545, Jul. 2009.

Substance Record for CID 46350361; Pubchem Open Chemistry Database; May 2020, 7pgs.

Supplementary Search Report of the European Patent Office dated Jun. 26, 2020 in EP Application No. 17835234.0; 28pgs.

Xiao et al., "Discovery, Optimization, and Characterization of Novel D2 Dopamine Receptor Selective Antagonists," J. Med. Chem., 57(8):3450-3463, Mar. 2014.

* cited by examiner c d a

% Identity within BD1

|  |  | human | | | | S.cer | C.alb | C.gla |
|---|---|---|---|---|---|---|---|---|
|  |  | Brd2 | Brd3 | Brd4 | Brdt | Bdf1 | Bdf1 | Bdf1 |
| % Identity within BD2 | Brd2 | -- | 87 | 79 | 74 | 35 | 31 | 35 |
| | Brd3 | 82 | -- | 81 | 74 | 32 | 31 | 33 |
| human | Brd4 | 81 | 81 | -- | 73 | 35 | 32 | 34 |
| | Brdt | 72 | 71 | 74 | -- | 33 | 31 | 31 |
| | S.cer Bdf1 | 39 | 38 | 40 | 41 | -- | 66 | 84 |
| | C.alb Bdf1 | 44 | 42 | 44 | 46 | 58 | -- | 61 |
| | C.gla Bdf1 | 40 | 38 | 37 | 38 | 71 | 57 | -- | b

```
                                    ZA loop                    helix A
                     BD1                    Y187
S.cerevisiae  172  PFLQPVDPVKLDIPE FNYIKRPMDLSTIERK  203
C.glabrata    131  PFLQPVDPVALNIPE FNFIKRPMDLQTIERK  162
C.albicans    210  PFLHPVDTVKLNVPE FNYIPRPMDLSTIERK  241
                                    Y248

BD2                    Y355
S.cerevisiae  340  PFLEPVDPVSMNLPT FDYVKEPMDLGTIAKK  371
C.glabrata    308  PFLEPVDPVALNCPT FDYVKEPMDLGTVSKK  339
C.albicans    387  PFLAPVDTVALNIPN NEIVKQPMDLGTIQSK  418
                                    Y425
```

*Fig. 4* a b c d

CaBdf1-BD1 IC50 = 4.5 µM
hBrd4-BD1 IC50 > 30 µM

CaBdf1-BD1 IC50 = 6.5 µM
hBrd4-BD1 = 6.5 µM

4
CaBdf1-BD1 IC50 = 4.5 µM
hBrd4-BD1 IC50 > 30 µM

CaBdf1-BD1 IC50 = 6.5 µM
hBrd4-BD1 IC50 > 30 µM a b a

MS51 b

C

SELECTIVE BROMODOMAIN INHIBITION OF FUNGAL BDF1

RELATED APPLICATIONS

This application is a National Stage filing under 35 U.S.C. § 371 of International Application No. PCT/US2017/044026, filed Jul. 26, 2017, which claims priority under 35 U.S.C. § 119(e) to U.S. Provisional Patent Application No. 62/366,973, filed Jul. 26, 2016, which applications are incorporated herein by reference.

GOVERNMENT SUPPORT

This invention was made with government support under Grant No. R21AI113704 awarded by the National Institutes of Health. The government has certain rights in this invention.

BACKGROUND OF THE INVENTION

Opportunistic fungal infections are a major cause of morbidity and mortality in immunocompromised individuals including stem cell and organ transplant recipients, individuals with hematologic malignancies, and AIDS patients, with over 800,000 deaths per year worldwide caused by Candidemia, cryptococcal meningitis, invasive aspergillosis and pneumocystis pneumonia collectively. *Candida* species are the major nosocomial pathogens, with a mortality rate of 30-40%. *Candida albicans* and *Candida glabrata* rank first and second in isolation frequency, respectively, and collectively are responsible for 70% of all systemic candidiasis. Invasive fungal infections are currently treated by focusing on one of the following targets: cell membrane integrity (polyene drugs); inhibition of the synthesis of ergosterol (azoles); inhibition of the synthesis of nucleic acids (flucytosine); inhibition of the synthesis of the cell wall (echinocandins).

The emergence of drug resistant strains and the toxicity, high cost, and narrow activity spectrum of the limited repertoire of available drugs pose an urgent need for novel therapeutic agents. Bromodomain (BD) and Extra-Terminal (BET) proteins are chromatin-associated factors that regulate gene transcription and chromatin remodeling. BET proteins recognize chromatin through their two bromodomains (BD1 and BD2), small helical domains which specifically recognize short peptides acetylated on lysine residues. In particular, BET proteins associate via their bromodomains (BDs) with the acetylated N-terminal tails of histones H3 and H4. Several human BET BDs inhibitors have been developed in recent years, and have been used as therapeutic agents for cancer and for other non-infectious human diseases. Furthermore, it will be recognized by those skilled in the art that available drugs to treat fungal infections suffer from disadvantages, and rely upon mechanisms not involving fungal BET proteins.

SUMMARY

Fungal BET protein Bromodomain factor 1 (Bdf1) is a fungal BET protein that regulates the transcription of over 500 genes. We have discovered that Bdf1 is an essential gene in *C. albicans*, a widespread fungal pathogen, and that the functionality of the bromodomains (BDs) within Bdf1 is critical for growth of this organism. This establishes a compelling rationale to devise selective Bdf1 BD inhibitors to treat opportunistic fungal infections. As described herein, selective fungal BD inhibitors have been discovered and evaluated for their antifungal activity.

Accordingly, the invention provides a compound of Formula I:

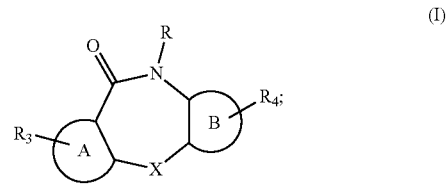

wherein:

X is $CH_2$, O, NH, or S;

Ring A and Ring B are each independently a substituted or non-substituted aryl or a substituted or non-substituted heteroaryl;

R is —$(CH_2)_n$-L, wherein n is 0-4 and L is H, halo, $R_1$, —COO—$R_1$, —CO—$R_1$, —CO—$N(R_1R_2)$, —$S(O)_2$—$R_1$, —$S(O)_2$—$N(R_1R_2)$, —$N(R_1R_2)$, —$N(R_2)COR_1$, a substituted or non-substituted aryl, or a substituted or non-substituted heteroaryl, wherein $R_1$ and $R_2$ are each independently:
(i) H, halo, substituted or non-substituted aryl, or substituted or non-substituted heteroaryl;
(ii) substituted or non-substituted heterocycloalkyl; or
(iii) C1-C8 alkyl, C2-C8 alkenyl, or C2-C8 alkynyl, each comprising 0, 1, 2, or 3 heteroatoms selected from the group consisting of O, S, and N; or substituted or non-substituted C3-C12 cycloalkyl, or substituted or non-substituted C3-C12 cycloalkenyl; and each $R_3$ and $R_4$ is independently:
(i) H, halo, substituted or non-substituted aryl, or substituted or non-substituted heteroaryl;
(ii) substituted or non-substituted heterocycloalkyl;
(iii) C1-C8 alkyl, C2-C8 alkenyl, or C2-C8 alkynyl, each comprising 0, 1, 2, or 3 heteroatoms selected from the group consisting of O, S, and N; or substituted or non-substituted C3-C12 cycloalkyl, or substituted or non-substituted C3-C12 cycloalkenyl; or
(iv) OH, or substituted or non-substituted amine (e.g., NRR), ether (e.g., —OR), amide (e.g., —N(C=O)—R or —C(=O)N—R), or ester (e.g., —O(C=O)—R or —C(=O)O—R) (wherein R is as defined above);

or a pharmaceutically acceptable salt, solvate, or prodrug thereof.

When a group is substituted, the substituent can be any one or more substituents as recited in the list of substituents in the Detailed Description below.

In one embodiment, X is S or O. In one specific embodiment, X is S.

In one embodiment, Ring A and Ring B are each independently selected from substituted or non-substituted phenyl and substituted or non-substituted pyridyl.

In one embodiment, R is —$(CH_2)_n$-L, wherein n is 0, 1, or 2, and L is H, halo, C1-C6 alkyl, C2-C6 alkenyl, C2-C6 alkynyl, or C3-C8 cycloalkyl such as cyclopropyl.

In various embodiments, $R_3$ is H, OH, halo, C1-C4 alkyl, C2-C5 alkenyl, or C2-C5 alkynyl.

In some embodiments, the compound of Formula I is a compound of Formula IA:

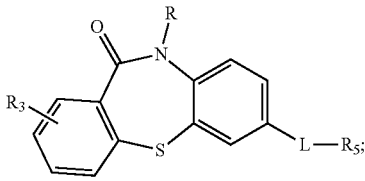

(IA)

wherein
R is C1-C6 alkyl, C2-C6 alkenyl or C2-C6 alkynyl, or cyclopropyl;
L is —NH—C(=O)—, —C(=O)—NH—, or 3,5-oxadiazolyl; and
$R_5$ is substituted or non-substituted aryl, substituted or non-substituted heteroaryl, substituted or non-substituted heterocycloalkyl, —CH($R_6$)-benzamide or —CH($R_6$)-sulfonamide where $R_6$ is a straight-chain or branched C1-C8 alkyl, C4-C18 alkyl, or $((CH_2)_nO)_xCH_3$ where n is 2-4 and x is 1-4. In various specific embodiments, the compound of Formula IA is MS4 or MS5:

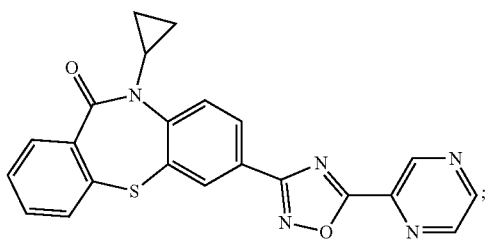

(MS4)

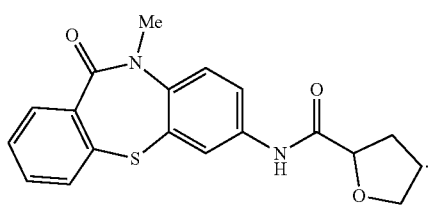

(MS5)

The invention also provides a compound of Formula II or III:

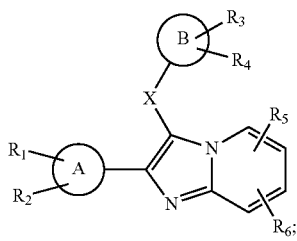

(II)

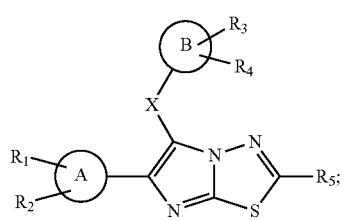

(III)

wherein:
X is NH, NHC(O), O or S;
Ring A and Ring B are each independently a substituted or non-substituted aryl (e.g., phenyl) or a substituted or non-substituted heteroaryl;
$R_1$, $R_2$, $R_3$ and $R_4$ are each independently H, Alk, OH, $NH_2$, NHAlk, OAlk, halo, cycloalkyl, C(O)OH, C(O)OAlk, $C(O)NH_2$, C(O)NHAlk, $S(O)_2OH$, $S(O)_2NH_2$, $S(O)_2NHAlk$, or NHC(O)Alk, wherein Alk is a substituted or non-substituted $C_1$-$C_{18}$ alkyl or $((CH_2)_nO)_xCH_3$ where n is 2-4 and x is 1-4;
$R_5$ is H, Alk, OH, $NH_2$, NHAlk, OAlk, halo, cycloalkyl, C(O)OH, C(O)OAlk, $C(O)NH_2$, C(O)NHAlk, $S(O)_2OH$, $S(O)_2NH_2$, $S(O)_2NHAlk$, or NHC(O)Alk, wherein Alk is substituted or non-substituted $C_1$-$C_{18}$ alkyl or $((CH_2)_nO)_xCH_3$ where n is 2-4 and x is 1-4, or $R^{10}$ where $R^{10}$ is piperidin-1-yl, morpholino or another nitrogen-containing heterocyclic substituent; and
$R_6$ is H, Alk, OH, $NH_2$, NHAlk, OAlk, halo, cycloalkyl, C(O)OH, C(O)OAlk, $C(O)NH_2$, C(O)NHAlk, $S(O)_2OH$, $S(O)_2NH_2$, $S(O)_2NHAlk$, or NHC(O)Alk, wherein Alk is substituted or non-substituted $C_1$-$C_{18}$ alkyl or $((CH_2)_nO)_xCH_3$ where n is 2-4 and x is 1-4; or a pharmaceutically acceptable salt, solvate, or prodrug thereof.
In some embodiments, X is NH or NHC(O).
In various embodiments, Ring A and Ring B are each independently selected from substituted or non-substituted phenyl, substituted or non-substituted pyridyl, and substituted or non-substituted pyrazole.
In one embodiment, $R_1$ is OH or Me, optionally at the para position with respect to the Ring A attachment to the heterocyclic core of Formula II or III, wherein Ring A is a six-membered ring.
In some embodiments, $R_3$ is methyl. In various embodiments, $R_4$ is H or OH. In additional embodiments, $R_5$ is optionally methyl or piperidine-1-yl.
The compound of Formula II can be a compound of Formula IIA:

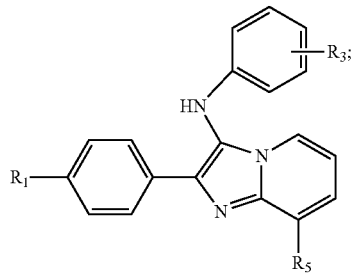

(IIA)

wherein:
$R_1$ is H, Alk, OH, $NH_2$, NHAlk, OAlk, halo, cycloalkyl, C(O)OH, C(O)OAlk, $C(O)NH_2$, C(O)NHAlk, $S(O)_2OH$, $S(O)_2NH_2$, $S(O)_2NHAlk$, or NHC(O)Alk, wherein Alk is a substituted or non-substituted $C_1$-$C_{18}$ alkyl or $((CH_2)_nO)_xCH_3$ where n is 2-4 and x is 1-4; and
$R_3$ is Alk, NHAlk, OAlk, cycloalkyl, C(O)OAlk, C(O)NHAlk, $S(O)_2NHAlk$, or NHC(O)Alk, wherein Alk is a substituted or non-substituted $C_1$-$C_{18}$ alkyl or $((CH_2)_nO)_xCH_3$ where n is 2-4 and x is 1-4 (wherein $R_3$ is preferably meta, or more preferably para, to the nitrogen of its phenyl ring); and
$R_5$ is H, Alk, OH, $NH_2$, NHAlk, OAlk, halo, cycloalkyl, C(O)OH, C(O)OAlk, $C(O)NH_2$, C(O)NHAlk, $S(O)_2OH$, S(O)$_2$NH$_2$, S(O)$_2$NHAlk, or NHC(O)Alk, wherein Alk is substituted or non-substituted C$_1$-C$_{18}$ alkyl or ((CH$_2$)$_n$O)$_x$CH$_3$ where n is 2-4 and x is 1-4, or R$^{10}$ where R$^{10}$ is piperidin-1-yl, morpholino or another nitrogen-containing heterocyclic substituent;

or a pharmaceutically acceptable salt or solvate thereof.

In one specific embodiment, the compound of Formula II is MS51:

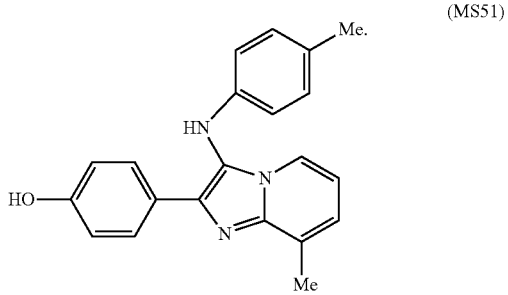 [SMILES: Cc1ccc(Nc2c(-c3ccc(O)cc3)nc3c(C)cccn23)cc1]

(MS51)

In another specific embodiment, the compound of Formula III is:

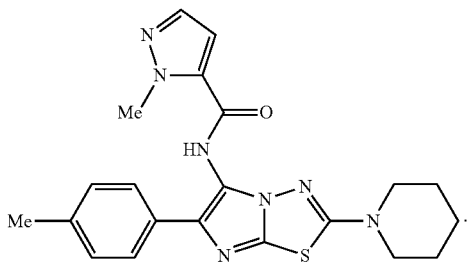 [SMILES: Cc1ccc(-c2nc3sc(N4CCCCC4)nn3c2NC(=O)c2ccnn2C)cc1]

The compounds can have greater binding activity to fungal Bromodomain factor 1 (Bdf1) compared to Bromodomain and Extra-Terminal (BET) proteins of humans or other animals. Additionally, the compounds can be selective for a fungal BD1 over BD2, or vice versa.

The invention further provides a compound of Formula IV:

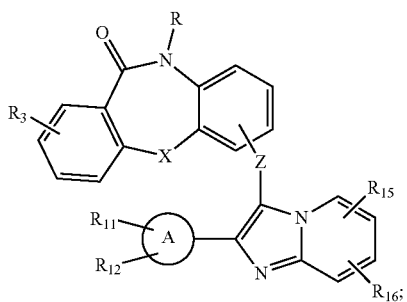

(IV)

wherein:

X is CH$_2$, O, NH, or S;

R is —(CH$_2$)$_n$-L, wherein n is 0-4 and L is H, halo, R$_1$, —COO—R$_1$, —CO—R$_1$, —CO—N(R$_1$R$_2$), —S(O)$_2$—R$_1$, —S(O)$_2$—N(R$_1$R$_2$), —N(R$_1$R$_2$), —N(R$_2$)COR$_1$, a substituted or non-substituted aryl, or a substituted or non-substituted heteroaryl, wherein R$_1$ and R$_2$ are each independently:

(i) H, halo, a substituted or non-substituted aryl or a substituted or non-substituted heteroaryl;

(ii) a substituted or non-substituted heterocycloalkyl; or (iii) a C1-C8 alkyl, C2-C8 alkenyl or C2-C8 alkynyl, each comprising 0, 1, 2, or 3 heteroatoms selected from the group consisting of O, S, and N; or a substituted or non-substituted C3-C12 cycloalkyl or substituted or non-substituted C3-C12 cycloalkenyl; and R$_3$ is (i) H, halo, a substituted or non-substituted aryl, or a substituted or non-substituted heteroaryl; (ii) a substituted or non-substituted heterocycloalkyl; (iii) a C1-C8 alkyl, C2-C8 alkenyl or C2-C8 alkynyl, each comprising 0, 1, 2, or 3 heteroatoms selected from the group consisting of O, S, and N; or a substituted or non-substituted C3-C12 cycloalkyl or substituted or non-substituted C3-C12 cycloalkenyl; or (iv) OH, or a substituted or non-substituted amine, ether, amide, or ester;

Z is a linking moiety wherein the linking moiety is a divalent radical of 1 to 40 atoms in a linear chain, wherein the linear chain comprises at least one carbon or nitrogen atom, and when the linear chain comprises 2 to 40 atoms, the chain comprises 0-8 heteroatoms selected from the group consisting of O, S, and N, which chain is optionally interrupted by 1 or 2 cycloalkyl, heterocycloalkyl, aryl, or heteroaryl groups;

Ring A is a substituted or non-substituted aryl or a substituted or non-substituted heteroaryl;

R$_{11}$ and R$_{12}$ are each independently H, Alk, OH, NH$_2$, NHAlk, OAlk, halogen, cycloalkyl, C(O)OH, C(O)OAlk, C(O)NH$_2$, C(O)NHAlk, S(O)$_2$OH, S(O)$_2$NH$_2$, or S(O)$_2$NHAlk, wherein Alk is a substituted or non-substituted C$_1$-C$_4$ alkyl;

R$_{15}$ is H, Alk, OH, NH$_2$, NHAlk, OAlk, halo, cycloalkyl, C(O)OH, C(O)OAlk, C(O)NH$_2$, C(O)NHAlk, S(O)$_2$OH, S(O)$_2$NH$_2$, or S(O)$_2$NHAlk, wherein Alk is a substituted or non-substituted C$_1$-C$_4$ alkyl or R$^Z$, where R$^Z$ is piperidin-1-yl, morpholino or another nitrogen-containing heterocyclic substituent; and R$_{16}$ is H, Alk, OH, NH$_2$, NHAlk, OAlk, halo, cycloalkyl, C(O)OH, C(O)OAlk, C(O)NH$_2$, C(O)NHAlk, S(O)$_2$OH, S(O)$_2$NH$_2$, or S(O)$_2$NHAlk, wherein Alk is a substituted or non-substituted C$_1$-C$_4$ alkyl;

or a pharmaceutically acceptable salt, solvate, or prodrug thereof.

In one embodiment, Z is a divalent radical of the formula -W-A-W- wherein each W is independently —N(R')C(=O)—, —C(=O)N(R')—, —OC(=O)—, —C(=O)O—, —O—, —S—, —S(O)—, —S(O)$_2$—, —N(R')—, —C(=O)—, —(CH$_2$)$_n$— where n is 1-3, or a direct bond; wherein each R' is independently H, (C$_1$-C$_6$)alkyl, or a nitrogen protecting group; and A is (C$_1$-C$_{16}$)alkyl, (C$_2$-C$_{16}$)alkenyl, (C$_2$-C$_{16}$)alkynyl, (C$_3$-C$_8$)cycloalkyl, heterocycloalkyl, heteroaryl, (C$_6$-C$_{10}$)aryl, —NH—, —(OCH$_2$—CH$_2$)$_n$— where n is 1 to about 10, —C(O)NH(CH$_2$)$_n$ wherein n is 1 to about 6, or (C$_1$-C$_{20}$)alkyl, (C$_2$-C$_{16}$)alkenyl, (C$_2$-C$_{16}$)alkynyl, or —(OCH$_2$—CH$_2$)$_n$— interrupted between two carbons, or between a carbon and an oxygen, with a (C$_3$-C$_8$)cycloalkyl, heterocycloalkyl, heteroaryl, or (C$_6$-C$_{10}$)aryl group.

In one embodiment, Z is NH, —NH-A-C(=O)—NH— where A is phenyl, heterocycloalkyl, or heteroaryl.

In some embodiments, Z is NH or —NH-Ph-C(=O)—NH—.

In various embodiments, R is Me, Et, or cyclopropyl.

In one embodiment, R$_3$ is H, R$_{11}$ is OH or Me, and R$_{15}$ is methyl or piperidine-1-yl.

In one specific embodiment, the compound of Formula IV is:

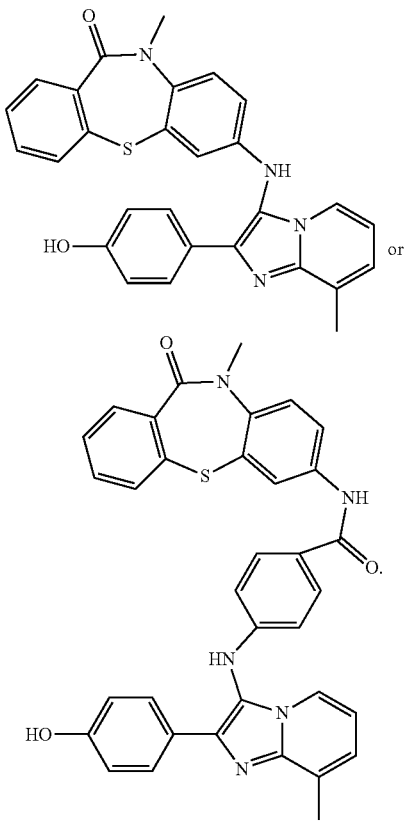

The compounds described herein are effective for the treatment of standard fungal infections, in addition to fungal infections that are resistant to antifungal drugs that are not compounds of any one of formulas I-IV. Thus, the invention provides a compound (e.g., a compound described above) that is effective against a strain of a *Candida* species that is resistant to other antifungal drugs. The invention further provides a composition comprising a compound described herein (e.g., a compound of any one of the formulas described above), a second antifungal drug, and a pharmaceutically acceptable diluent, excipient, or carrier. The compositions can include an antifungal adjuvant. The antifungal adjuvant can be an essential oil or an essential oil extract, such as sweet orange, *Mentha arvensis*, peppermint, cedarwood, lemon, *Eucalyptus globulus, Litsea cubeba*, clove, spearmint, nutmeg, cinnamon, basil, bay leaf, or a combination thereof. In one specific embodiment, the essential oil extract is eugenol.

The invention further provides a method of reducing or impairing the growth of a fungal culture comprising exposing the culture to a compound that inhibits one or both fungal bromodomain proteins, wherein the compound is a compound of any one of formulas I-IV, and the growth of the fungal culture is thereby reduced or impaired.

The invention yet further provides a method of treating a fungal infection in a subject in need thereof comprising administering to the subject an effective antifungal amount of a compound that inhibits one or both fungal bromodomain proteins, wherein the compound is a compound of any one of formulas I-IV, and the fungal infection is thereby treated. The compound can have a greater binding activity to Bdf1 compared to BET proteins of human or other animals. The compound can also be effective against a strain of a *Candida* species that is resistant to other antifungal drugs.

The compound can be administered, concurrently or sequentially, in combination with a second antifungal drug. In some embodiments, the second antifungal drug is amphotericin, anidulafungin, caspofungin, clotrimazole, fluconazole, flucytosine, itraconazole, ketoconazole, micafungin, miconazole, posaconazole, voriconazole, or a combination thereof. The invention therefore provides for the use of a compound according to any one of formulas I-IV for the treatment of a fungal infection.

Thus, in another aspect, a method of reducing or impairing the growth of a fungal culture is provided. The method includes exposing the culture to at least one compound that inhibits one or both bromodomains of Bdf1 protein. In the method, the compound can have greater binding activity to Bdf1 compared to BET proteins of human or other animals.

In a further aspect, a method of treating a fungal infection in a subject in need thereof is provided. The method includes administering to the subject at least one compound that inhibits one or both bromodomains of Bdf1 protein. In the method, the compound can have greater binding activity to Bdf1 compared to BET proteins of human or other animals. In some embodiments, the compound is effective against a *Candida* species that is resistant to other antifungal drugs such as fluconazole. In some embodiments, the compound can be administered with another antifungal drug such as amphotericin, anidulafungin, caspofungin, clotrimazole, fluconazole, flucytosine, itraconazole, ketoconazole, micafungin, miconazole, posaconazole, or voriconazole.

In the method of reducing or impairing the growth of a fungal culture, or the method of treating a fungal infection, the at least one compound can selectively inhibit either BD1 or BD2, or both BD1 and BD2, of fungal Bdf1 protein. The compound can be provided as a pharmaceutical composition comprising a physiologically or pharmaceutically acceptable diluent, excipient, or carrier.

The invention thus provides novel compounds of the formulas described herein, intermediates for the synthesis of compounds of the formulas described herein, as well as methods of preparing compounds of the formulas described herein. The invention also provides compounds of the formulas described herein that are useful as intermediates for the synthesis of other useful compounds. The invention provides for the use of compounds of the formulas described herein for the manufacture of medicaments useful for the treatment of fungal infections in a mammal, such as a human. The invention thus provides for the use of the compositions described herein for use in medical therapy. The medical therapy can be treating a fungal infection or the symptoms thereof. The medicament can include a pharmaceutically acceptable diluent, excipient, carrier, adjuvant, or combination thereof.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention. For a more complete understanding of the present invention, reference is now made to the following descriptions taken in conjunction with the accompanying drawings.

DETAILED DESCRIPTION

The present application describes small molecules that selectively inhibit Bdf1 BDs (BD1 and/or BD2). Several of the small molecules have been identified by in vitro assays and experiments based on the comparison of the three-dimensional field pattern of a library of small molecules with that of a reference pattern. This reference field pattern is determined using the crystal structure of one of the inhibitors reported herein in complex with CaBdf1BD1.

In another aspect, small molecules are provided for reducing or impairing the growth of fungal cultures via inhibition of Bdf1 BDs.

In a further aspect, small molecules are provided for reducing or curing a fungal infection via selective binding to Bdf1 BDs. The fungal infection can be a localized infection such as candidiasis, or a systemic infection such as candidemia.

In another aspect, a pharmaceutical composition is provided that contains one or more of the compounds disclosed above that inhibit Bdf1 BDs, or a pharmaceutically acceptable salt or prodrug thereof. In one embodiment, one of the compounds in the composition may be a different antifungal compound, which can be an FDA approved antifungal drug such as fluconazole, and the like. In some embodiments, the Bdf1-inhibiting compounds can be used to treat fungal infections that are resistant to other antifungal agents/drugs. In some embodiments, a Bdf1-inhibiting compound can selectively inhibit either BD1 or BD2 of fungal Bdf1 protein, or both BD1 and BD2 of a fungal Bdf1 protein. Combinations comprising one compound that inhibits BD1 and another compound that inhibits BD2 are also disclosed herein. The pharmaceutical composition can be used against yeast pathogens such as, but not limited to, *C. albicans* and *C. glabrata*.

Figure 1:
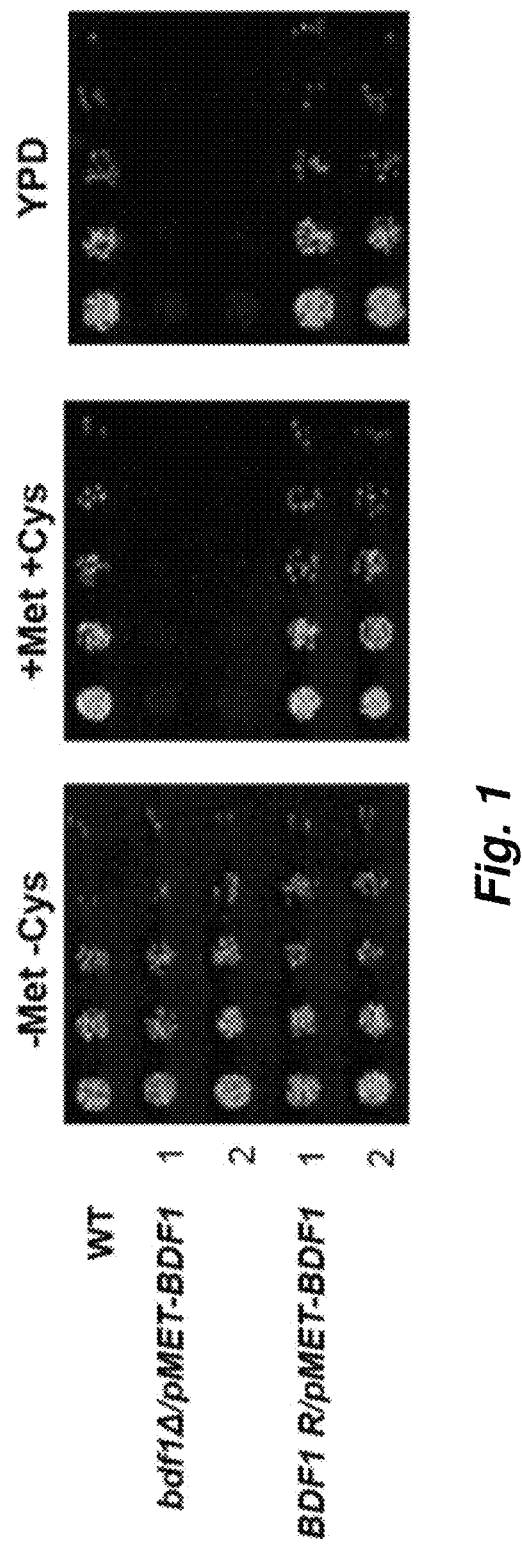
FIG. 1. Mutations that inactivate the two C. albicans Bdf1 (CaBdf1) bromodomains disrupt cell viability and growth, showing that blocking these domains should have a similar effect and increase susceptibility to antifungal drugs.
Figure 1:
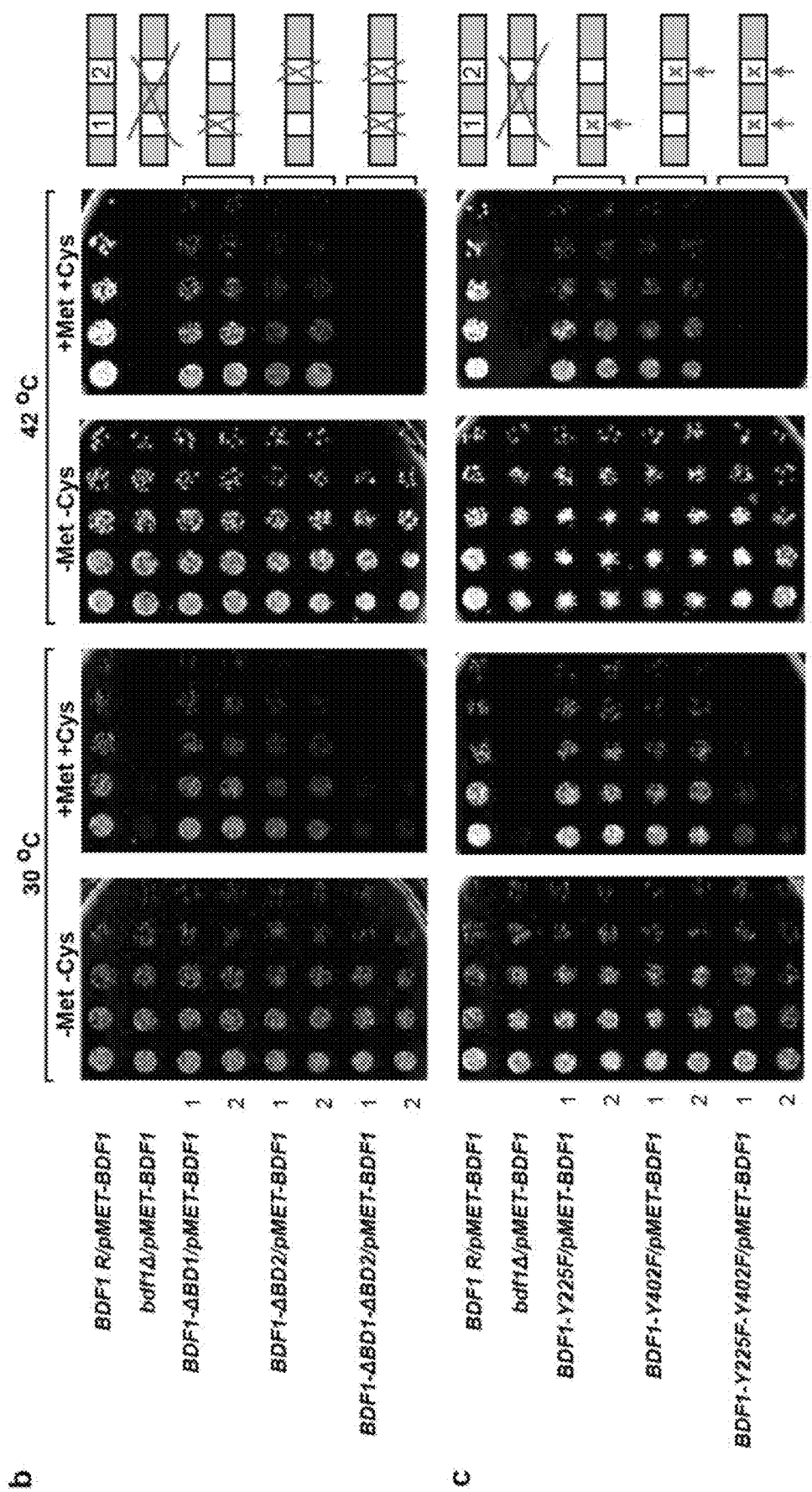

Referring to the figures, FIG. 1 shows how Bdf1 bromodomain functionality is required for growth and fitness of *C. albicans*. FIG. 1a shows that Bdf1 is essential in *C. albicans*. One allele was deleted and the other placed under pMET control. Bdf1 expression is repressed in SC media containing methionine and cysteine or in rich media (YPD). Rescue of the deleted strain confirms that the observed phenotype is due to the absence of Bdf1. FIG. 1b shows that Bdf1 bromodomain deletion compromises growth. One or both bromodomains were deleted from one Bdf1 allele, while the other allele was under pMET control. Deleting both bromodomains nearly phenocopies the full BDF1 deletion. The temperature of 42° C., mimicking a heat shock, aggravates the phenotypes observed at 30° C. FIG. 1c shows bromodomain inactivation by point mutation. We constructed single and double point mutants by replacing residues Tyr225 or Asn268 in BD1 and Tyr402 or Asn445 in BD2 by phenylalanine and alanine, respectively. In human BET bromodomains, these residues either mediate a direct (Asn) or water-mediated (Tyr) hydrogen bond to the acetylated histone peptide.

Figure 2:
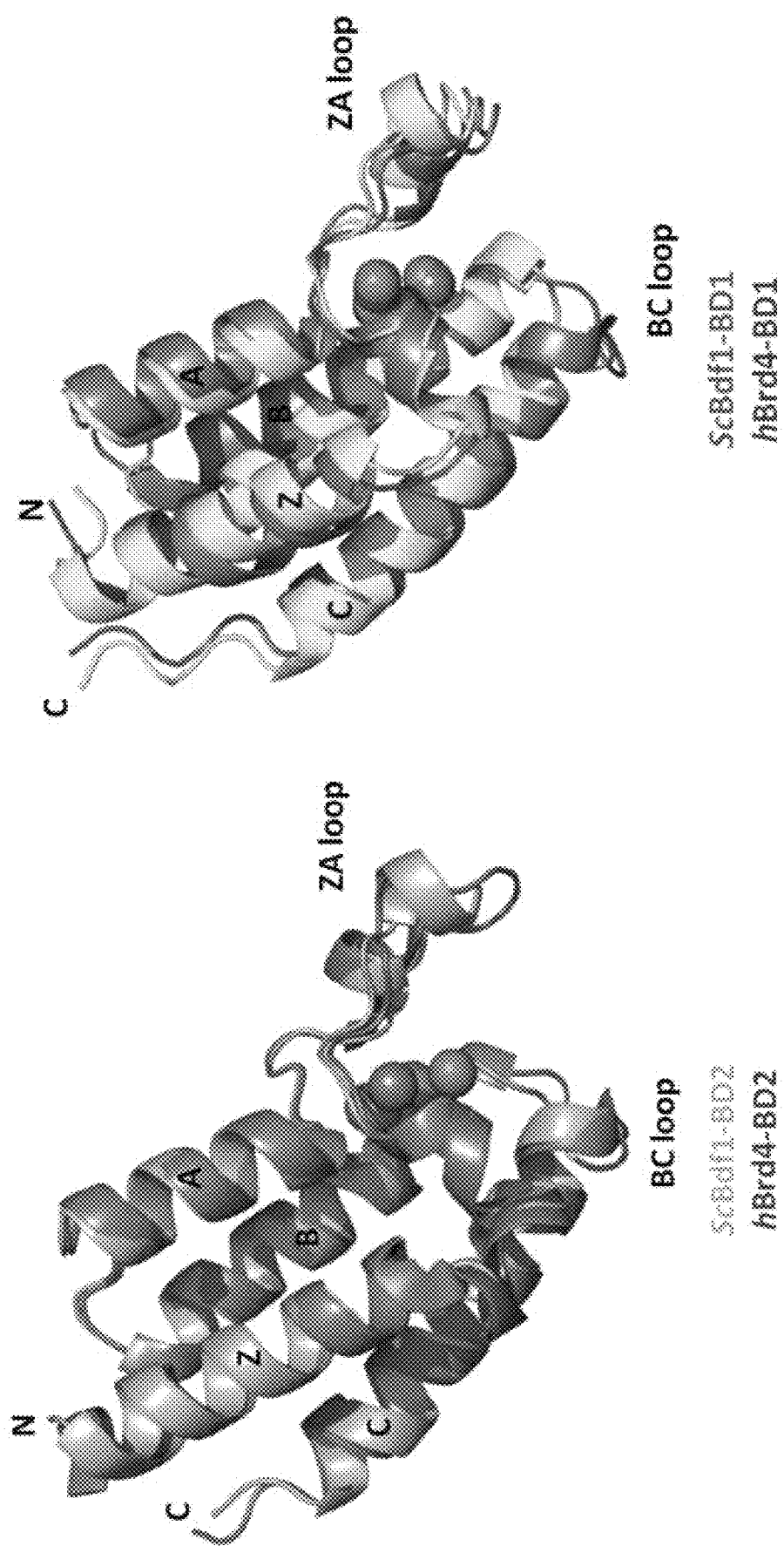
FIG. 2. Atomic resolution crystal structures of fungal Bdf1 BDs reveal structural features that are fundamental for the design of potent and selective inhibitors. Structural differences between human and fungal bromodomains allow selective inhibition of the latter.
Figure 2:
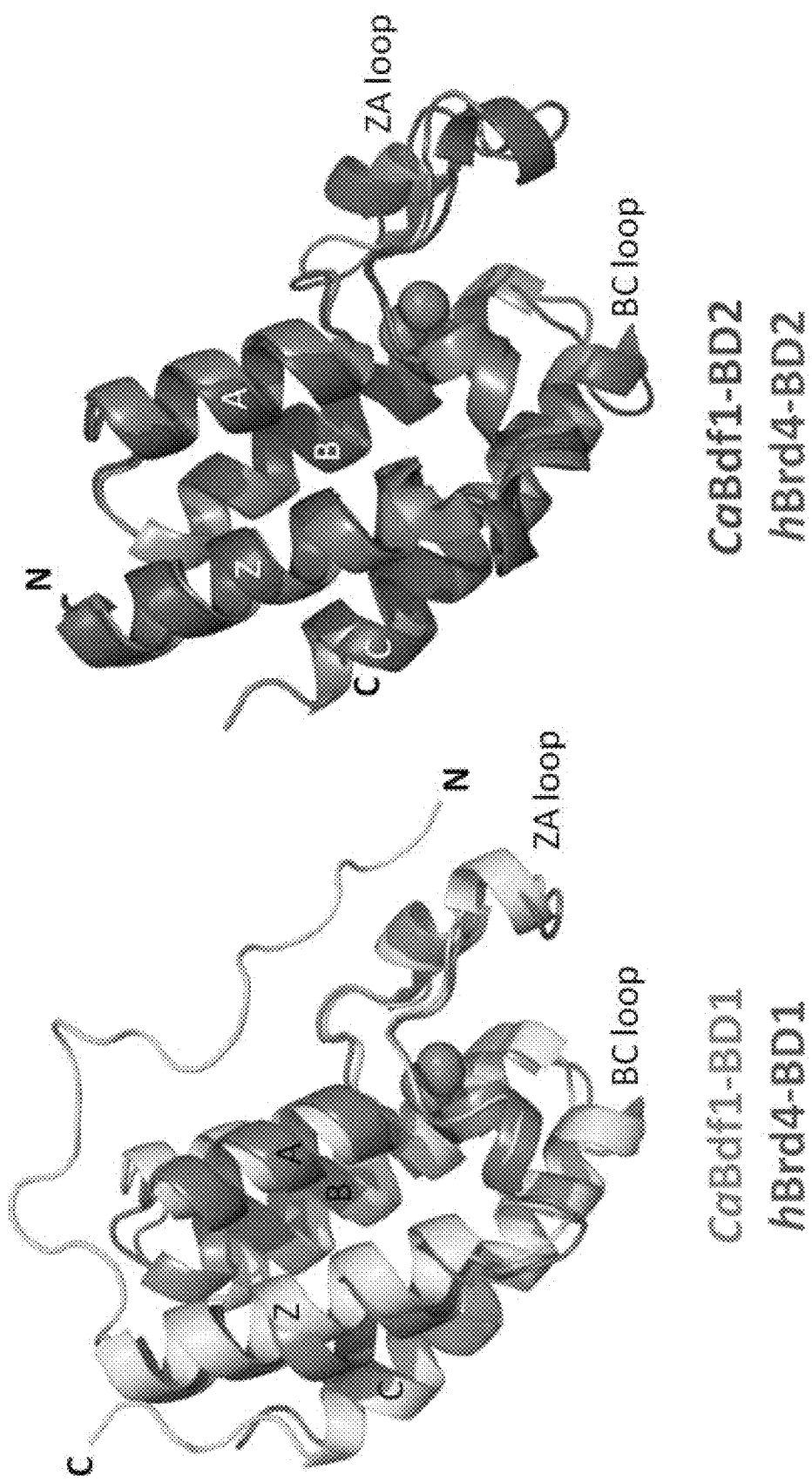
Figure 2:
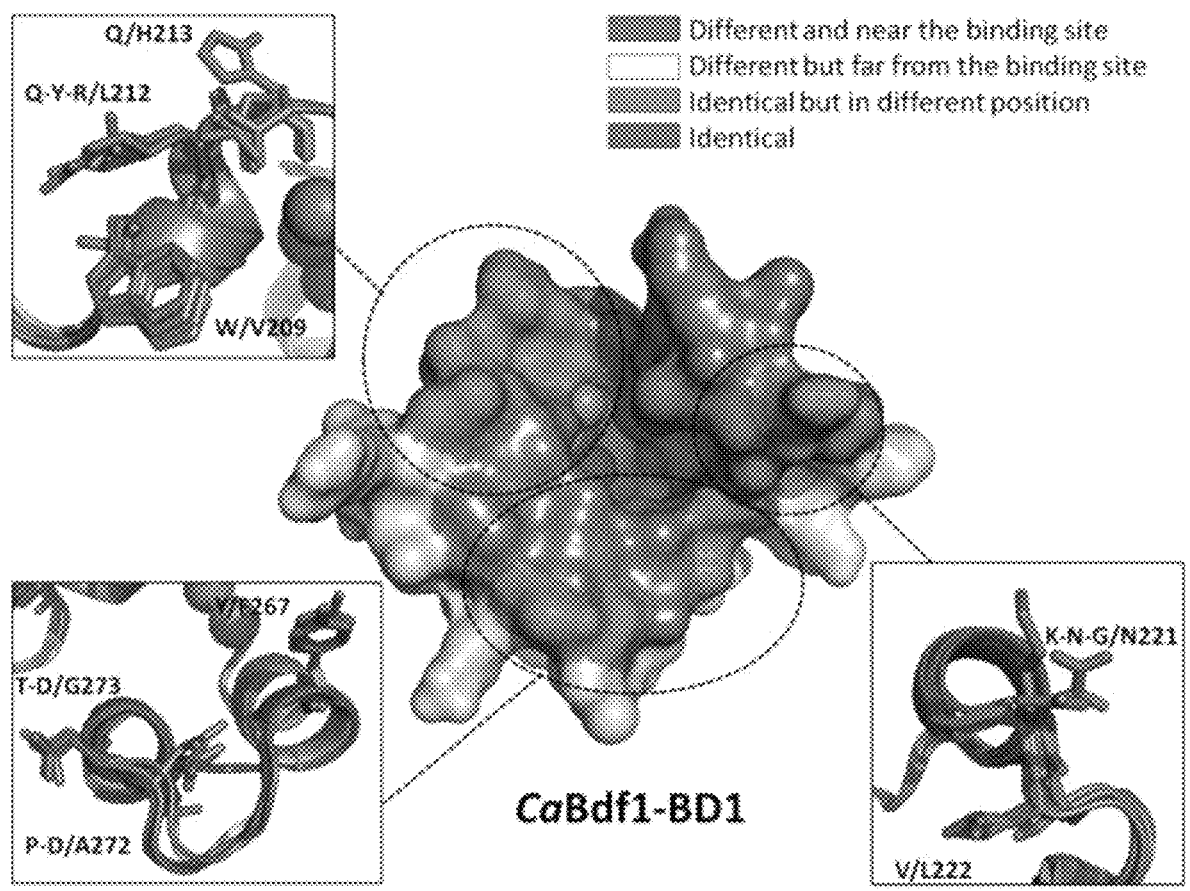
Figure 2:
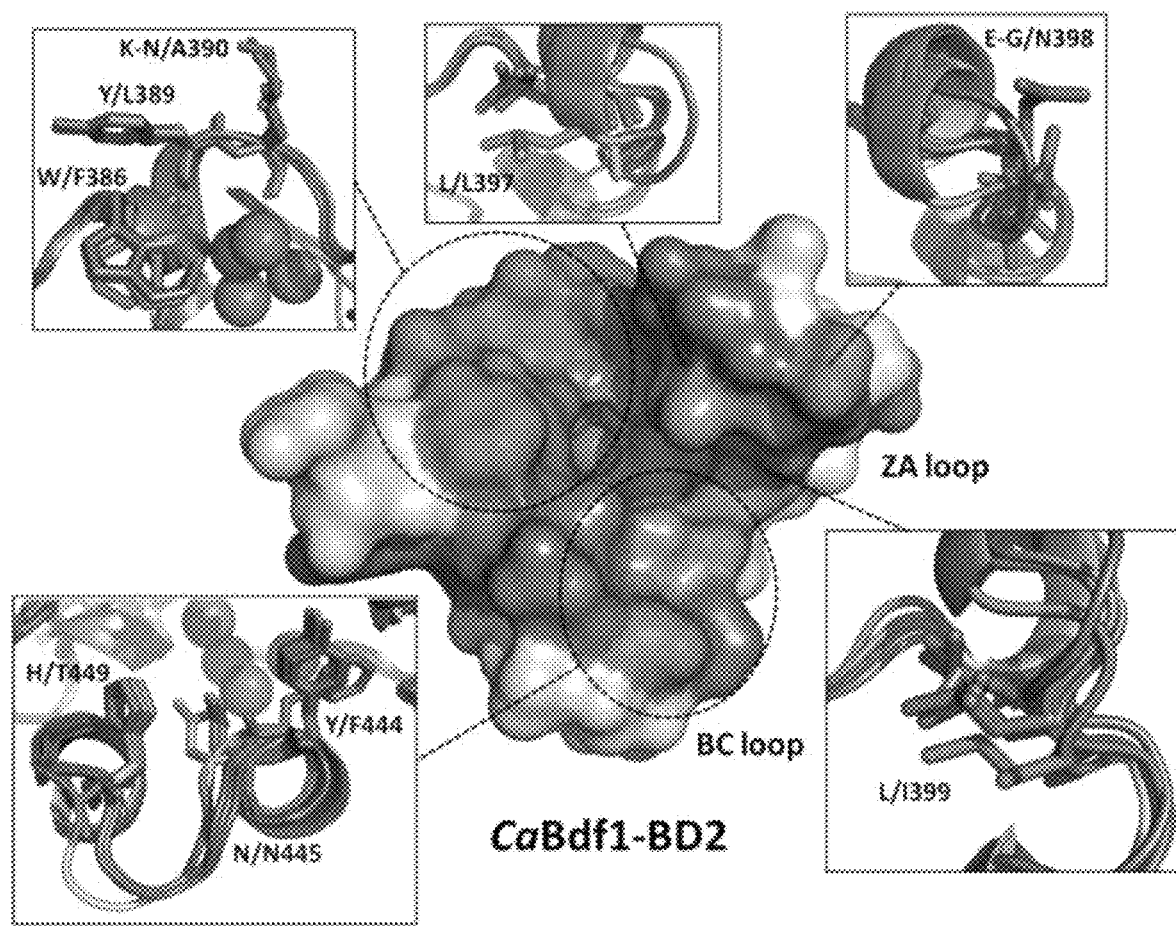

FIG. 2 shows the atomic resolution crystal structures of *S. cerevisiae* and *C. albicans* Bdf1 BDs. Like canonical bromodomains, the fungal structures comprise a left-handed bundle of four helices ($\alpha Z$, $\alpha A$, $\alpha B$ and $\alpha C$) with the ZA and BC loops defining the ligand binding pocket. The structures resemble those of the human BET bromodomains, with most residues within the ligand binding pocket, including four structured water molecules important for ligand recognition, conserved between the human and fungal orthologs. However, several residues differ in identity or spatial location, resulting in small but significant differences in the stereochemical properties of the ligand binding pocket.

Formulas I-IV provide chemical structures that summarizes the 2D structural features displayed by classes of molecules that include compounds that display high activity for one of the bromodomains of *C. albicans* Bdf1 and that are selective for the fungal domains over human Brd4 bromodomains. One main scaffold is an azepinone, which is optionally made into a thia, oxa, or diazepinone. Fused to the azepinone scaffold are two aromatic rings (aryl or heteroaryl), optionally substituted. Also, the nitrogen atom on the azepinone scaffold is optionally substituted, such as with aryl or alkyl substituents, which can in turn be optionally substituted.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five, or one to four, for example if the phenyl ring is disubstituted.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The term "about" can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, composition, or embodiment. The term about can also modify the end-points of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

In some embodiments, compounds contain substituted hydrocarbyl groups (e.g., substituted alkyl, cycloalkyl, or heterocycloalkyl groups). The term "substituted hydrocarbyl" refers to a hydrocarbyl group in which one or more bonds to a carbon(s) or hydrogen(s) are replaced by a bond to non-hydrogen and non-carbon atoms such as, but not limited to, a halogen atom in halides such as F, Cl, Br, and I; an oxygen atom in groups such as hydroxyl groups, alkoxy groups, aryloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as in trialkylsilyl groups, dialkylarylsilyl groups, alkyldiarylsilyl groups, and triarylsilyl groups; and other heteroatoms in various other groups. Substituted hydrocarbyl groups also include groups in which one or more bonds to a carbon(s) or hydrogen(s) atom is replaced by a bond to a heteroatom such as oxygen in carbonyl, carboxyl, and ester groups; or nitrogen in groups such as imines, oximes, hydrazones, and nitriles.

In some embodiments, compounds contain chemical groups having heteroatoms. Heteroatom-containing hydrocarbyl groups are molecular fragments in which one or more carbon atoms is replaced with an atom other than carbon, e.g., nitrogen, oxygen, sulfur, phosphorus or silicon. For example, the term "heteroalkyl" refers to an alkyl substituent that is heteroatom-containing, the term "heterocyclic" refers to a cyclic substituent that is heteroatom-containing, the term "heteroaryl" refers to an aryl substituent that is heteroatom-containing, and the like.

The terms "alkyl" and "Alk" refer to a straight- or branched-chain alkyl group having from 1 to about 20 carbon atoms in the chain. For example, the alkyl group can be a $(C_1-C_{20})$alkyl, a $(C_1-C_{12})$alkyl, $(C_1-C_8)$alkyl, $(C_1-C_6)$ alkyl, or $(C_1-C_4)$alkyl. Examples of alkyl groups include methyl (Me), ethyl (Et), n-propyl, isopropyl, butyl, isobutyl, sec-butyl, tert-butyl (t-Bu), pentyl, isopentyl, tert-pentyl, hexyl, isohexyl, and groups that in light of the ordinary skill in the art and the teachings provided herein would be considered equivalent to any one of the foregoing examples. Alkyl groups can be optionally substituted or unsubstituted, and optionally partially unsaturated, such as in an alkenyl group.

The term "cycloalkyl" refers to cyclic alkyl groups of, for example, from 3 to 10 carbon atoms having a single cyclic ring or multiple condensed rings. Cycloalkyl groups include, by way of example, single ring structures such as cyclopropyl, cyclobutyl, cyclopentyl, cyclooctyl, and the like, or multiple ring structures such as adamantyl, pinenyl, and the like. The cycloalkyl group can be monovalent or divalent, and can be optionally substituted, for example, by one or more alkyl groups. The cycloalkyl group can optionally include one or more cites of unsaturation, for example, the cycloalkyl group can include one or more carbon-carbon double bonds, such as, for example, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and the like.

The term "alkoxy" refers to the group alkyl-O—, where alkyl is as defined herein. Preferred alkoxy groups include, e.g., methoxy, ethoxy, n-propoxy, iso-propoxy, n-butoxy, tert-butoxy, sec-butoxy, n-pentoxy, n-hexoxy, 1,2-dimethylbutoxy, and the like.

The term "heteroaryl" refers to a monocyclic, bicyclic, or tricyclic ring system containing one, two, or three aromatic rings and containing at least one nitrogen, oxygen, or sulfur atom in an aromatic ring. The heteroaryl can be unsubstituted or substituted, for example, with one or more, and in particular one to three, substituents, as described in the definition of "substituted". Typical heteroaryl groups contain 2-20 carbon atoms in the ring skeleton in addition to the one or more heteroatoms.

Examples of heteroaryl groups include, but are not limited to, 2H-pyrrolyl, 3H-indolyl, 4H-quinolizinyl, acridinyl, benzo[b]thienyl, benzothiazolyl, β-carbolinyl, carbazolyl, chromenyl, cinnolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrimidinyl, pyrrolyl, quinazolinyl, quinolyl, quinoxalinyl, thiadiazolyl, thianthrenyl, thiazolyl, thienyl, triazolyl, tetrazolyl, and xanthenyl. In one embodiment the term "heteroaryl" denotes a monocyclic aromatic ring containing five or six ring atoms containing carbon and 1, 2, 3, or 4 heteroatoms independently selected from non-peroxide oxygen, sulfur, and N(Z) wherein Z is absent or is H, O, alkyl, aryl, or $(C_1-C_6)$alkylaryl. In some embodiments, heteroaryl denotes an ortho-fused bicyclic heterocycle of about eight to ten ring atoms derived therefrom, particularly a benz-derivative or one derived by fusing a propylene, trimethylene, or tetramethylene diradical thereto.

The heteroaryl can optionally be substituted with one or more alkyl, alkenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyannato, sulfamoyl, sulfinamoyl, sulfino, sulfo, sulfoamino, thiosulfo, $NR^xR^y$ and/or $COOR^x$, wherein each $R^x$ and $R^y$ are independently H, alkyl, alkenyl, aryl, heteroaryl, heterocycle, cycloalkyl, or hydroxy. For example, the nitrogen of any indolyl ring can be N-substituted to provide an N-alkyl, N-methyl, or N-protecting group indolyl compound. A heteroaryl can also be substituted with a substituent as described in the substituents definition below.

The term "heterocycle", "heterocyclyl", or "heterocycoalkyl" refers to a saturated or partially unsaturated ring system, containing at least one heteroatom selected from the group oxygen, nitrogen, and sulfur, and optionally substituted with alkyl, or $C(=O)OR^b$, wherein $R^b$ is hydrogen or alkyl. Typically, the heterocycle is a monocyclic, bicyclic, or tricyclic group containing one or more heteroatoms selected from the group oxygen, nitrogen, and sulfur. A heterocycle group also can contain an oxo group (=O) attached to the ring. Non-limiting examples of heterocycle groups include 1,3-dihydrobenzofuran, 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholine, piperazinyl, piperidine, piperidyl, pyrazolidine, pyrazolidinyl, pyrazolinyl, pyrrolidine, pyrroline, quinuclidine, and thiomorpholine. The heterocycle can optionally be a divalent radical, thereby providing a heterocyclene.

The heterocycle can optionally be substituted with one or more alkyl, alkenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyannato, sulfamoyl, sulfinamoyl, sulfino, sulfo, sulfoamino, thiosulfo, $NR^xR^y$ and/or $COOR^x$, wherein each $R^x$ and $R^y$ are independently H, alkyl, alkenyl, aryl, heteroaryl, heterocycle, cycloalkyl, or hydroxy. A heterocycle can also be substituted with a substituent as described in the substituents definition below.

Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles.

Protecting Groups. Compounds of the invention can further include one or more suitable protecting groups. The term "protecting group" refers to any group that, when bound to an sp-center, a hydroxyl, nitrogen, or other heteroatom prevents undesired reactions from occurring at this group and that can be removed by conventional chemical or enzymatic steps to reestablish the 'unprotected' moiety, such as an alkyne, hydroxyl, nitrogen, or other heteroatom group. The particular removable group employed is often interchangeable with other groups in various synthetic routes. Certain removable protecting groups include conventional substituents such as, for example, allyl, benzyl, acetyl, chloroacetyl, thiobenzyl, benzylidine, phenacyl, methyl methoxy, silicon protecting groups ("silyl ethers") (e.g., trimethylsilyl (TMS), t-butyl-diphenylsilyl (TBDPS), triisopropylsilyl (TIPS), or t-butyldimethylsilyl (TBS)) and any other group that can be introduced chemically onto a hydroxyl or other moiety and later selectively removed either by chemical or enzymatic methods in mild conditions compatible with the nature of the product.

A large number of protecting groups and corresponding chemical cleavage reactions are described in *Protective Groups in Organic Synthesis*, Theodora W. Greene (John Wiley & Sons, Inc., New York, 1991, ISBN 0-471-62301-6) ("Greene", which is incorporated herein by reference in its entirety). Greene describes many nitrogen protecting groups, for example, amide-forming groups. In particular, see Chapter 1, Protecting Groups: An Overview, pages 1-20, Chapter 2, Hydroxyl Protecting Groups, pages 21-94, Chapter 4, Carboxyl Protecting Groups, pages 118-154, and Chapter 5, Carbonyl Protecting Groups, pages 155-184. See also Kocienski, Philip J.; *Protecting Groups* (Georg Thieme Verlag Stuttgart, New York, 1994), which is incorporated herein by reference in its entirety. Some specific protecting groups that can be employed in conjunction with the methods of the invention are discussed below.

The term "halogen" refers to chlorine, fluorine, bromine or iodine. The term "halo" refers to chloro, fluoro, bromo or iodo.

As to any of the groups or "substituents" described herein (e.g., groups $R_1$, $R_2$, $R_3$, $R_4$, $R_5$, etc., each can further include one or more (e.g., 1, 2, 3, 4, 5, or 6) substituents. It is understood, of course, that such groups do not contain any substitution or substitution patterns which are sterically impractical and/or synthetically non-feasible.

The term "substituted" means that a specified group or moiety can bear one or more (e.g., 1, 2, 3, 4, 5, or 6) substituents such as one or more of the following substituents recited in this paragraph. The term "unsubstituted" means that the specified group bears no substituents. The term "optionally substituted" means that the specified group is unsubstituted or substituted by one or more substituents, and elements of the Formulas described herein can be optionally substituted. Where the term "substituted" is used to describe a structural system, the substitution is meant to occur at any valency-allowed position on the system. In cases where a specified moiety or group is not expressly noted as being optionally substituted or substituted with any specified substituent, it is understood that such a moiety or group is intended to be unsubstituted in some embodiments but can be substituted in other embodiments. In other words, variables such as $R_1$, $R_2$, and $R_3$ (etc.) and their elements can be optionally substituted. In various embodiments, suitable substituent groups (e.g., on groups $R_1$, $R_2$, and $R_3$ and/or their elements) include one or more of alkyl, alkenyl, alkynyl, alkoxy, halo, haloalkyl, hydroxy, hydroxyalkyl, aryl, aroyl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, arylsulfinyl, arylsulfonyl, heteroarylsulfinyl, heteroarylsulfonyl, heterocyclesulfinyl, heterocyclesulfonyl, phosphate, sulfate, hydroxyl amine, hydroxyl (alkyl)amine, and/or cyano. Additionally, suitable substituent groups can be, e.g., —X, —R, —OH, —OR, —SR, —S⁻, —NR$_2$, —NR$_3$, =NR, —CX$_3$, —CN, —OCN, —SCN, —N=C=O, —NCS, —NO, —NO$_2$, =N$_2$, —N$_3$, NC(=O)R, —C(=O)R, —C(=O)NRR, —S(=O)$_2$H, —S(=O)$_2$OH, —S(=O)$_2$R, —OS(=O)$_2$OR, —S(=O)$_2$NHR, —S(=O)R, —C(=O)R, —C(=O)X, —C(S)R, —C(O)OR, —C(O)O⁻, —C(S)OR, —C(O)SR, —C(S)SR, —C(O)NRR, —C(S)NRR, or —C(NR)NRR, where each X is independently a halogen ("halo"): F, Cl, Br, or I; and each R is independently H, alkyl, aryl, (aryl)alkyl (e.g., benzyl), heteroaryl, (heteroaryl)alkyl, heterocycle, heterocycle(alkyl), or a protecting group. As would be readily understood by one skilled in the art, when a substituent is keto (=O) or thioxo (=S), or the like, then two hydrogen atoms on the substituted atom are replaced. In certain embodiments, any one of the above groups can be included or excluded from a variable (e.g., groups $R^2$ and $R^3$) or from a group of substituents.

The term "pharmaceutically acceptable salts" refers to ionic compounds, wherein a parent non-ionic compound is modified by making acid or base salts thereof. Examples of pharmaceutically acceptable salts include, mineral or organic acid salts of basic residues such as amines; alkali or organic salts of acidic residues such as carboxylic acids; and the like. The pharmaceutically acceptable salts include conventional non-toxic salts and quaternary ammonium salts of the parent compound formed, for example, from non-toxic inorganic or organic acids. Non-toxic salts can include those derived from inorganic acids such as hydrochloric, hydrobromic, hydroiodic, sulfuric, sulfamic, phosphoric, nitric and the like. Salts prepared from organic acids can include those such as acetic, 2-acetoxybenzoic, ascorbic, behenic, benzenesulfonic, benzoic, citric, ethanesulfonic, ethane disulfonic, formic, fumaric, gentisinic, glucaronic, gluconic, glutamic, glycolic, hydroxymaleic, isethionic, isonicotinic, lactic, maleic, malic, mesylate or methanesulfonic, oxalic, pamoic (1,1'-methylene-bis-(2-hydroxy-3-naphthoate)), pantothenic, phenylacetic, propionic, salicylic, sulfanilic, toluenesulfonic, stearic, succinic, tartaric, bitartaric, and the like. Certain compounds can form pharmaceutically acceptable salts with various amino acids. For a review on pharmaceutically acceptable salts, see, e.g., Berge et al., *J. Pharm. Sci.* 1977, 66(1), 1-19, which is incorporated herein by reference.

The pharmaceutically acceptable salts of the compounds described herein can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of many suitable salts are found in *Remington: The Science and Practice of Pharmacy*, 21$^{st}$ edition, Lippincott, Williams & Wilkins, (2005).

The term "solvate" refers to a solid compound that has one or more solvent molecules associated with its solid structure. Solvates can form when a solid compound is crystallized from a solvent, wherein one or more solvent molecules become an integral part of the solid crystalline matrix. The compounds of the formulas described herein can be solvates, for example, ethanol solvates. Another type of a solvate is a hydrate. A "hydrate" likewise refers to a solid compound that has one or more water molecules intimately associated with its solid or crystalline structure at the molecular level. A hydrate is a specific type of a solvate. Hydrates can form when a compound is solidified or crystallized in water, wherein one or more water molecules become an integral part of the solid crystalline matrix. The compounds of the formulas described herein can be hydrates.

The term "diluent" refers to a pharmacologically inert substance that is nevertheless suitable for human consumption that serves as an excipient in the inventive dosage form. A diluent serves to dilute the API in the inventive dosage form, such that tablets of a typical size can be prepared incorporating a wide range of actual doses of the API.

The term "excipient" refers to an ingredient of the dosage form that is not medicinally active, but serves to dilute the API, assist in dispersion of the tablet in the patient's stomach, bind the tablet together, and serve other functions like stabilizing the API against decomposition.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect, such as an antifungal effect. For example, an effective amount can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat a disease or disorder, or to treat the symptoms of the disease or disorder, in a host. Thus, an "effective amount" generally means an amount that provides the desired effect.

The terms "treating", "treat" and "treatment" include (i) inhibiting the disease, pathologic or medical condition or arresting its development; (ii) relieving the disease, pathologic or medical condition; and/or (iii) diminishing symptoms associated with the disease, pathologic or medical condition. Thus, the terms "treat", "treatment", and "treating" can include lowering, stopping, or reversing the progression or severity of the condition or symptoms being treated.

The terms "inhibit", "inhibiting", and "inhibition" refer to the slowing, halting, or reversing the growth or progression of a disease, infection, condition, or group of cells, such as fungal cells. The inhibition can be greater than about 20%, 40%, 60%, 80%, 90%, 95%, or 99%, for example, compared to the growth or progression that occurs in the absence of the treatment or contacting.

Antifungal drugs include compounds of the formulas described herein, which can be used in combination with other antifungal drugs. A variety of antifungal drugs are known in the art, including imidazoles such as oxiconazole, clotrimazole, miconazole, sulconazole, and ketoconazole; allylamines such as naftifine and terbinafine, triazoles such as fluconazole and itraconazole; glucan synthase inhibitors such as cilofungin; chitin synthase inhibitors such as nikkomycin Z; polyenes such as amphotericin B, nystatin, and faeriefungin; griseofulvin; morpholine derivatives such as amorolfine; pyridones, pyridines or pyridinones such as ciclopirox olamine; triazines such as the pyrido[3,4-e]-1,2,4-triazines; pyrimidines such as flucytosine; and fungal cell wall disruptors such as echinocandin B. In various embodiments, specific examples of useful antifungal compounds for combination therapy include amorolfine, amphotericin (e.g., amphotericin B), anidulafungin, caspofungin, ciclopirox, clotrimazole, econazole, fluconazole, flucytosine, itraconazole, ketoconazole, micafungin, miconazole, naftifine, oxiconazole, posaconazole, terbinafine, terconazole, saperconazole, and voriconazole.

Various Embodiments

In various embodiments, the compounds of Formula I can be compounds of Formula IB wherein Ring A and Ring B of Formula I are phenyl groups:

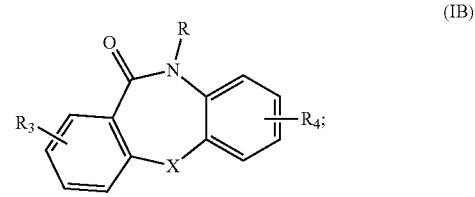

or the compounds of Formula I can be compounds of Formula IC wherein one or both of Ring A and Ring B of Formula I are pyridyl groups, for example, as in Formula IC:

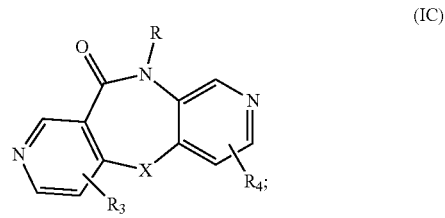

which compounds can be readily prepared by using the corresponding pyridyl groups in place of the substituted phenyl groups in the preparation of the heterocycle, as described below in Scheme 1 of Example 1. Compounds of Formula IA are specific examples of the compounds of Formula IB and IC.

The compounds of Formula I, IA, and IB can include a variety of lipophilic groups as substituents, which groups enhance the cell wall or membrane penetration by the compounds.

For example, the invention includes a compound of Formula IA:

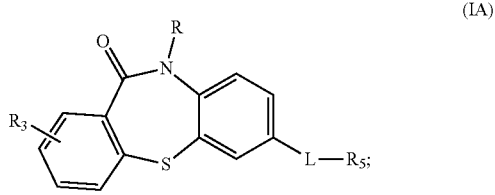

Figure 11:
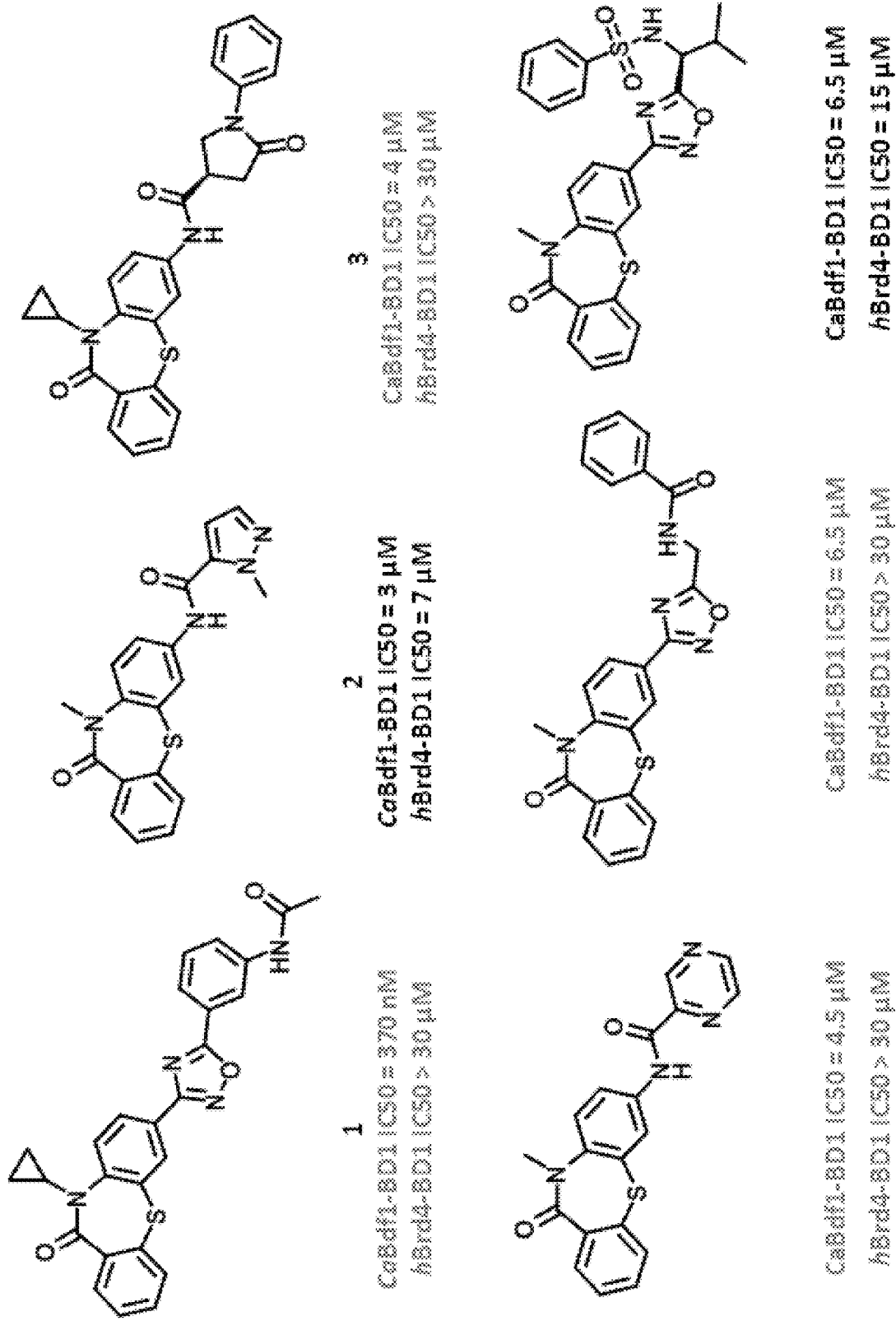
FIG. 11. Dibenzothiazepinone compounds showing selectivity for CaBdf1 BD1 over human Brd4-BD1.
Figure 11:
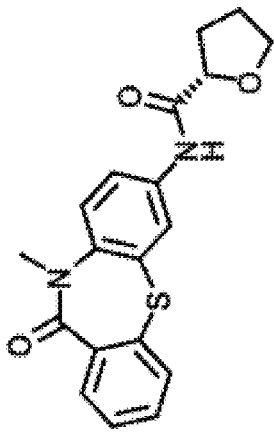
Figure 11:
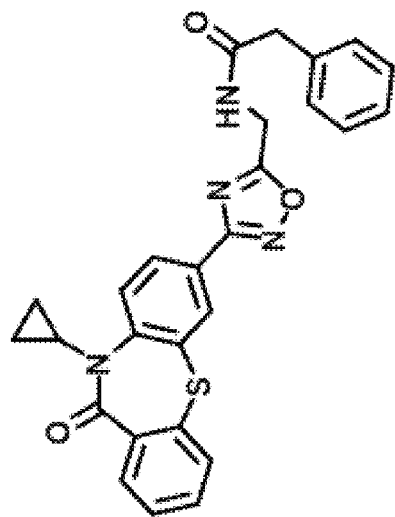
Figure 11:
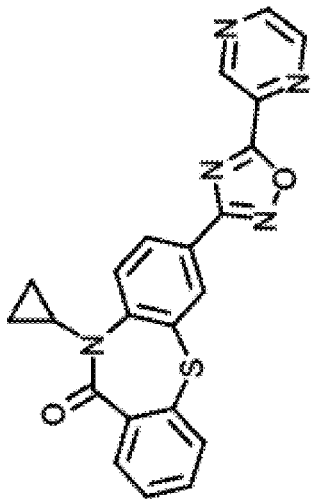
Figure 11:
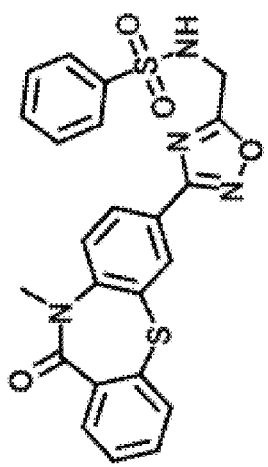

(IA)

wherein -L-R$_5$ is substituted or non-substituted aryl, substituted or non-substituted heteroaryl, substituted or non-substituted heterocycloalkyl, —CH(R$_6$)-benzamide or —CH(R$_6$)-sulfonamide where R$_6$ is a straight-chain or branched C1-C8 alkyl, such as the groups shown in FIG. 11. In other embodiments, R$_5$ is C4-C18 alkyl, C4-C18 alkyl substituted with C3-C8 cycloalkyl, or ((CH$_2$)$_n$O)$_x$CH$_3$ where n is 2-4 and x is 1-4. Examples of such R$_5$ groups include t-butyl, hexyl, octyl, hexadecyl, ethyl-cyclopentyl, or a PEG group such as —(CH$_2$CH$_2$O)$_{1-4}$CH$_3$. Such R$_5$ groups are also examples of various R$_1$, R$_2$, R$_3$ and R$_4$ groups of Formulas II and III.

Compounds of Formula I can be linked to compounds of Formulas II or III via a linker Z. Linker Z can be anywhere from 1 to about 40 atoms in length (counted linearly), often about 1-30 atoms, about 1-20 atoms, or about 1-10 atoms in length. The chain can include 0, 1, 2, 3, 4, 5, 6, 7, or 8 heteroatoms, and the chain can be interrupted by 1 or 2 cycloalkyl, heterocycloalkyl, aryl, or heteroaryl groups, which groups can include an adjacent carbonyl or amide (—NC(=O)—) group to connect the group to the rest of the chain.

Accordingly, in one embodiment, the linker Z is a divalent radical of the formula -W-A-W- wherein each W is independently —N(R')C(=O)—, —C(=O)N(R')—, —OC(=O)—, —C(=O)O—, —O—, —S—, —S(O)—, —S(O)$_2$—, —N(R')—, —C(=O)—, —(CH$_2$)$_n$— where n is 1-3, or a direct bond; wherein each R' is independently H, (C$_1$-C$_6$)alkyl, or a nitrogen protecting group; and A is (C$_1$-C$_{16}$)alkyl, (C$_2$-C$_{16}$)alkenyl, (C$_2$-C$_{16}$)alkynyl, (C$_3$-C$_8$) cycloalkyl, heterocycloalkyl, heteroaryl (such as 3,5-oxadiazolyl), (C$_6$-C$_{10}$)aryl, —NH—, —(OCH$_2$—CH$_2$)$_n$— where n is 1 to about 10, —C(O)NH(CH$_2$)$_n$ wherein n is 1 to about 6, or (C$_1$-C$_{20}$)alkyl, (C$_2$-C$_{16}$)alkenyl, (C$_2$-C$_{16}$)alkynyl, or —(OCH$_2$—CH$_2$)$_n$— interrupted between two carbons, or between a carbon and an oxygen, with a (C$_3$-C$_8$)cycloalkyl, heterocycloalkyl, heteroaryl, or (C$_6$-C$_{10}$)aryl group.

For example, Z can be NH (where each W is a direct bond and A is NH) or —NH-A-C(=O)—NH— where A is phenyl, heterocycloalkyl, or heteroaryl (where one W is NH and the other W is C(=O)—NH—), or Z can be —NH-Ph-C(=O)—NH— (where A is phenyl, a (C$_6$-C$_{10}$)aryl). The linker Z can also be a PEG group, such as when A is —(OCH$_2$—CH$_2$)$_n$— where n is 1 to about 10, in which case one or both W groups are often a carbonyl or amide.

The compounds of Formula III can be prepared by installing the appropriate substituents to an imidazothiadiazole core, which core can be prepared as described by PCT Publication No. WO 2012/020215 (Pastor Fernández et al.), which describes the synthesis of the imidazothiadiazole core and displacement of a bromo group with a relevant alkyl amine such as a piperidine. Various methods to replace the iodo of Pastor Fernández with an "amino" equivalent, such as tert-butylamine (e.g., by the Ullmann or Buchwald-Hartwig chemistry) can be carried out by the methods described at www.organic-chemistry.org/synthesis/C1N/amines/arylamines.shtm. Further modifications can include removal of a tert-butylamine with triflic acid (as described by Krasavin et al., *Tetrahedron Lett.* 2008, 49(51), 7318-7321). The aryl amine on the core can then be acylated with a carboxy-substituted pyrrole to provide a compound of Formula III.

In various embodiments, fungal infection can be treated by administering to a subject in need of antifungal treatment an effective amount of a compound of a formula described herein that inhibits one of the two bromodomains (BD1 or BD2). A second antifungal compound that inhibits the other bromodomain can also be administered, concurrently or sequentially, to enhance the effectiveness of the antifungal treatment. For example, compounds of Formula I (e.g., MS5) can be effective for inhibiting BD1, and compounds of Formula II (e.g., MS51) can be effective for inhibiting BD2, and compounds of these formulas can be administered together to therapeutically treat a bacterial infection.

Alternatively, one of the compounds of a formula described herein can be administered with a known antifungal drug, such as fluconazole or another antifungal drug recited herein, that is effective to inhibit the other bromodomain more effectively than the compound of a formula described herein. Thus, the compounds described herein can be BD1 inhibitors, and/or BD2 inhibitors. When the compounds are more effective for inhibiting one bromodomain than the other, a fungal infection can be treated by administering the BD1 inhibitor in conjunction with an antifungal compound that is a BD2 inhibitor, and vice versa. Additionally, the effectiveness of antifungal drugs that have decreased effectiveness due to resistance developed by a *Candida* sp. strain can be rendered significantly more effective by administering them with a BD2 inhibitor.

General Synthetic Methods

In general, preparation of the compounds and formulas described herein, and modifications thereof, can be made according to organic synthesis techniques known to those of skill in the art and/or according to the synthetic schemes provided herein. Where desired, synthesis of a subject compound can begin with commercially available chemicals, from compounds described in the chemical literature, or from products of the reactions and methods described herein. Commercially available compounds may be obtained from standard commercial sources including Acros Organics (Pittsburgh, Pa.), Aldrich Chemical (Milwaukee, Wis., including Sigma Chemical and Fluka), Eastman Organic Chemicals, Eastman Kodak Company (Rochester, N.Y.), Fisher Scientific Co. (Pittsburgh, Pa.), ICN Biomedicals, Inc. (Costa Mesa, Calif.), Lancaster Synthesis (Windham, N.H.), Spectrum Quality Product, Inc. (New Brunswick, N.J.), TCI America (Portland, Oreg.), Combi-Blocks, Inc. (San Diego, Calif.), Oakwood Products, Inc. (Estill, S.C.), and Wako Chemicals USA, Inc. (Richmond, Va.).

In addition, methods known to one of ordinary skill in the art may be identified through various reference books and databases. Suitable reference books and treatises that detail the synthesis of reactants useful in the preparation of the inhibiting agents described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992; and *Protecting Groups in*

*Organic Synthesis, Second Edition*, Greene, T. W., and Wutz, P. G. M., John Wiley & Sons, New York.

Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

A number of exemplary methods for preparation of the compounds of the invention are provided below. These methods are intended to illustrate the nature of such preparations are not intended to limit the scope of applicable methods. Other variations, such as adding various substituents (e.g., as defined above and herein) on various alkyl, aryl, or heterocycle groups are included in the scope of the invention. Relevant starting materials, substituents, and groups containing substituents, can typically be purchased from the commercial suppliers cited above (e.g., from Sigma-Aldrich, Milwaukee, Wis.) or they can be prepared in a few standard steps from commercially available materials. A number of useful techniques for prepping and/or installing substituents onto the core of a molecule are described by Hermanson in Bioconjugate Techniques (Greg T. Hermanson. Academic Press, San Diego, Calif. 1996).

Antifungal Formulations

In some embodiments, the compounds described herein can be prepared as pharmaceutical compositions. The pharmaceutical composition will typically contain a physiologically acceptable carrier or a pharmaceutically acceptable carrier. The compositions can also include a second antifungal drug, or an antifungal adjuvant, such as an essential oil or essential oil extract. Suitable oils and extracts that can be used in combination with the compounds described herein include the therapeutically-active substances described in PCT Publication No. WO 2006/120565 (Remmal), such as carveol, thymol, eugenol, borneol, carvacrol, alpha-ionone, beta-ionone, as well as isomers, derivatives, and mixtures thereof.

Although oral administration is a desired route of administration, other means of administration such as nasal, topical (for example, administration to the skin or eye) or rectal administration, or by injection or inhalation, are also contemplated. Depending on the intended mode of administration, the pharmaceutical compositions may be in the form of solid, semi-solid or liquid dosage forms, such as, for example, tablets, suppositories, pills, capsules, powders, liquids, suspensions, drops, ointments, creams or lotions, preferably in unit dosage form suitable for single administration of a precise dosage. The compositions may include an effective amount of a selected compound in combination with a pharmaceutically acceptable carrier and, in addition, may include other pharmaceutical agents such as various adjuvants, diluents, buffers, or other antiviral agents, and the like. The compound may thus be administered in dosage formulations containing conventional non-toxic pharmaceutically acceptable carriers, adjuvants and vehicles. The amount of active compound administered will be dependent on the subject being treated, the subject's weight, the manner of administration and the judgment of the prescribing physician.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions may, for example, be prepared by dissolving, dispersing, etc., an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan mono-laurate, triethanolamine acetate, triethanolamine oleate, etc. Actual methods of preparing such dosage forms are known, or will be apparent, to those skilled in this art.

For oral administration, the composition will generally take the form of a tablet or capsule, or may be an aqueous or non-aqueous solution, suspension or syrup. Tablets and capsules for oral use will generally include one or more commonly used carriers such as lactose and corn starch. Lubricating agents, such as magnesium stearate, are also typically added. When liquid suspensions are used, the active agent may be combined with emulsifying and suspending agents. If desired, flavoring, coloring and/or sweetening agents may be added as well. Other optional components for incorporation into an oral formulation herein include, but are not limited to, preservatives, suspending agents, thickening agents, and the like.

Accordingly, the compounds described herein can be used to prepare therapeutic pharmaceutical compositions, for example, by combining the compounds with a pharmaceutically acceptable diluent, excipient, or carrier. The compounds may be added to a carrier in the form of a salt or solvate. For example, in cases where compounds are sufficiently basic or acidic to form stable nontoxic acid or base salts, administration of the compounds as salts may be appropriate. Examples of pharmaceutically acceptable salts are organic acid addition salts formed with acids that form a physiologically acceptable anion, for example, tosylate, methanesulfonate, acetate, citrate, malonate, tartrate, succinate, benzoate, ascorbate, α-ketoglutarate, and β-glycerophosphate. Suitable inorganic salts may also be formed, including hydrochloride, halide, sulfate, nitrate, bicarbonate, and carbonate salts.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The compounds of the formulas described herein can be formulated as pharmaceutical compositions and administered to a mammalian host, such as a human patient, in a variety of forms. The forms can be specifically adapted to a chosen route of administration, e.g., oral or parenteral administration, by intravenous, intramuscular, topical or subcutaneous routes.

The compounds described herein may be systemically administered in combination with a pharmaceutically acceptable vehicle, such as an inert diluent or an assimilable edible carrier. For oral administration, compounds can be enclosed in hard or soft-shell gelatin capsules, compressed into tablets, or incorporated directly into the food of a patient's diet. Compounds may also be combined with one or more excipients and used in the form of ingestible tablets, buccal tablets, troches, capsules, elixirs, suspensions, syrups, wafers, and the like. Such compositions and preparations typically contain at least 0.1% of active compound. The percentage of the compositions and preparations can vary and may conveniently be from about 0.5% to about 60%, about 1% to about 25%, or about 2% to about 10%, of the weight of a given unit dosage form. The amount of active compound in such therapeutically useful compositions can be such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the active compound (i.e., an antifungal compound described herein) may be incorporated into sustained-release preparations and devices.

The active compound may be administered intravenously or intraperitoneally by infusion or injection. Solutions of the active compound or its salts can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the active ingredient adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and/or other antifungal agents, for example, parabens, chlorobutanol, phenol, sorbic acid, thimerosal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the active compound in the required amount in the appropriate solvent with various other ingredients enumerated above, as required, optionally followed by filter sterilization. In the case of sterile powders for the preparation of sterile injectable solutions, methods of preparation can include vacuum drying and freeze-drying techniques, which yield a powder of the active ingredient plus any additional desired ingredient present in the solution.

For topical administration, compounds may be applied in pure form, e.g., when they are liquids. However, it will generally be desirable to administer the active agent to the skin as a composition or formulation, for example, in combination with a dermatologically acceptable carrier, which may be a solid, a liquid, a gel, or the like. If desired, the topical formulation containing the antifungal drug may include a cyclodextrin such as hydroxypropyl-β-cyclodextrin to enhance the water-solubility of the antifungal drug.

Useful solid carriers include finely divided solids such as talc, clay, microcrystalline cellulose, silica, alumina, and the like. Useful liquid carriers include water, dimethyl sulfoxide (DMSO), alcohols, glycols, or water-alcohol/glycol blends, in which a compound can be dissolved or dispersed at effective levels, optionally with the aid of non-toxic surfactants. Adjuvants such as fragrances and additional antimicrobial agents (such as essential oils or essential oil extracts) can be added to optimize the properties for a given use. The resultant liquid compositions can be applied from absorbent pads, used to impregnate bandages and other dressings, or sprayed onto the affected area using a pump-type or aerosol sprayer.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Examples of dermatological compositions for delivering active agents to the skin are known to the art; for example, see U.S. Pat. No. 4,992,478 (Geria), U.S. Pat. No. 4,820,508 (Wortzman), U.S. Pat. No. 4,608,392 (Jacquet et al.), and U.S. Pat. No. 4,559,157 (Smith et al.). Such dermatological compositions can be used in combinations with the compounds described herein where an ingredient of such compositions can optionally be replaced by a compound described herein, or a compound described herein can be added to the composition.

Useful dosages of the compounds described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a compound, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician.

A suitable dose can be in the range of from about 0.5 to about 100 mg/kg, e.g., from about 10 to about 75 mg/kg of body weight per day, such as 3 to about 50 mg per kilogram body weight of the recipient per day, in the range of 6 to 90 mg/kg/day, or in the range of 15 to 60 mg/kg/day.

A compound described herein can be conveniently formulated in unit dosage form; for example, containing 5 to 1000 mg, about 10 to 750 mg, or about 50 to 500 mg of active ingredient per unit dosage form. In one embodiment, the invention provides a composition comprising a compound formulated in such a unit dosage form. The desired dose may be presented in a single dose or as divided doses administered at appropriate intervals, for example, as two, three, four or more sub-doses per day. The sub-dose itself may be further divided, e.g., into a number of discrete loosely spaced administrations, such as multiple inhalations from an insufflator or by application of a plurality of drops into the eye.

The invention provides therapeutic methods of treating a fungal infection in a mammal, which involve administering to a mammal having a fungal infection an effective amount of a compound or composition described herein. A mammal includes a primate, human, rodent, canine, feline, bovine, ovine, equine, swine, caprine, bovine and the like.

The ability of a compound of the invention to treat a fungal infection may be determined by using assays well known to the art. For example, the design of treatment protocols, toxicity evaluation, data analysis, and quantification of fungal cell kill are well known in the art.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

Example 1. Anti-Fungal Compound Screening and Evaluation

Invasive fungal infections are a major cause of mortality and morbidity among immunocompromised individuals. However, the limited number of anti-fungal drugs and the increasing prevalence of drug-resistant strains pose an urgent need for new therapeutic strategies. Bromodomain factor 1 (BDF1) is a fungal transcription factor of the Bromo and Extra-Terminal domain (BET) family, in *Candida albicans*, a widespread nosocomial pathogen. BDF1 was investigated as described herein. The results of the investigation indicate that BDF1 is essential in *C. albicans* and that mutations which inactivate BDF1 bromodomains lead to a loss of viability in vitro and to decreased pathogenesis in a mouse model of candidiasis.

Structural analysis and resistance to human BET inhibitors reveal pronounced differences between the ligand-binding pockets of Bdf1 and human BET bromodomains. Chemical screening identified small-molecule compounds which inhibit the acetylpeptide binding activity of *C. albicans* Bdf1 with up to around 100-fold selectivity over human BET bromodomains, including compounds which phenocopy the effects of Bdf1 bromodomain-inactivating mutations. Selectivity is due to active-site residues which in Bdf1 have short side chains compatible with inhibitor binding and which correspond to bulkier residues that sterically hinder inhibitor binding in human BET proteins. These findings demonstrate the potential of epigenetic reader domain inhibition as a novel anti-fungal strategy and identify Bdf1 bromodomains as a promising new chemotherapeutic target that can be selectively inhibited without antagonizing human BET function.

Invasive fungal infections are a major global health concern, with up to two million cases estimated annually worldwide[1]. Candidemia, cryptococcal meningitis, invasive aspergillosis and *pneumocystis* pneumonia are collectively estimated to cause over 800,000 deaths per year [ref.[2] and references therein]. *Candida* species are by far the major nosocomial pathogens, with a mortality rate of 30-40%. Among *Candida* species, *C. albicans* and *C. glabrata* rank first and second in isolation frequency, respectively, and together are responsible for approximately 70% of all systemic candidiasis[3]. The high hospital costs for patients with candidemia imply a considerable pharmacoeconomic burden[4]. Current therapeutic strategies to fight invasive fungal infections either target fungal cell membrane integrity (polyene drugs), or inhibit the synthesis of ergosterol (azoles), nucleic acids (flucytosine) or the fungal cell wall (echinocandins)[5]. The emergence of acquired drug resistance by many fungal strains, and the toxicity, high cost, and narrow activity spectrum of the limited repertoire of available drugs has led to an urgent need for novel therapeutic agents.[1, 6, 7, 8, 9]

To date, a small number of chromatin proteins have been investigated as possible anti-fungal targets[10]. Histone deacetylase (HDAC) inhibitors have weak anti-fungal activity when used alone, but synergize with other anti-fungal agents, such as azoles and echinocandins[11-14]. A recent study investigated the KIX domain of the Mediator complex subunit Med15, which interacts with pleiotropic drug resistance transcription factor (Pdr1) in *Candida glabrata*[15]. An inhibitor targeting the KIX domain-Pdf1 interface re-sensitized drug-resistant strains to existing antifungals. In the present study, we investigate an epigenetic reader domain, the bromodomain (BD) from the BET (bromo- and extra-terminal domain) family, as a potentially novel anti-fungal target.

Figure 3:
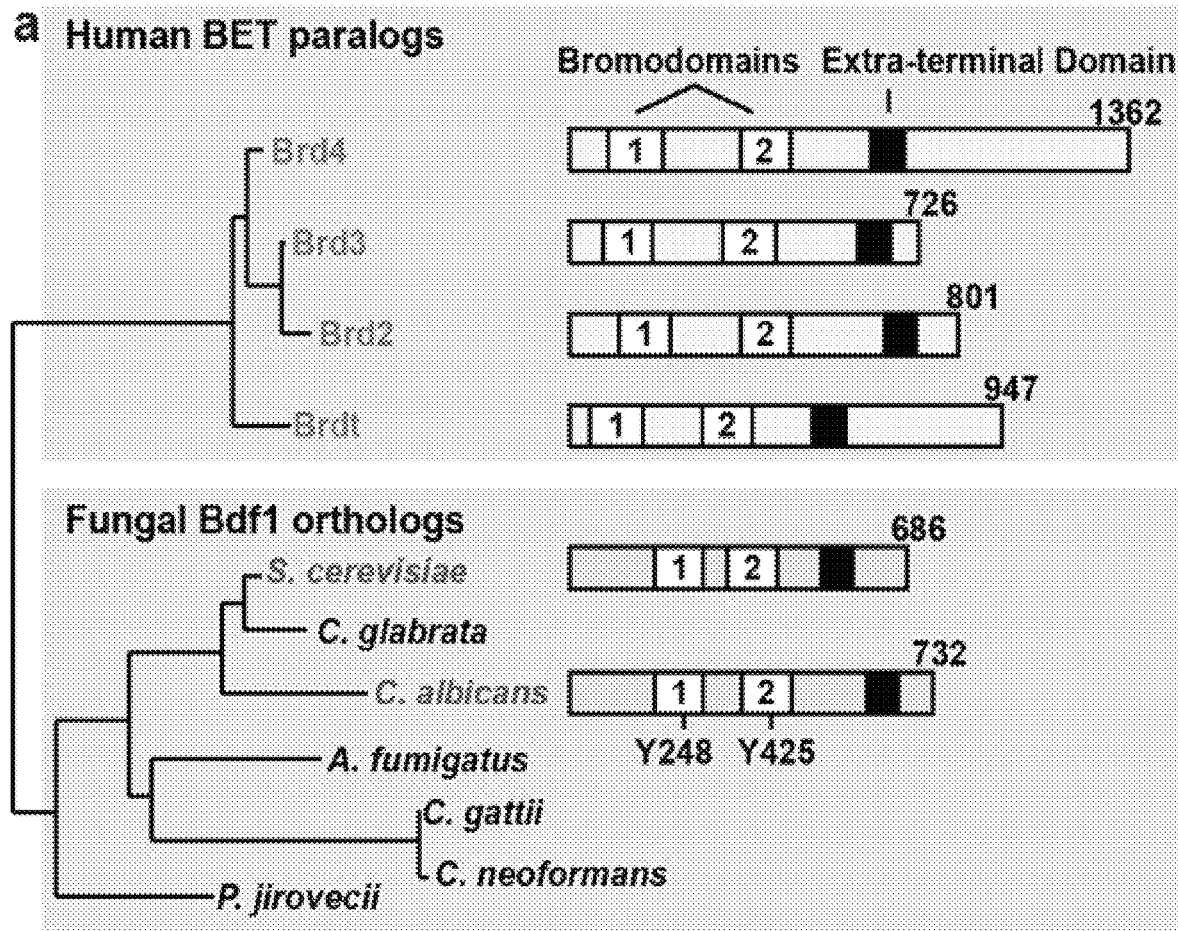
FIG. 3. C. albicans Bdf1 bromodomains are specific for multi-acetylated histone H4 tails. (a) Phylogeny and domain organization of fungal Bdf1 and human BET orthologs. (b) Binding of wildtype and mutant CaBdf1 bromodomains to an array of 384 histone peptides. The array comprised control peptides (gray background) or N-terminal peptides derived from histones H3, H4, H2A and H2B (magenta, cyan, pink and green background, respectively) bearing between 0 and 4 post-translational modifications, including methyl, citrulline, phosphoryl and acetyl marks. Signals corresponding to background and positive binding controls (green), H4 (magenta) and H4ac4 peptides (blue) are boxed and shown at higher magnification below the array. The assay was performed in duplicate. (c). Summary of binding data for acetylated H4 peptides. H4 peptides (cyan rectangles) spanning residues 1-19 or 11-30 bore between 0 and 4 acetyl marks at residues K5, K8, K12, K16 or K20 (black boxes). Binding intensity is normalized to the intensity of the positive control. Both BDs bound to multi-acetylated peptides more tightly than to mono- and unacetylated peptides, while binding was abolished when the conserved Tyr residues implicated in ligand recognition were mutated to Phe. (d) Pull-down assay. Histone H4 N-terminal peptides in their unmodified (H4) or tetra-acetylated (H4ac4) form were immobilized and incubated with wildtype GST-tagged CaBdf1 bromodomains or with the corresponding constructs bearing the inactivating Tyr to Phe substitution. After washing, bound proteins were eluted and visualized in a Western blot using an anti-GST antibody.
Figure 3:
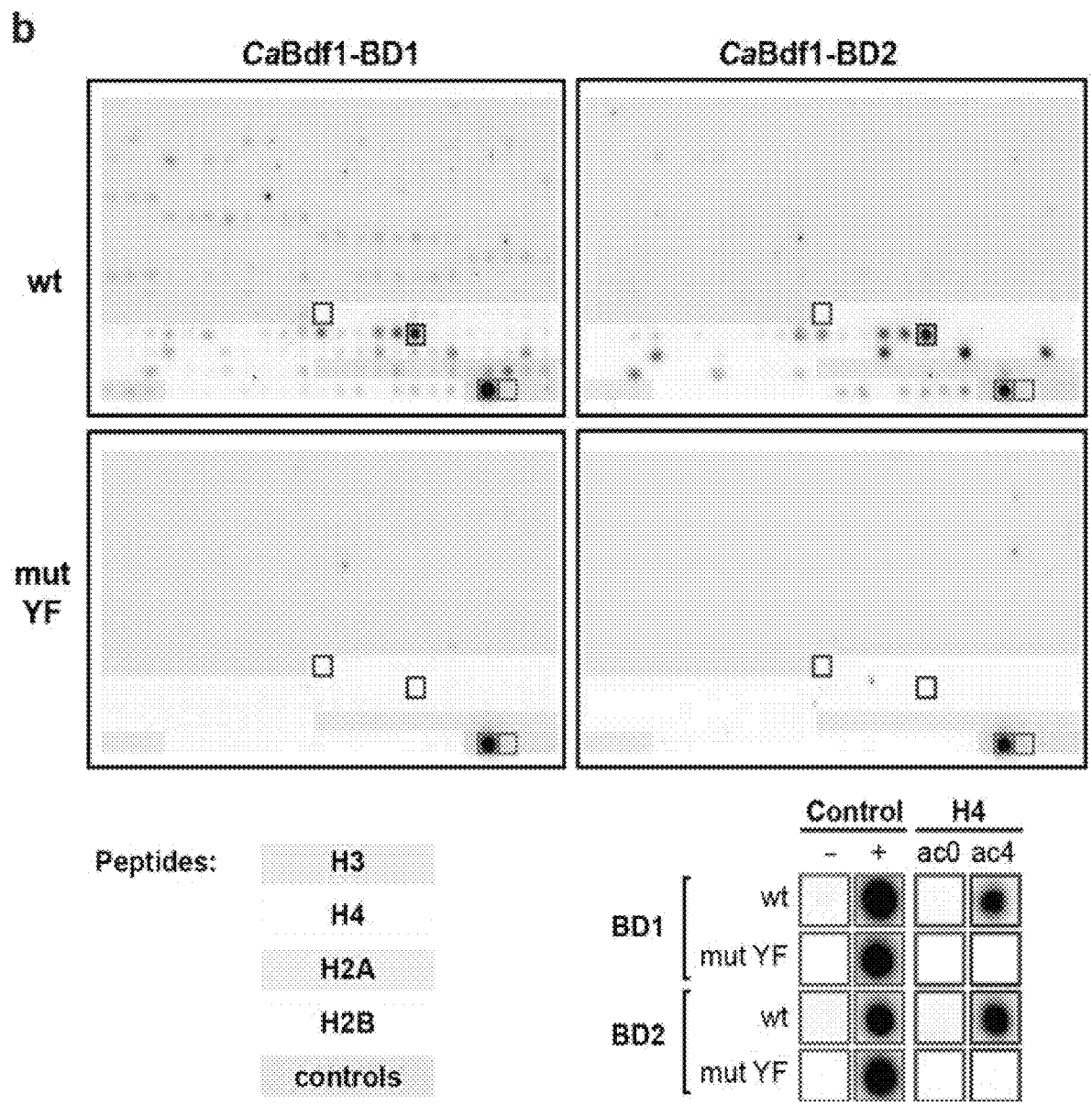
Figure 3:
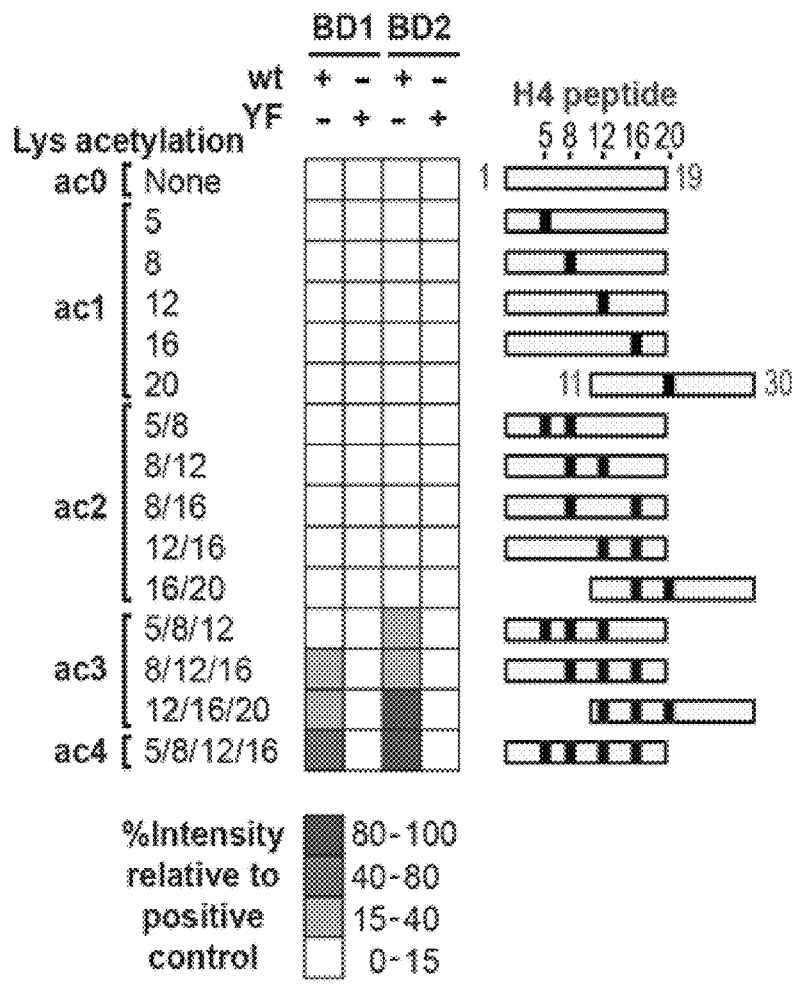
Figure 3:
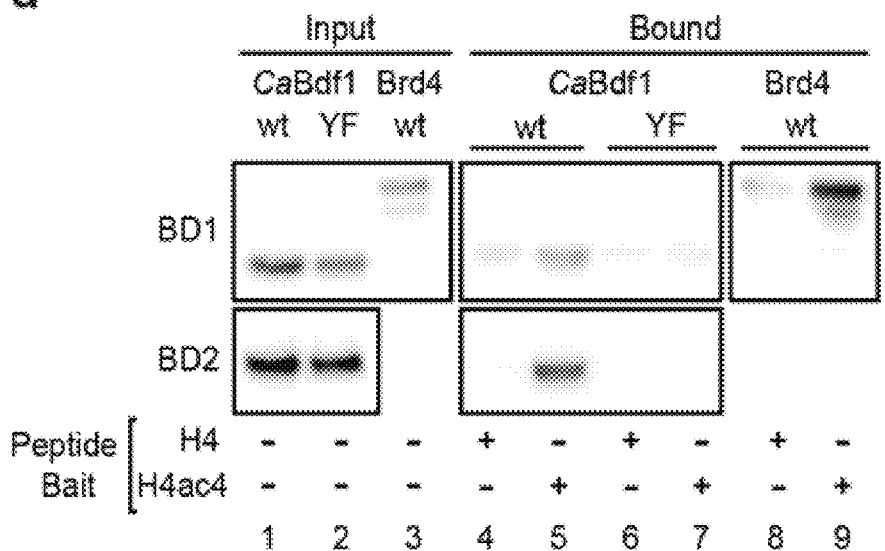

BET proteins are chromatin-associated factors that regulate gene transcription and chromatin remodeling[16]. Human members of this family are Brd2, Brd3, Brd4 and Brdt (FIG. 3a). BET proteins bind chromatin through their two bromodomains (BD1 and BD2), small helical domains which specifically recognize histones acetylated on lysine residues. Whereas canonical bromodomains bind mono-acetylated histone peptides, BET bromodomains possess a wider ligand binding pocket that allows them to recognize diacetylated histone peptides[17,18]. Small-molecule inhibitors such as JQ1 and I-BET which selectively target BET bromodomains have been used to validate BET bromodomain inhibition as a therapeutic strategy against cancer and other medical conditions[16,19-22].

The fungal BET protein Bdf1 has been characterized as a global transcriptional regulator in the budding yeast *S. cerevisiae*. Bdf1 associates with acetylated histones H3 and H4[23,24] and with the general transcription factor TFIID[25], regulates the transcription of over 500 genes[23], is a subunit of the SWR1 chromatin remodeling complex that mediates euchromatin maintenance and antisilencing[26] and is important for chromatin compaction during sporulation[27] and for the salt stress response[28]. In addition to BDF1, *S. cerevisiae* possesses a second BET family gene, BDF2, which is partly functionally redundant with BDF1[25,29,30].

Disruption of BDF1 causes severe morphological and growth defects, while deletion of both BDF1 and BDF2 is lethal[23,24,31-33]. Point mutations that abolish ligand binding by Bdf1 bromodomains BD1 and BD2 cause growth defects and affect the majority of transcripts altered by disruption of the entire gene[23]. Many pathogenic fungi, including *C. albicans*, lack BDF2, raising the possibility that bromodomain inhibition of the sole BET family protein Bdf1 might significantly reduce viability and virulence.

Results.

Bdf1 BD Functionality is Essential in *C. albicans*.

To investigate Bdf1 BD function in *C. albicans*, we first verified the ligand-binding activity of the individual domains. A histone peptide array showed that both BD1 and BD2 recognize multi-acetylated forms of histone H4 (FIG. 3*b*, 3*c*), exhibiting highest affinity for an H4 peptide tetra-acetylated on lysines 5, 8, 12 and 16 (hereafter denoted H4ac4). H4ac4 peptide recognition by both BDs was confirmed in a pull-down assay (FIG. 3*d*). We replaced a conserved tyrosine residue in the ligand binding pocket of each BD by phenylalanine, a mutation known to compromise ligand binding activity in other BET proteins[23]. These two "YF" mutations (Y248F and Y425F) abolished binding to acetylated H4 peptides (FIG. 3*b-d* and FIG. 4*b*, 4*c*), confirming the specificity of peptide recognition. Unlike human BET proteins, in which the two BDs recognize different histone acetylpeptides, the above results reveal the two BDs of CaBdf1 to have similar ligand-binding selectivity, suggesting a certain degree of redundancy between these two domains.

It was next asked whether CaBdf1 BD function was important for the viability of *C. albicans*, an obligate diploid. We generated a heterozygous deletion mutant for BDF1 in strain SC5314, but were unable to obtain a homozygous deletion mutant, indicating that BDF1 is an essential gene (the heterozygous strain showed no significant phenotype). To verify essentiality we used a conditional promoter to control Bdf1 expression from the second allele. Two approaches were used, involving either a methionine-sensitive promoter or a newly engineered tetracycline-regulated cassette.

Figure 4:
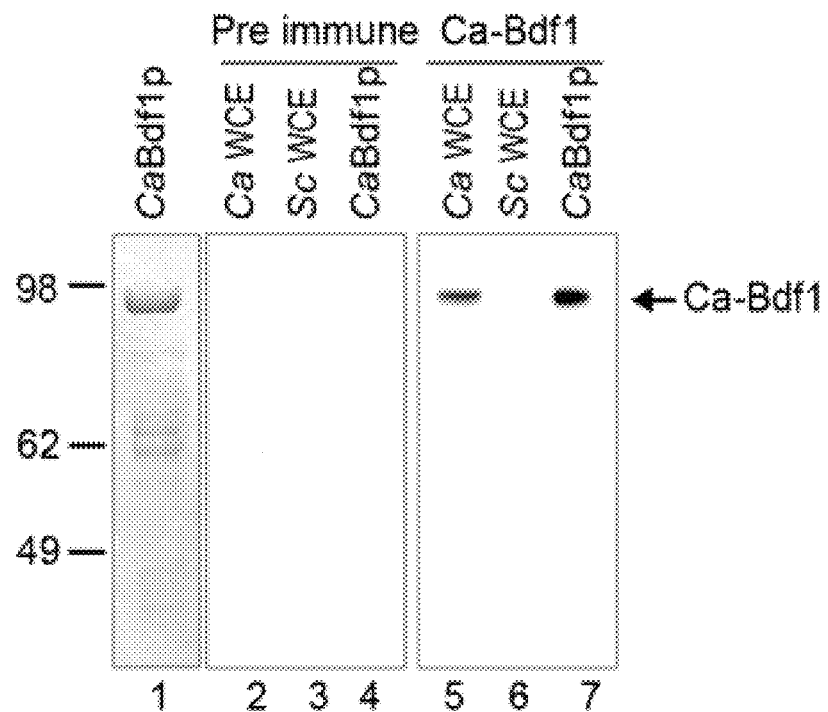
FIG. 4. BET bromodomain conservation and development of anti-CaBdf1 antibody. (a) Percent identity of BET bromodomains among human and fungal BET proteins. (b) Location of the YF point mutations used in this study. (c) Development of an antibody specific to C. albicans Bdf1. A band of the expected molecular weight is specifically detected after immunization of the rabbit. (d) Validation of antibody specificity. The antibody detected a shifted band when Bdf1 was TAP-tagged, whereas the signal was lost when Bdf1 was not expressed.
Figure 4:
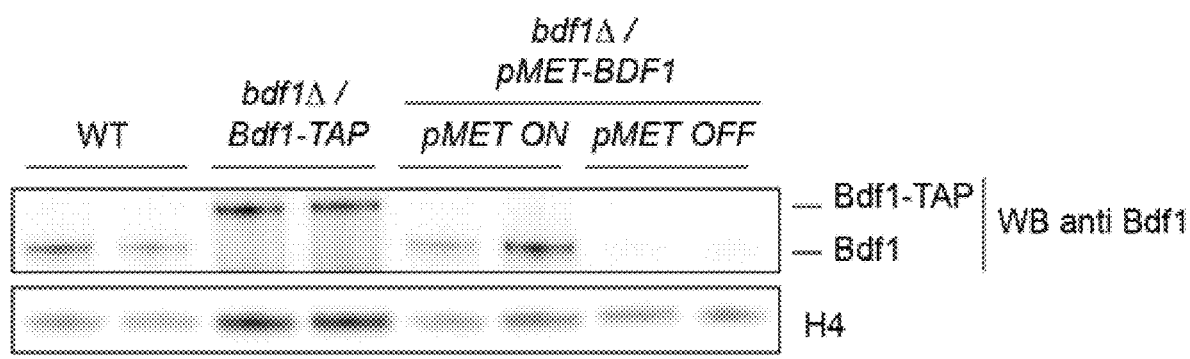
Figure 5:
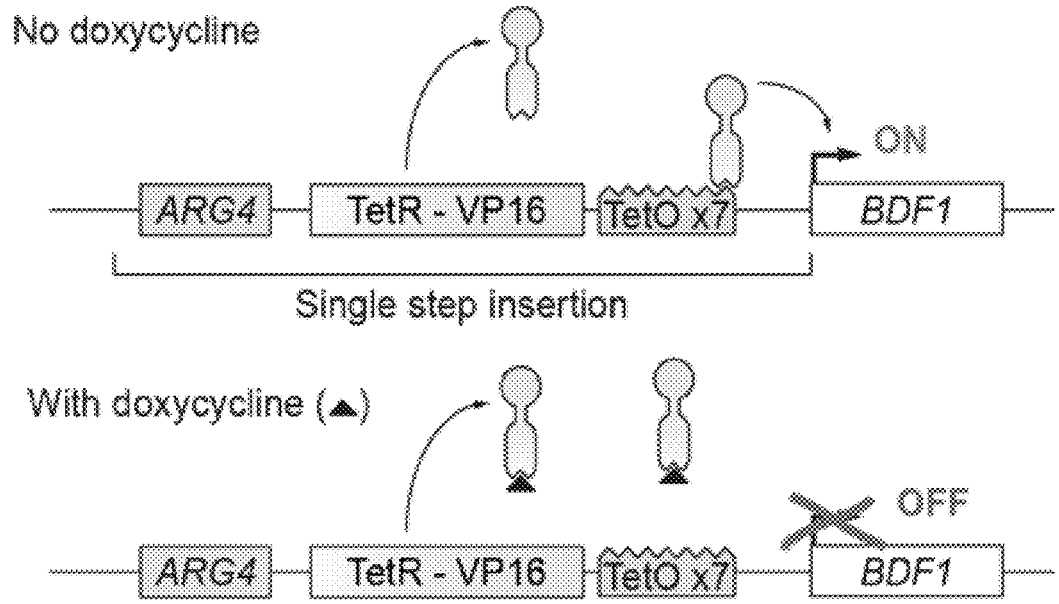
FIG. 5. Bdf1 bromodomains are essential for viability of C. albicans. (a) Schematic of the one-step Tet-OFF construct used in this study. The construct contains an auxotrophic marker (ARG4), the gene encoding the fusion Tet activator (TetR-VP16) and seven tandem repeats of the TetO operator upstream of the BDF1 ORF. Dox inhibits the binding of TetR-VP16 to TetO, preventing transcription of BDF1. A similar system a different selection method has been recently reported[37]. (b) Analysis of Bdf1 expression levels in different strains. Band intensities were quantified using biological triplicates. (c) Solid growth assay of strains in which Bdf1 expression is controlled by Dox. (d) Strains shown in (c) were injected in a mouse model of disseminated candidiasis. (*, p-value≤0.05 in a two-sided paired T test using ≥5 biological replicates). (e) Solid growth assay assessing the importance of Bdf1 BDs for the growth of C. albicans. Double mutations of Bdf1 BDs severely affect growth. (f) Liquid growth assay performed on the strains shown in (e). An equal fungal load was seeded for each strain and growth was monitored by optical density at 600 nm.
Figure 5:
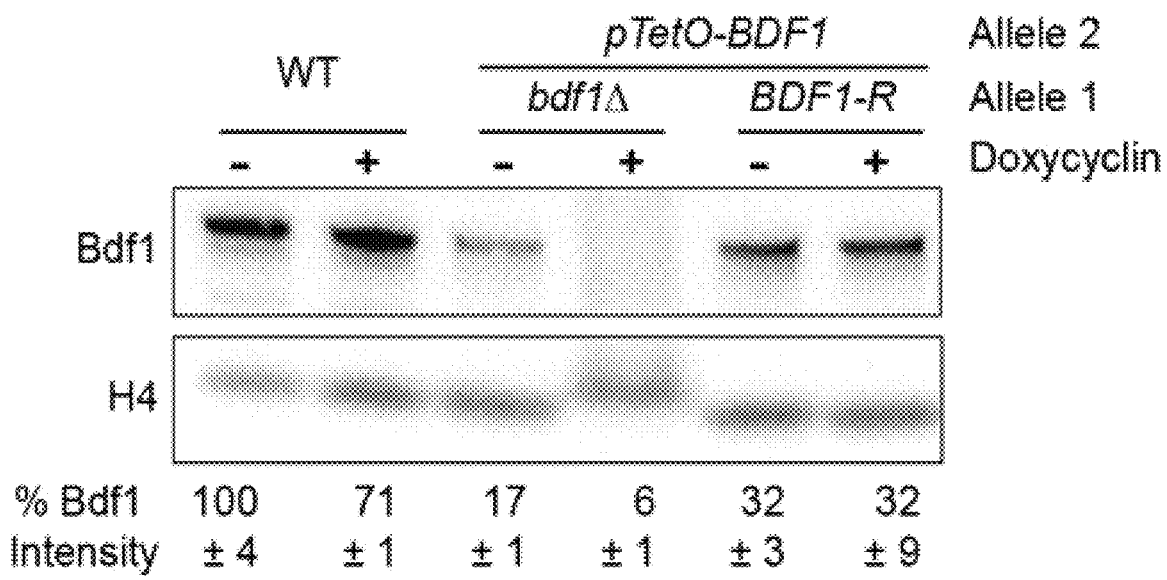
Figure 5:
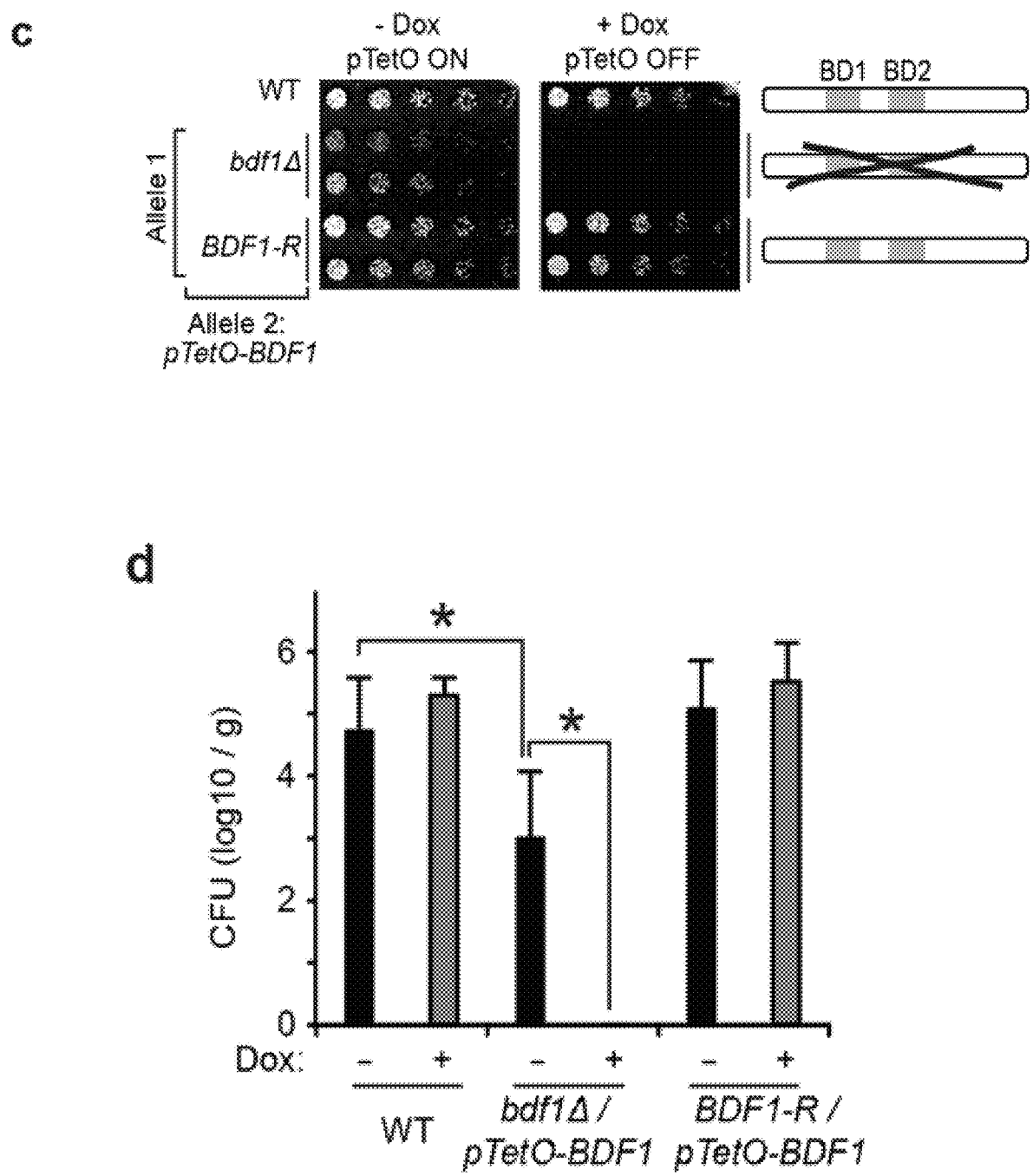
Figure 5:
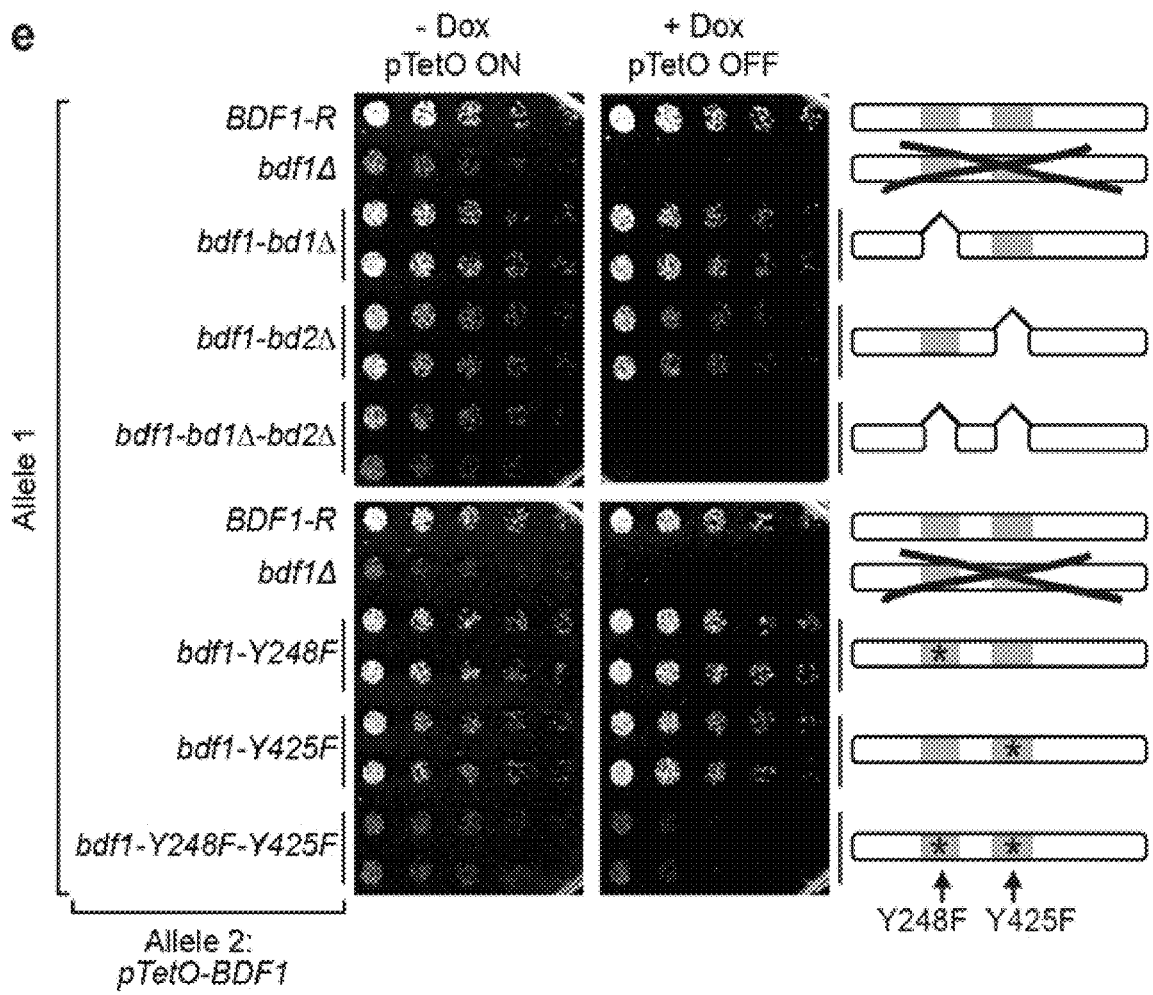
Figure 5:
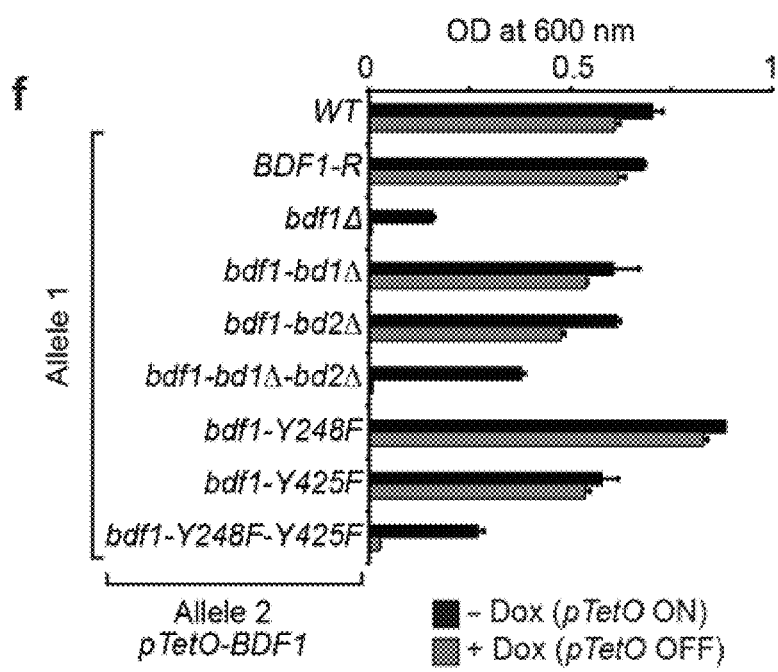

Tetracycline-dependent gene expression in *C. albicans* requires the integration of two independent fragments into the genome[34,35]. We designed a cassette containing all the required regulatory elements: the effector TetR-VP16, a selective marker ARG4, and a Tet operator, and inserted this upstream of the BDF1 ORF to generate strain Δbdf1/pTetO-BDF1 (FIG. 5*a*). In the absence of the tetracycline compound doxycycline (Dox) this promoter allows Bdf1 expression, albeit at a weaker level than the endogenous BDF1 promoter (FIG. 5*b*), as revealed by immunoblotting with a polyclonal antibody developed to allow specific CaBdf1 detection (FIG. 4*c*, 4*d*). The growth of strain Δbdf1/pTetO-BDF1 was severely compromised when BDF1 expression was repressed by the addition of Dox (FIG. 5*c*). The phenotype was rescued by re-introducing a functional copy of BDF1 (strain BDF1-R/pTetO-BDF1), confirming that Bdf1 is essential in *C. albicans*.

Using the Tet-OFF system for Dox-repressible Bdf1 expression, we next assessed the role of Bdf1 in a mouse model of invasive candidiasis. Mice injected with either WT *C. albicans* or strain BDF1-R/pTetO-BDF1 exhibited a high fungal load (>50,000 CFU/g) in the kidney 7 days post-infection (FIG. 5*d*). In the absence of Dox, the fungal load of strain bdf1Δ/pTetO-BDF1 was significantly reduced (~1000 CFU/g). This decrease is probably related to the slow growth phenotype of this strain due to a reduced level of Bdf1. In the presence of Dox, the fungal load was essentially abolished, consistent with the in vitro lethality of the BDF1 deletion. These data confirm that Bdf1 is critical for virulence in vivo.

Figure 6:
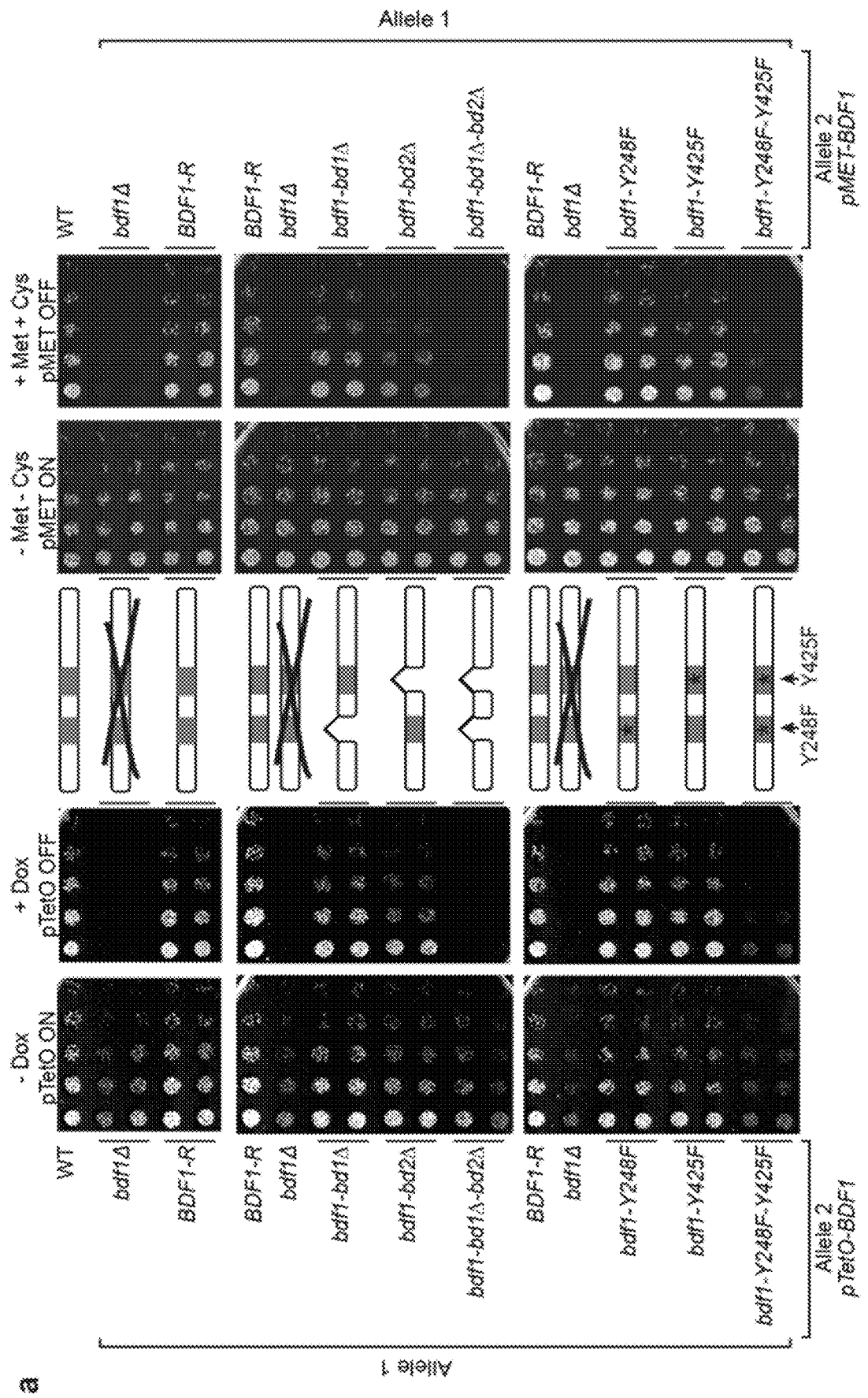
FIG. 6. Bdf1 bromodomains are essential in C. albicans. (a). Solid growth assay of strains in which Bdf1 expression is controlled by doxycycline (left) or by a methionine-sensitive promoter (pMET, right). The viability of C. albicans is lost when Bdf1 is absent or when both Bdf1 BDs are mutated. (b) Liquid growth assay with the strains presented in (a) (right side, with the pMET promoter). Left, unnormalized OD. The repression of the pMET promoter requires the addition of high concentrations of methionine and cysteine, which affects the growth of C. albicans (WT, compare black and red bars). Right, data were normalized to the WT growth (both black and red bars are equal to 100% in the WT strain).
Figure 6:
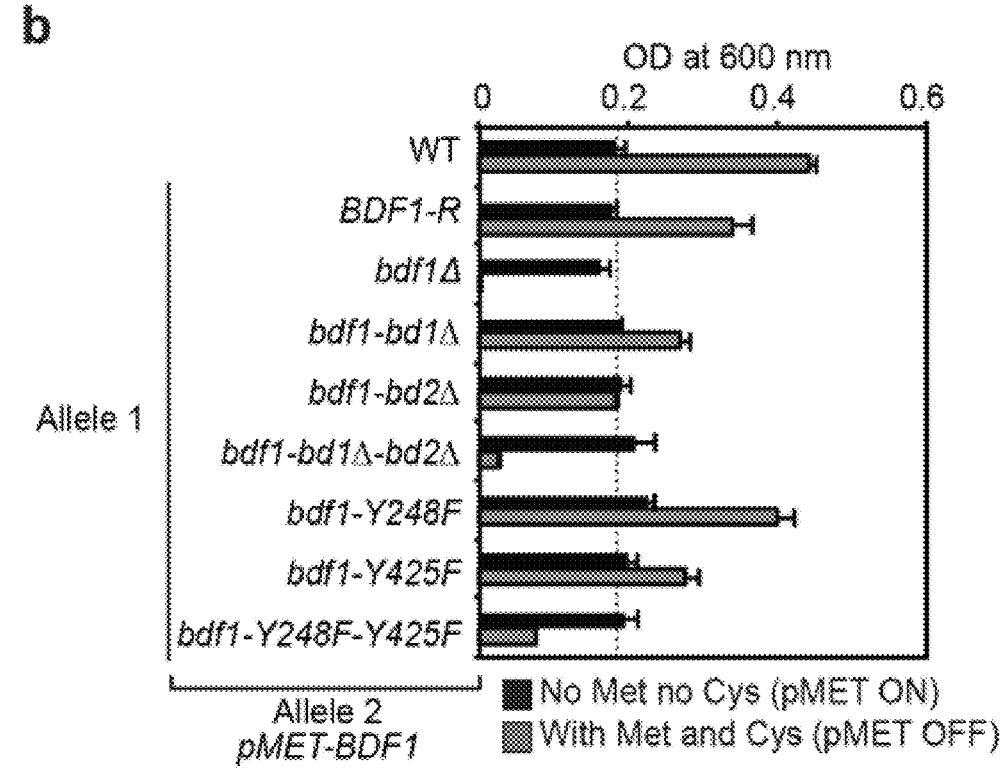
Figure 6:
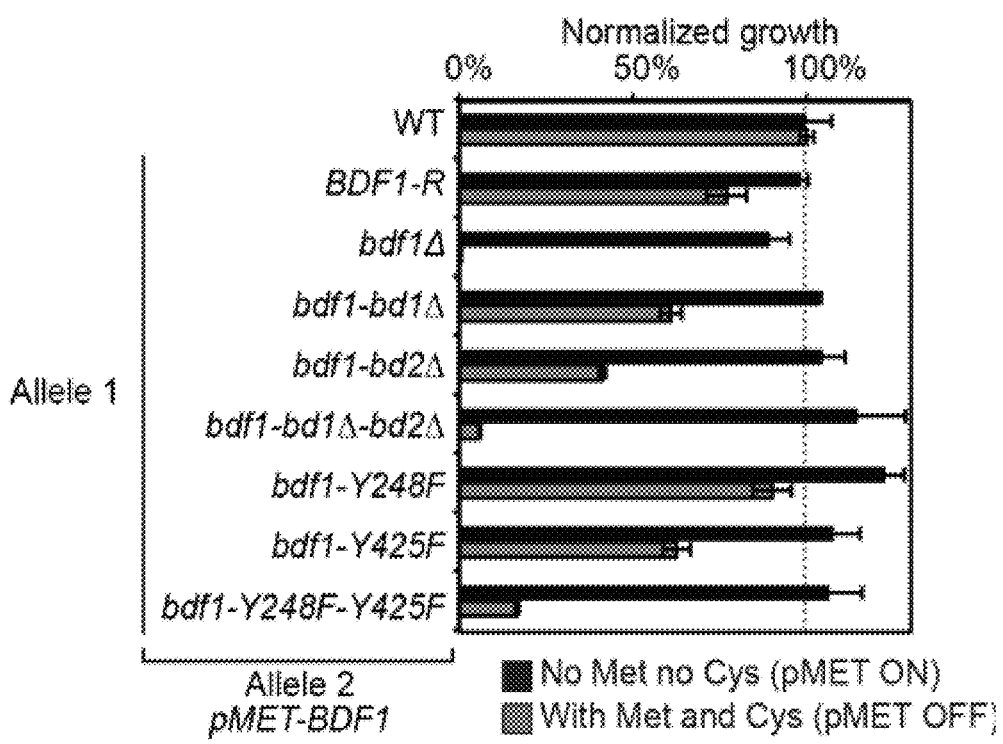

To verify the importance of BD function for fungal growth, we generated strains in which BD1 and BD2 on the Dox-repressible Bdf1 allele were inactivated by domain deletion or by mutation of conserved Tyr and Asn residues implicated in ligand binding. Strains in which both BD1 and BD2 were inactivated grew as poorly as the conditional deletion mutant, whereas strains in which only a single BD was inactivated displayed milder growth defects (FIG. 5*e*). The latter defects were more severe upon inactivation of BD2 than of BD1 and became more pronounced upon heat shock treatment. Additional assays evaluating stress (caffeine) resistance or cell wall integrity did not reveal any obvious phenotype. Growth rates measured for the above strains in a liquid assay recapitulated the phenotypes observed on solid media (FIG. 5*f*). We also used a methionine-repressed promoter as an orthogonal approach to regulate the expression of a BDF1 allele (FIG. 6*a*). Data obtained in vitro on solid media or on liquid growth confirmed the results obtained with the tetracycline system (FIG. 6*b*). Taken together, these results demonstrate that the survival of *C. albicans* in vitro and in vivo is critically dependent on the presence of Bdf1 having at least one functional BD. Tables 1 and 2 describe plasmids and strains used in this study.

TABLE 1

Plasmids used in this study.

| Name | Number | Parent | Description |
|---|---|---|---|
| 5'BDF1-HIS1-3'BDF1 | pJG197 | | pCR2.1 TOPO containing HIS1 marker flanked by upstream and downstream BDF1 sequence. |
| bdf1-LEU2 | pJG214 | | pCR2.1 TOPO containing BDF1 ORF fused to LEU2 marker. |
| bdf1-bd1Δ | pJG224 | | pCR2.1 TOPO containing bdf1-bd1Δ sequence fused to LEU2 marker |
| bdf1-bd2Δ | pJG225 | | pCR2.1 TOPO containing bdf1-bd2Δ sequence fused to LEU2 marker |
| bdf1-bd1Δ-bd2Δ | pJG226 | | pCR2.1 TOPO containing bdf1-bd1Δ-bd2Δ sequence fused to LEU2 marker |
| bdf1-bd1Y266F-LEU2 | pJG215 | pJG214 | pCR2.1 TOPO containing bdf1-bd1Y266F sequence fused to LEU2 marker |
| bdf1-bd2Y425F-LEU2 | pJG216 | pJG214 | pCR2.1 TOPO containing bdf1-bd2Y425F sequence fused to LEU2 marker |

TABLE 1-continued

Plasmids used in this study.

| Name | Number | Parent | Description |
|---|---|---|---|
| bdf1-bd1Y248F-bd2Y425F-LEU2 | pJG217 | pJG215 | pCR2.1 TOPO containing bdf1-bd1Y248F-bd2Y425F sequence fused to LEU2 marker |
| ARG4-pTetO-bdf1 | pJG254 | | pCR2.1 TOPO containing ARG4 marker, tTA-TetR-VP16, pTet and BDF1 |

Cassette to transform, first entry=PCR; last entry, digestion with XhoI; all others, digestion with ApaI.

TABLE 2

Strains used in this study.

| Name | Number | Parent | Genotype |
|---|---|---|---|
| SN152 | SN152 | SCS314 | ura3D-iroDimm/URA3-IRO1, his1D/his1D, arg4D/arg4D, leu2D/leu2D |
| bdf1Δ/pTetO-BDF1 | JG105 | SN152 | ura3D-iroDimm/URA3-IRO1, BDF1::pTetO-BDF1-ARG4/bdf1::HIS1, leu2D/leu2D |
| BDF1-R/pTetO-BDF1 | JG108 | yCaJG105 | ura3D-iroDimm/URA3-IRO1, bdf1::pTetO-BDF1-ARG4/bdf1::BDF1-R-LEU2, his1D/his1D |
| bdf1-bd1Δ/pTetO-BDF1 | JG120 | yCaJG105 | ura3D-iroDimm/URA3-IRO1, bdf1::pTetO-BDF1-ARG4/bdf1::bdf1-bd1Δ-LEU2, his1D/his1D |
| bdf1-bd2Δ/pTetO-BDF1 | JG123 | yCaJG105 | ura3D-iroDimm/URA3-IRO1, bdf1::pTetO-BDF1-ARG4/bdf1::bdf1-bd2Δ-LEU2, his1D/his1D |
| bdf1-bd1Δ-bd2Δ/pTetO-BDF1 | JG127 | yCaJG105 | ura3D-iroDimm/URA3-IRO1, bdf1::pTetO-BDF1-ARG4/bdf1::bdf1-bd1Δ-bd2Δ-LEU2, his1D/his1D |
| bdf1-bd1Y248F/pTetO-BDF1 | JG111 | yCaJG105 | ura3D-iroDimm/URA3-IRO1, bdf1::pTetO-BDF1-ARG4/bdf1::bdf1-bd1Y248F-LEU2, his1D/his1D |
| bdf1-Bd2Y425F/pTetO-BDF1 | JG114 | yCaJG105 | ura3D-iroDimm/URA3-IRO1, bdf1::pTetO-BDF1-ARG4/bdf1::bdf1-Bd2Y425F-LEU2, his1D/his1D |
| bdf1-bd1Y248F-bd2Y42SF/pTetO-BDF1 | JG117 | yCaJG105 | ura3D-iroDimm/URA3-IRO1, bdf1::pTetO-BDF1-ARG4/bdf1::bdf1-bd1Y248F-Bd2Y425F-LEU2, his1D/his1D |

Reference, first entry, PMC549318, all others, this study.
The Ligand Binding Pocket of Human and Fungal BET BDs are Stereochemically Distinct.

Figure 7:
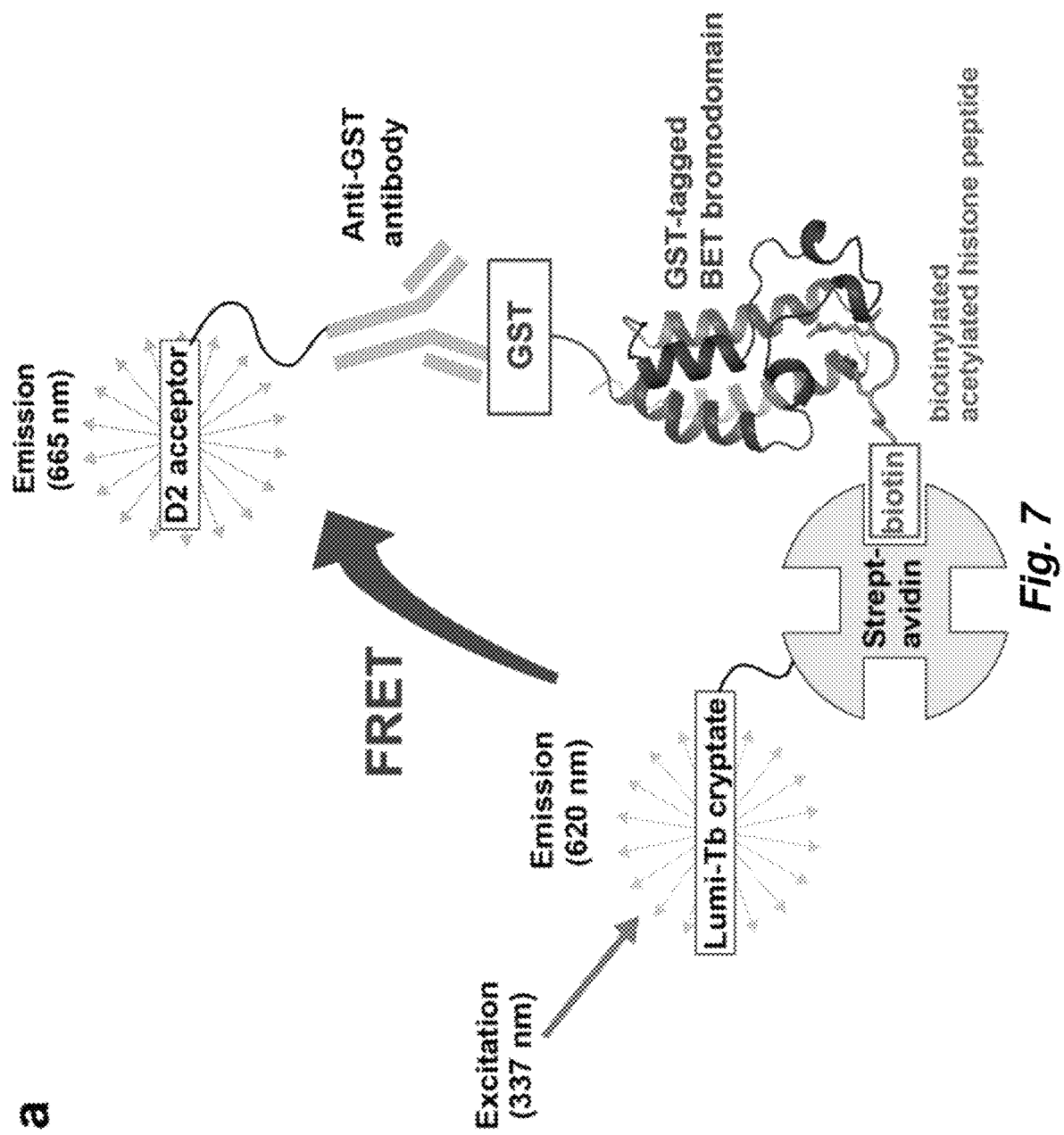
FIG. 7. Homogeneous time-resolved fluorescence (HTRF) assay. a. Assay configuration. A biotinylated tetra-acetylated histone peptide is bound to streptavidin beads which are coupled to a terbium-based donor fluorophore, lumi-Tb cryptate. GST-tagged bromodomain is bound by an anti-GST antibody coupled to the acceptor fluorophore, an organic molecule termed D2. Peptide binding by the bromodomain brings the donor and acceptor within FRET distance. In this situation, excitation of the donor at 337 nm causes energy transfer to the donor, whose emitted fluorescence is monitored at 665 nm in a time-resolved manner so as to eliminate transient background fluorescence. b-d. Binding of biotinylated tetra-acetylated H4 (H4ac4) peptide by the BD1 bromodomains from human Brd4 (b), S. cerevisiae Bdf1 (c) and C. albicans Bdf1 (d) as measured by an increase in HTRF signal with increasing peptide concentration.
Figure 7:
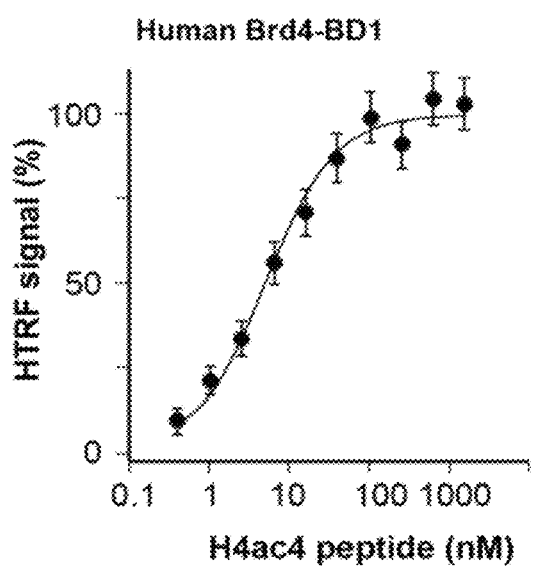
Figure 7:
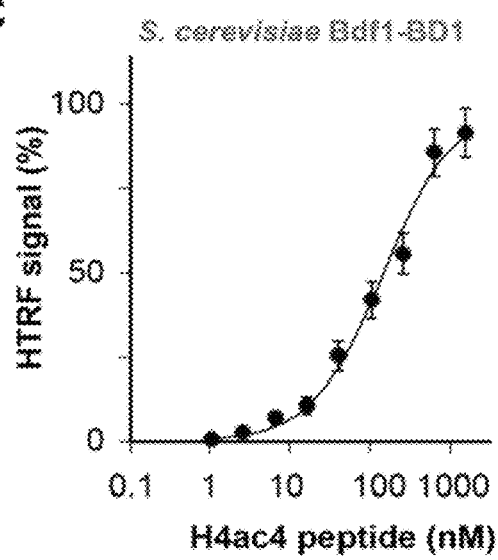
Figure 7:
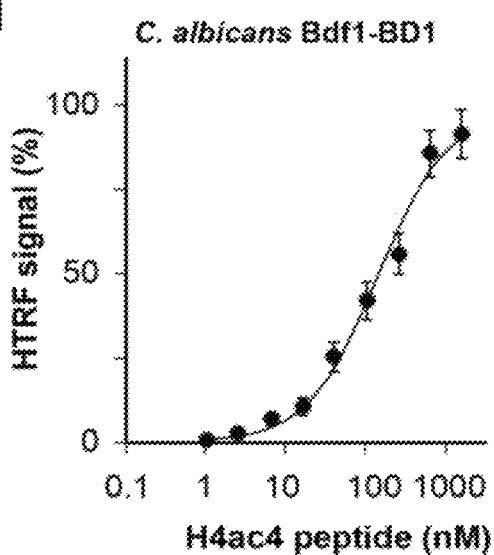
Figure 8:
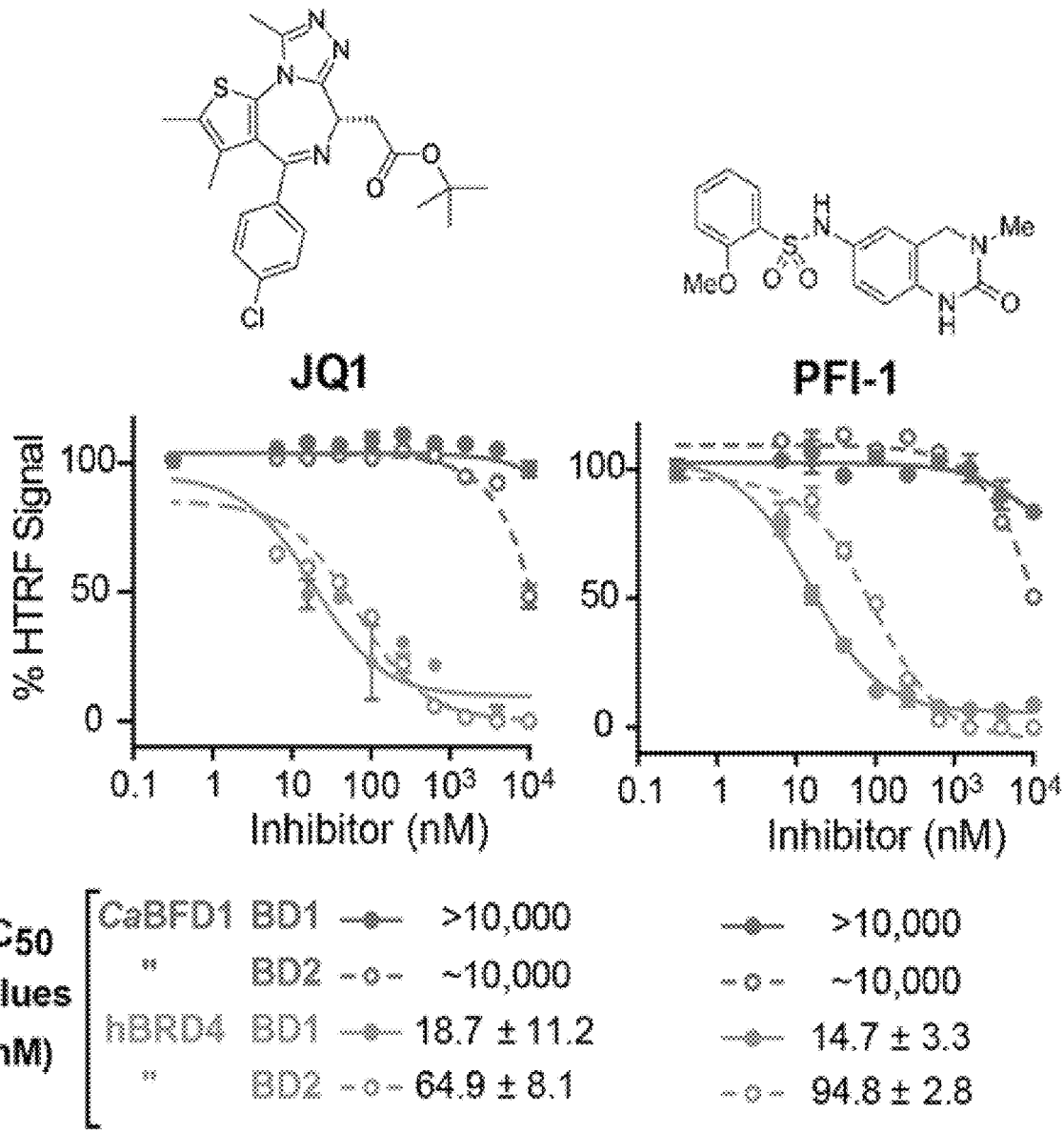
FIG. 8. CaBdf1 BDs are insensitive to human BET inhibitors. (a) HTRF inhibition assays performed on BD1 and BD2 from CaBdf1 and human Brd4 to evaluate the effects of four human BET inhibitors. Inhibition curves are shown as closed (BD1) and open (BD2) circles in green (Brd4) and magenta (Bdf1). $IC_{50}$ values are summarized below each graph. (b) Thermal stability of the indicated BET BDs in the presence and absence of BET inhibitors determined by differential scanning fluorimetry. The thermal shift ($\Delta Tm$) for each inhibitor is indicated. Curves obtained in the presence (thick lines) or absence (thin lines) are plotted for CaBDF1 BD1 (solid magenta), CaBDF1 BD2 (dashed magenta) and human Brd4 (green). (c) ITC experiment measuring the binding of JQ1 to CaBDF1 BDs (magenta) and to human Brd4 BD1 (green). (d) iBET-151 and bromosporine do not affect C. albicans growth, even when Bdf1 bromodomains are deleted. Experiments have been performed in the presence of doxycycline, which represses the pTetO-BDF1 allele.
Figure 8:
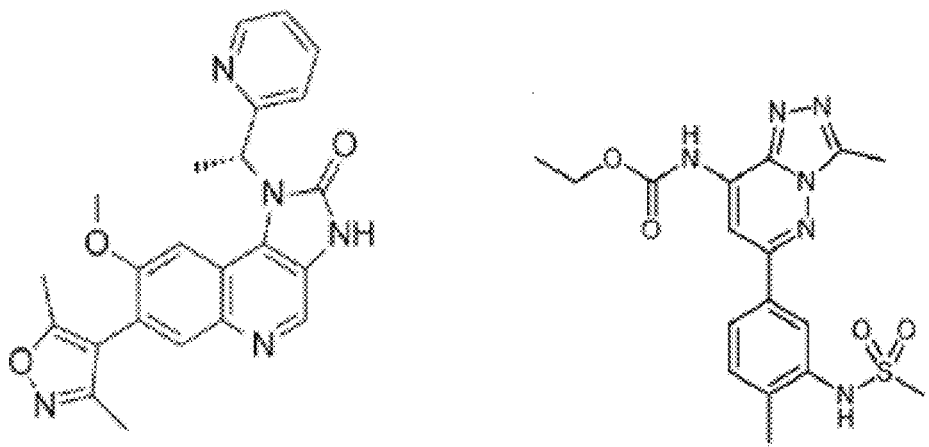
Figure 8:
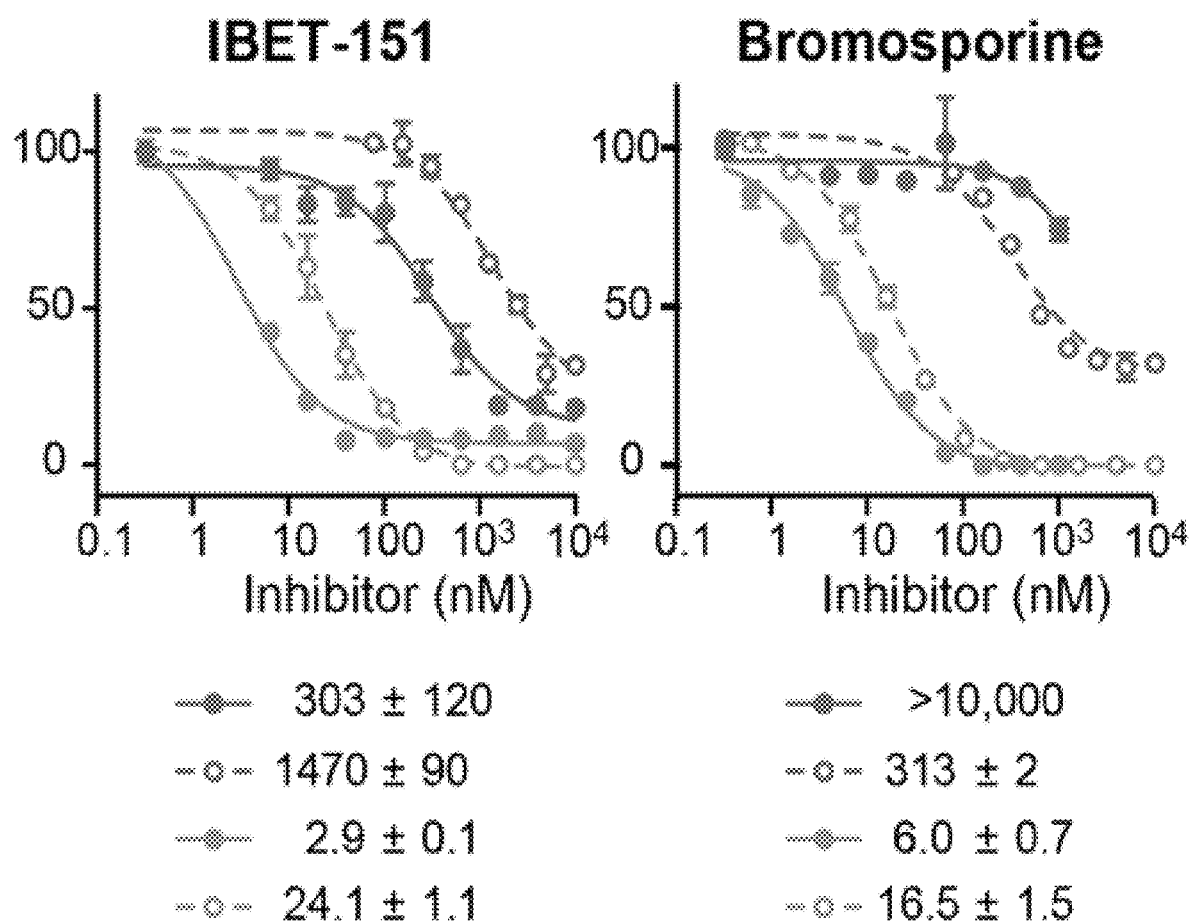
Figure 8:
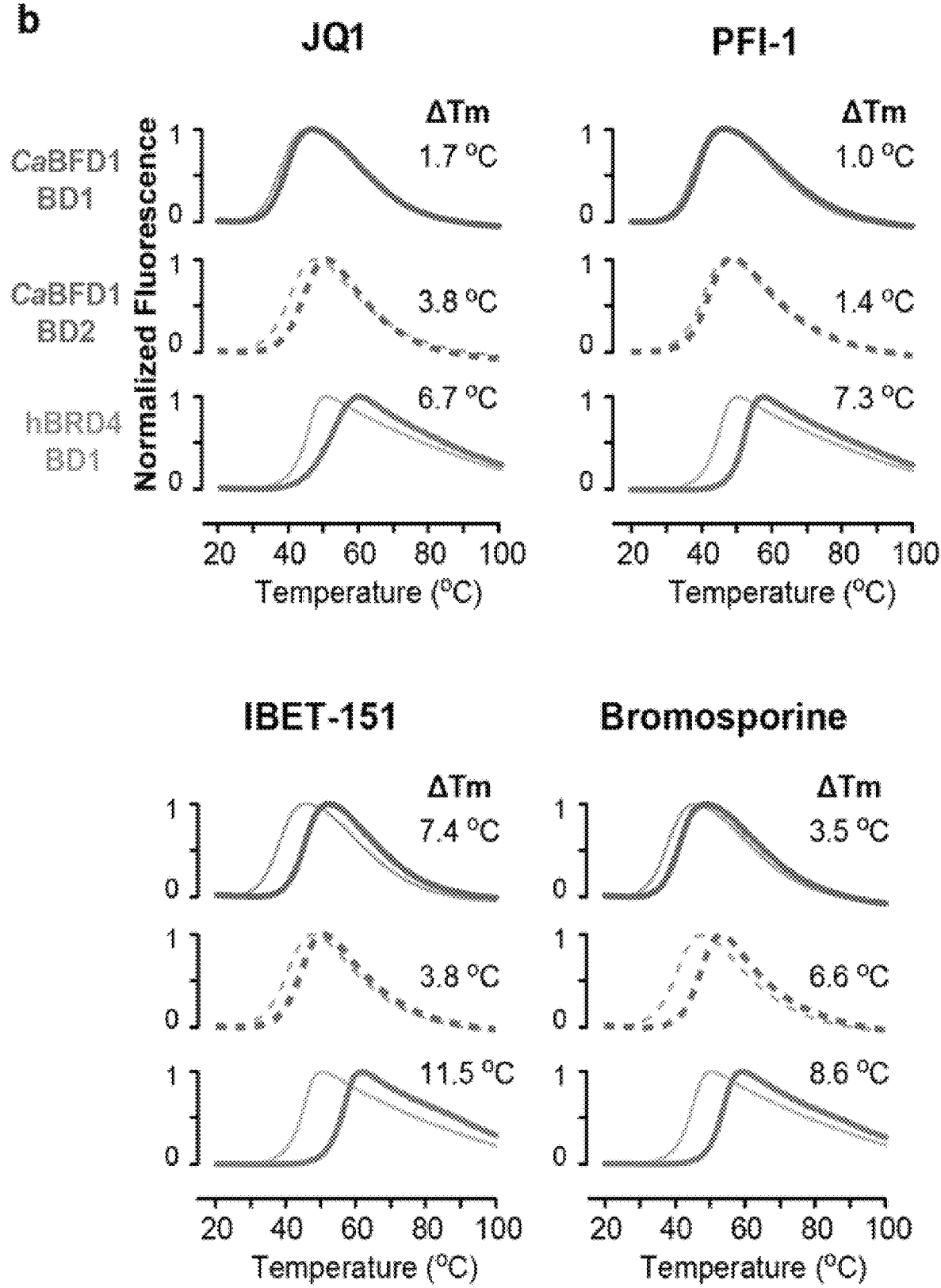
Figure 8:
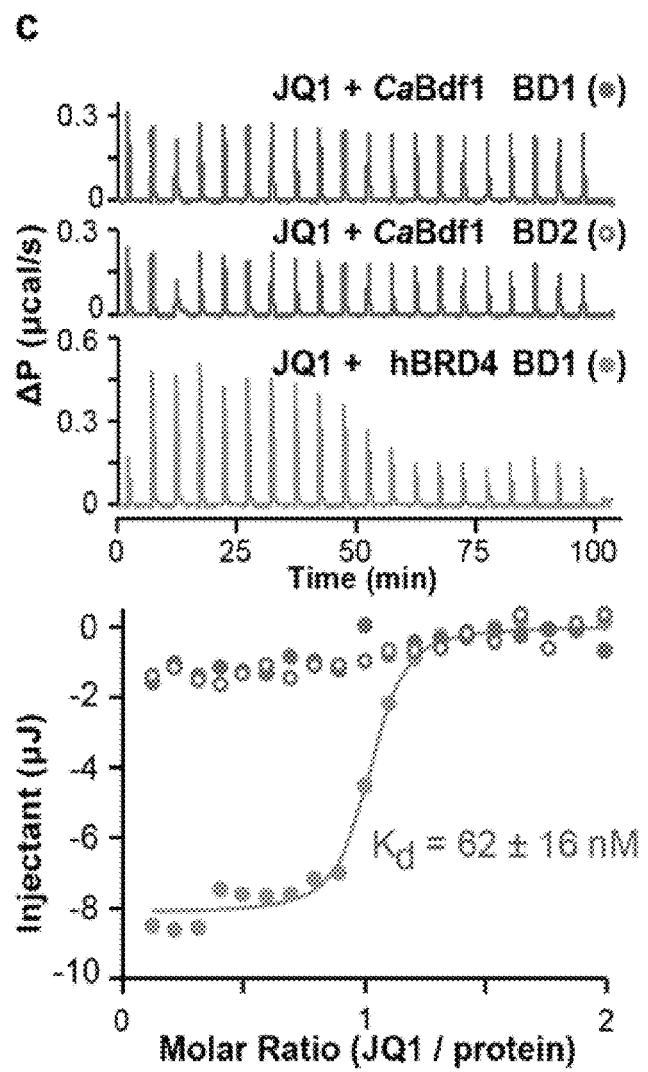
Figure 8:
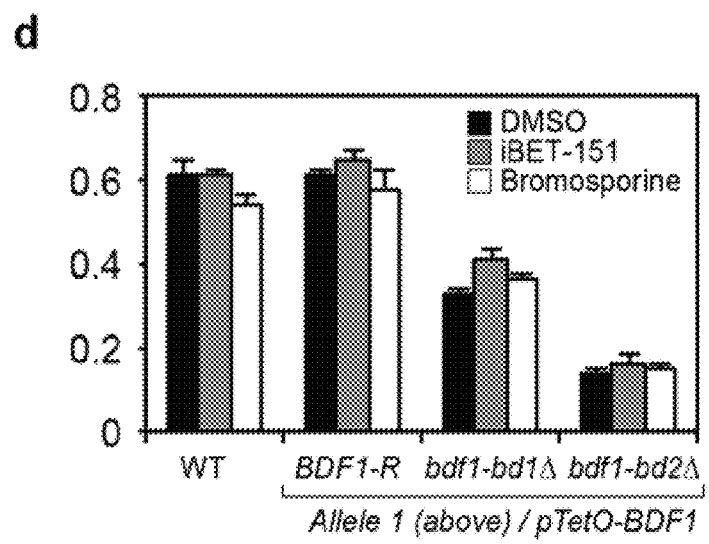

A key consideration in establishing fungal BET BD inhibition as a feasible chemotherapeutic strategy is whether these domains can be targeted by small-molecule inhibitors without antagonizing human BET function. To probe the similarity between the ligand binding pockets of *C. albicans* and human BET BDs, we asked whether human BET inhibitors could inhibit CaBdf1 BDs. We used a homogeneous time-resolved fluorescence (HTRF) assay (FIG. 7) to evaluate the ability of BET inhibitors JQ1, PFI-1, IBET-151 and bromosporine to inhibit BD binding to an H4ac4 peptide (FIG. 8a). All four inhibitors efficiently inhibited human Brd4 BD1 and BD2, with $IC_{50}$ values in the low nM range (3-95 nM), consistent with previously reported results.

In contrast, the CaBdf1 BDs were significantly less sensitive to all four inhibitors, with $IC_{50}$ values ranging between 0.3 and >10 μM, implying a reduction of 2-3 orders of magnitude relative to the corresponding BD from Brd4. The strongest inhibition ($IC_{50}$ of ~300 nM) was observed for IBET-151 on CaBdf1 BD1 and for the pan-BET inhibitor bromosporine on CaBdf1 BD2, which nevertheless corresponds to a 60- or 20-fold reduction in sensitivity relative to Brd4. These results were verified in differential fluorimetry scanning (DSF) measurements, which exploit the fact that inhibitor binding enhances the thermal stability of BET bromodomains.

Whereas the four inhibitors substantially increased the melting temperature ($T_m$) of human Brd4 BD1 (by 6.7-11.5° C.), the $T_m$ values of the fungal BDs were only slightly increased (by 1.0-3.8° C.), indicating low affinity, with the exception of IBET-151 and bromosporine on CaBdf1 BD1 and BD2, respectively ($\Delta T_m$ values of ~7° C.). These results were confirmed for JQ1 using isothermal titration calorimetry (ITC): whereas JQ1 bound Brd4 BD1 tightly ($K_d$ of 62±16 nM), as expected, no binding was detected to either BD1 or BD2 of CaBdf1. Furthermore, none of the BET inhibitors had any significant effect on the growth of *C. albicans* in vitro, including the two inhibitors (IBET-151 and bromosporine) with the lowest $IC_{50}$ values (FIG. 8d). The above findings indicate that the ligand binding pockets of CaBdf1 possess structural features distinct from those of their human counterparts which potentially may be targeted selectively by small-molecule inhibitors. To identify these distinguishing features, we determined the crystal structures of BD1 and BD2 from *S. cerevisiae* and *C. albicans* Bdf1 (see U.S. Provisional Patent Application No. 62/366,973 for crystallographic statistics).

Figure 9:
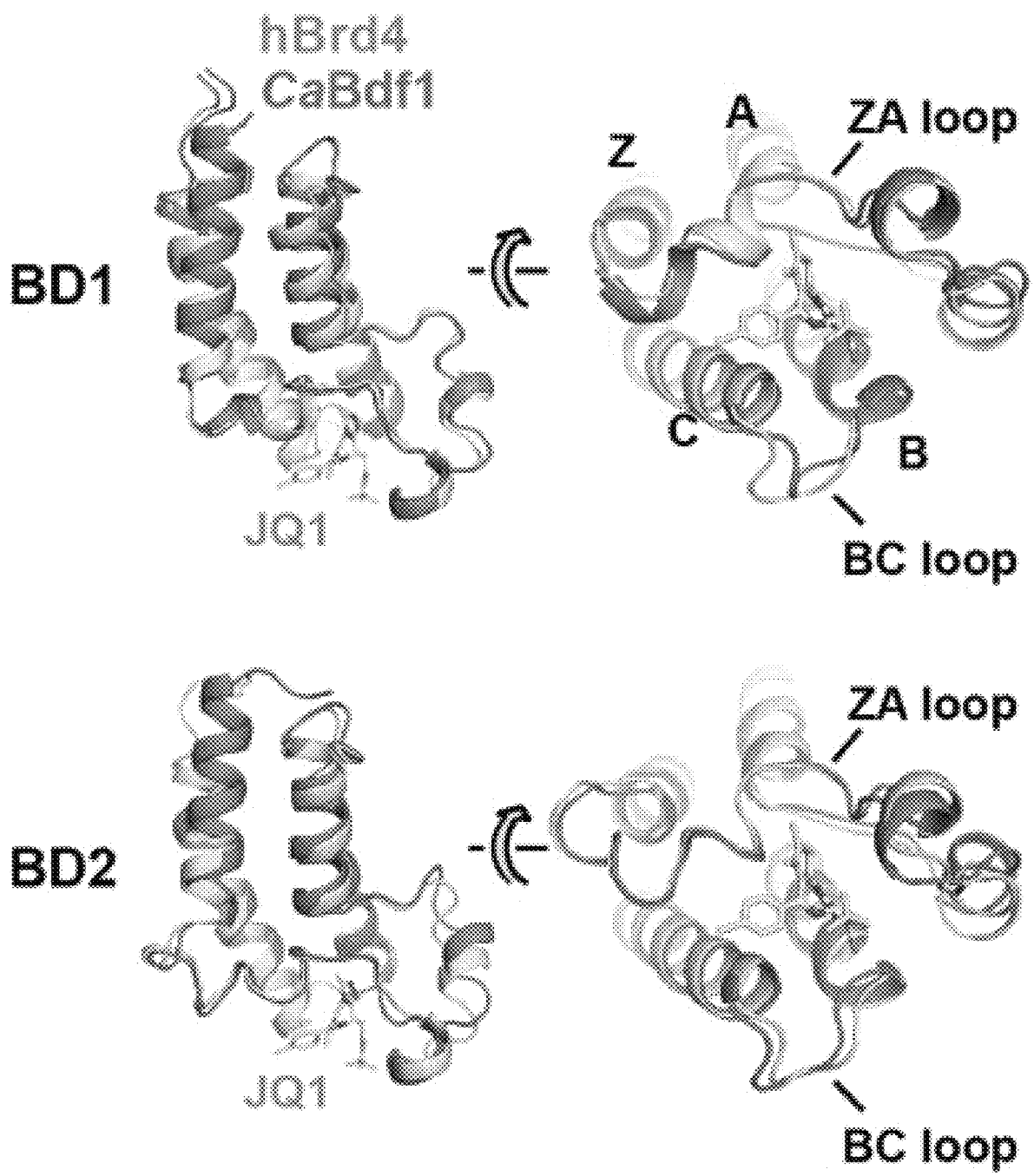
FIG. 9. Crystal structures of fungal BET BDs. (a) Structural alignment of CaBdf1 BD1 (top) and BD2 (bottom) with the corresponding human Brd4 BDs. For clarity, the N-terminal 20 residues preceding helix Z are omitted from the BD1 structures. (b) Plots of electrostatic surface potential of BD1 (top) and BD2 (bottom) structures from human Brd4, C. albicans, and S. cerevisiae. Regions of negative and positive potential are shown in red and blue, respectively. (c) Comparative analysis of the ligand-binding pockets of fungal and human BET BDs. Panels show the structural alignment of the indicated fungal BD with the corresponding BDs from all four human BET proteins (Brd2, Brd3, Brd4 and Brdt). Residues which are unique to the fungal BD are shown in magenta, with the corresponding human residues in gray. Residues in orange are conserved between fungal and human BDs but are shifted in the fungal structure.
Figure 9:
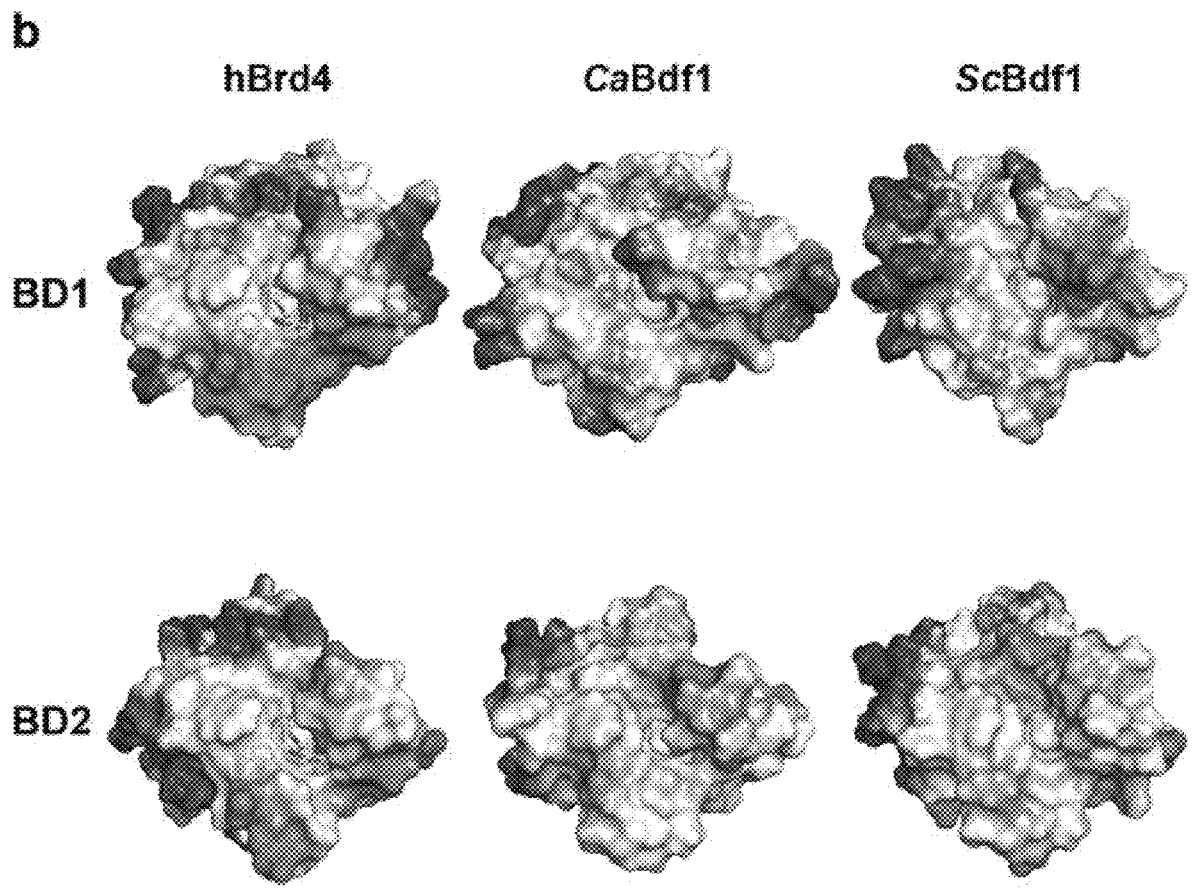
Figure 9:
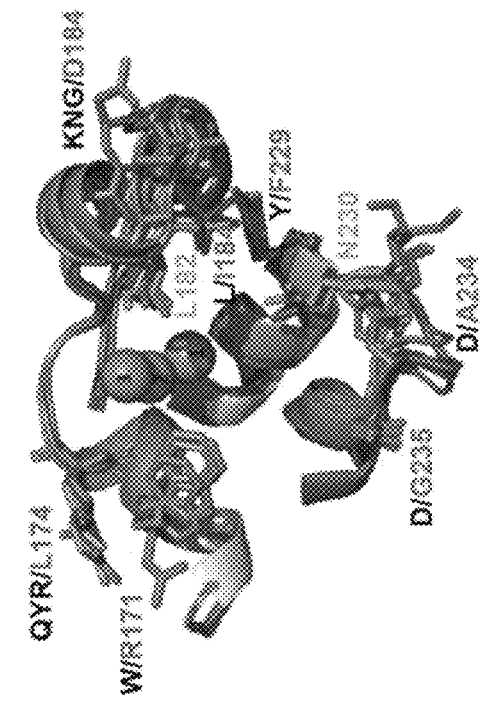
Figure 9:
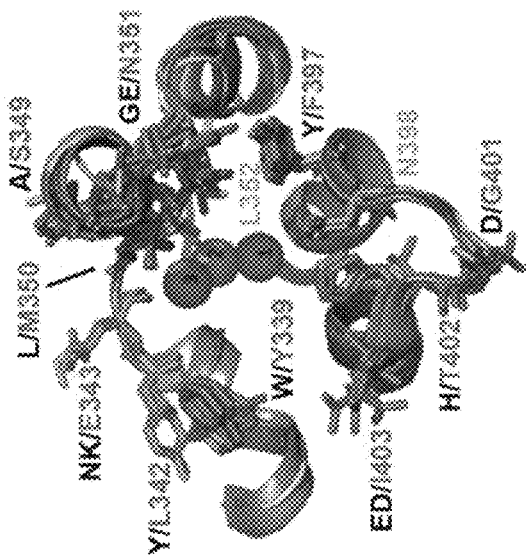
Figure 9:
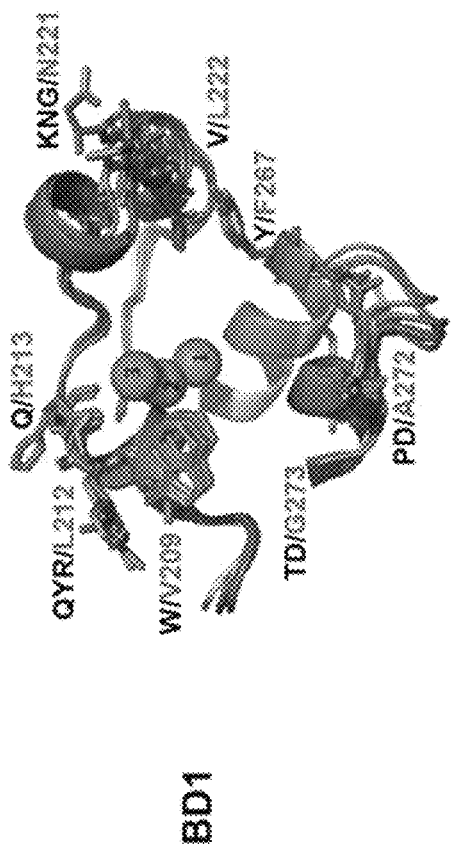
Figure 9:
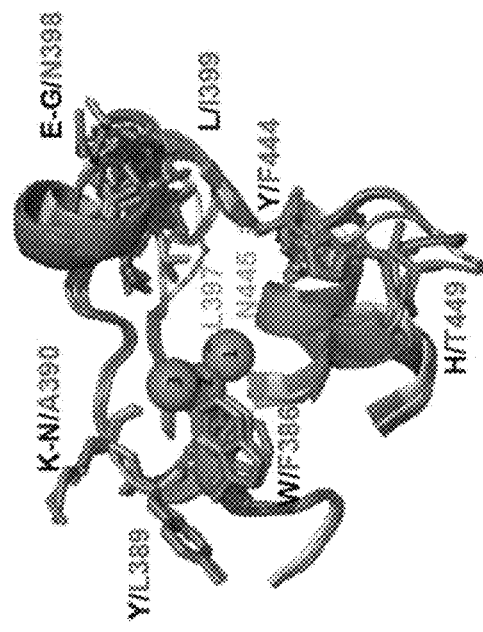

*S. cerevisiae* Bdf1 was included in this analysis because it is phylogenetically closer than CaBdf1 to orthologs from several fungal pathogens (e.g., *C. glabrata* and *A. fumigatus*. FIG. 3a), and thus informs on the suitability of targeting Bdf1 in other fungal species. Like canonical bromodomains, the four fungal BDs each comprise a left-handed bundle of four helices (αZ, αA, αB and αC) with the ZA and BC loops defining the ligand binding pocket (FIG. 9a). The fungal structures closely resemble those of the corresponding human BET BDs, with a mean pairwise RMSD value for Cα atoms of <1.7 Å and <1.2 Å over the entire BD1 and BD2 domains, respectively, and of 0.5 and 1.4 Å (*C. albicans*) or 1.0 and 1.8 Å (*S. cerevisiae*) within the BD1 and BD2 ligand binding loops, respectively. Most residues within the ligand binding pocket, including four structured water molecules important for ligand recognition, are conserved between the human and fungal orthologs. However, several residues differ in identity or spatial location, resulting in significant differences in the stereochemical properties of the ligand binding pocket (FIG. 9b) (c.f. ref[36]). Superimposing the structure of Brd4 BD1 bound to JQ1 with the fungal BET BD1 structures reveals why the latter are JQ1-insensitive. Sequence analysis of Bdf1 proteins from the most prevalent fungal pathogens reveals that all differ from the human orthologs at key positions within the ZA and BC loops (see FIG. 17 of U.S. Provisional Patent Application No. 62/366,973). Taken together, the above structural and phylogenetic data indicate that fungal BET BDs may feasibly be targeted with high selectivity relative to human BET bromodomains.
Selective Targeting of Bdf1 BDs by Small Molecule Inhibitors.

Figure 10:
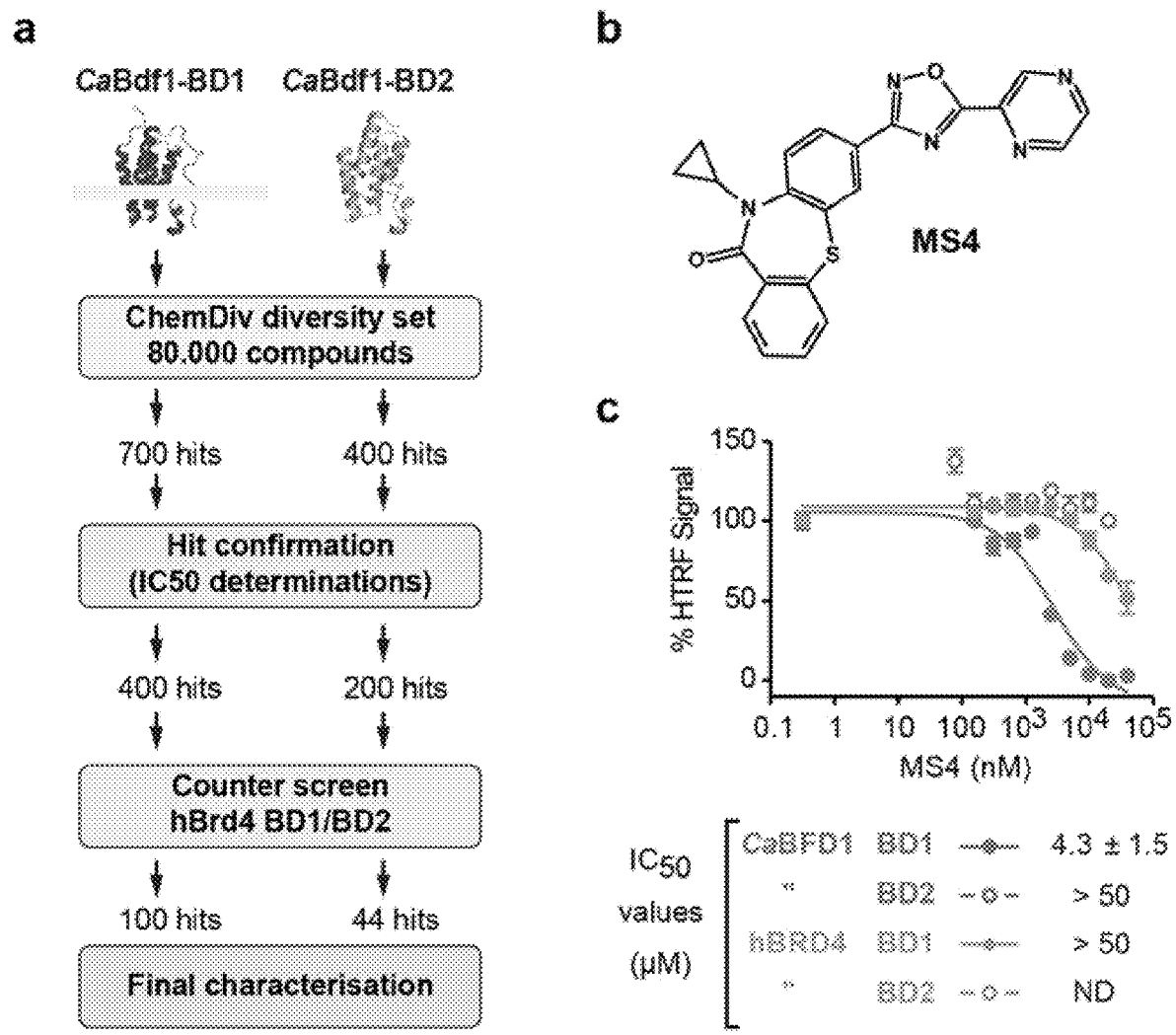
FIG. 10. Identification of a selective inhibitor of *C. albicans* Bdf1 BD1. (a) Chemical screening strategy employed. (b) Chemical structure of dibenzothiazepinone compound MS4. (c) HTRF assays showing selective inhibition of CaBdf1 BD1 by MS4. (d) ITC experiment showing selective binding of MS4 to CaBdf1 BD1. (e-f) Details of MS4 recognition and structural basis of selectivity.
Figure 10:
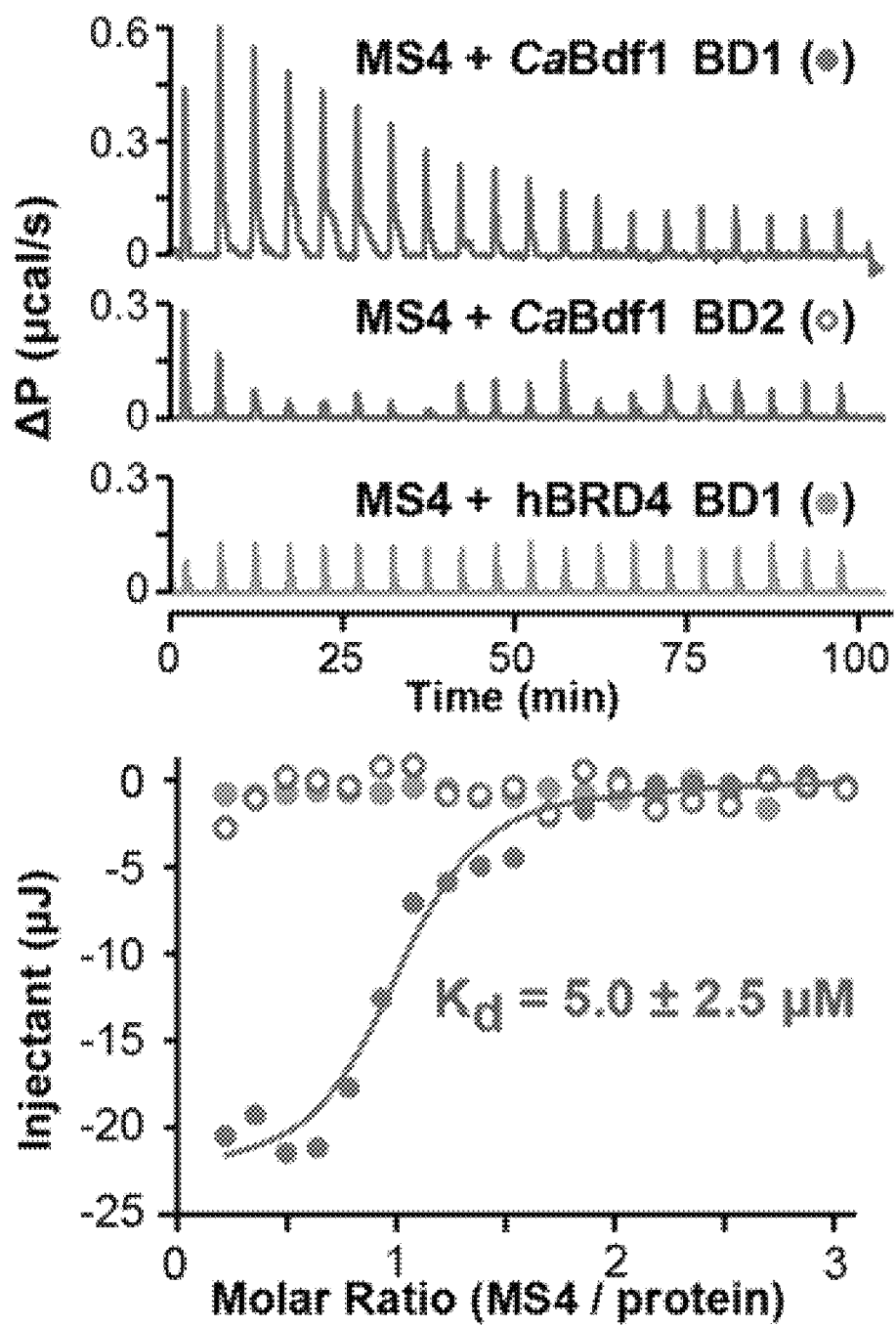
Figure 10:
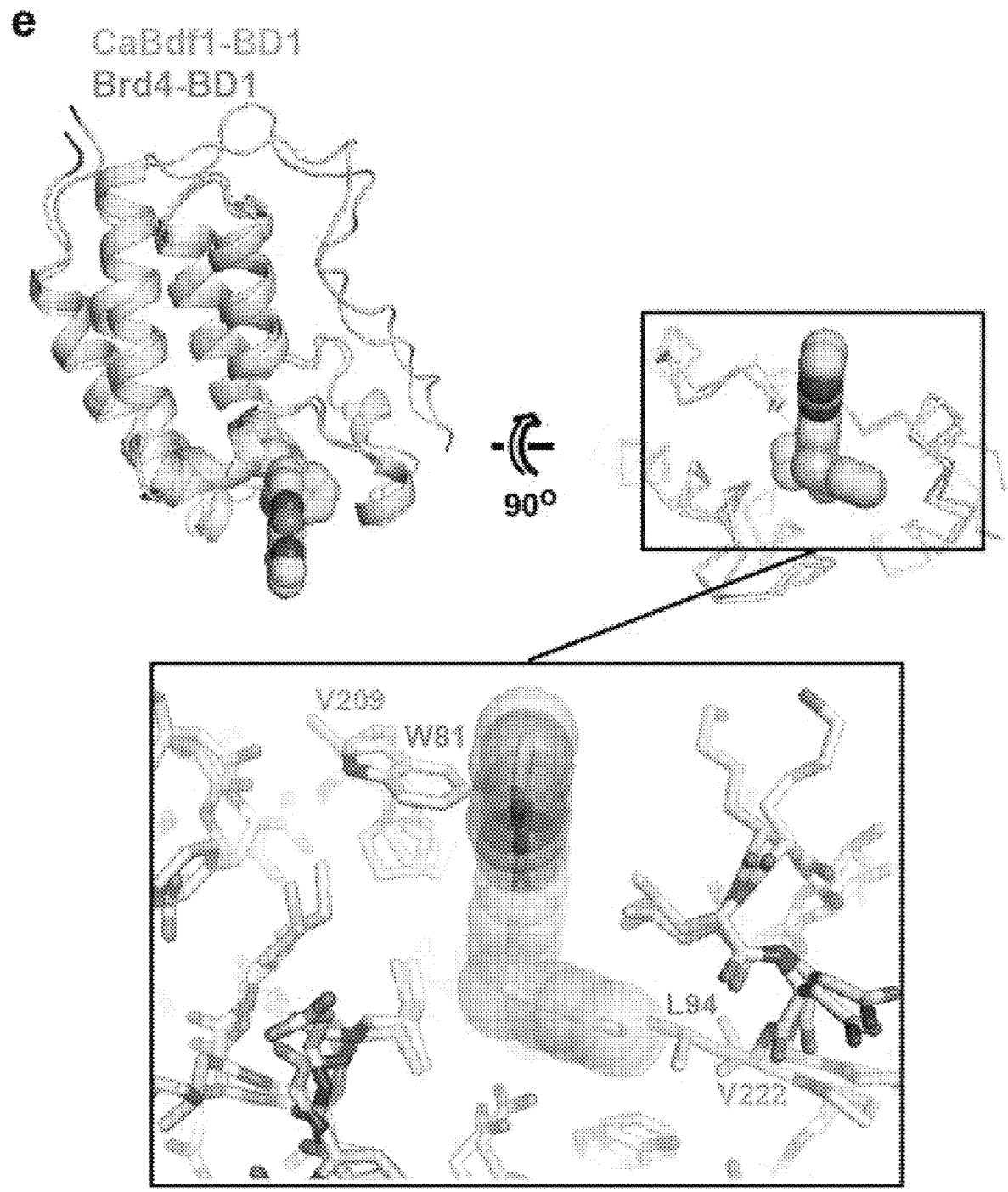
Figure 10:
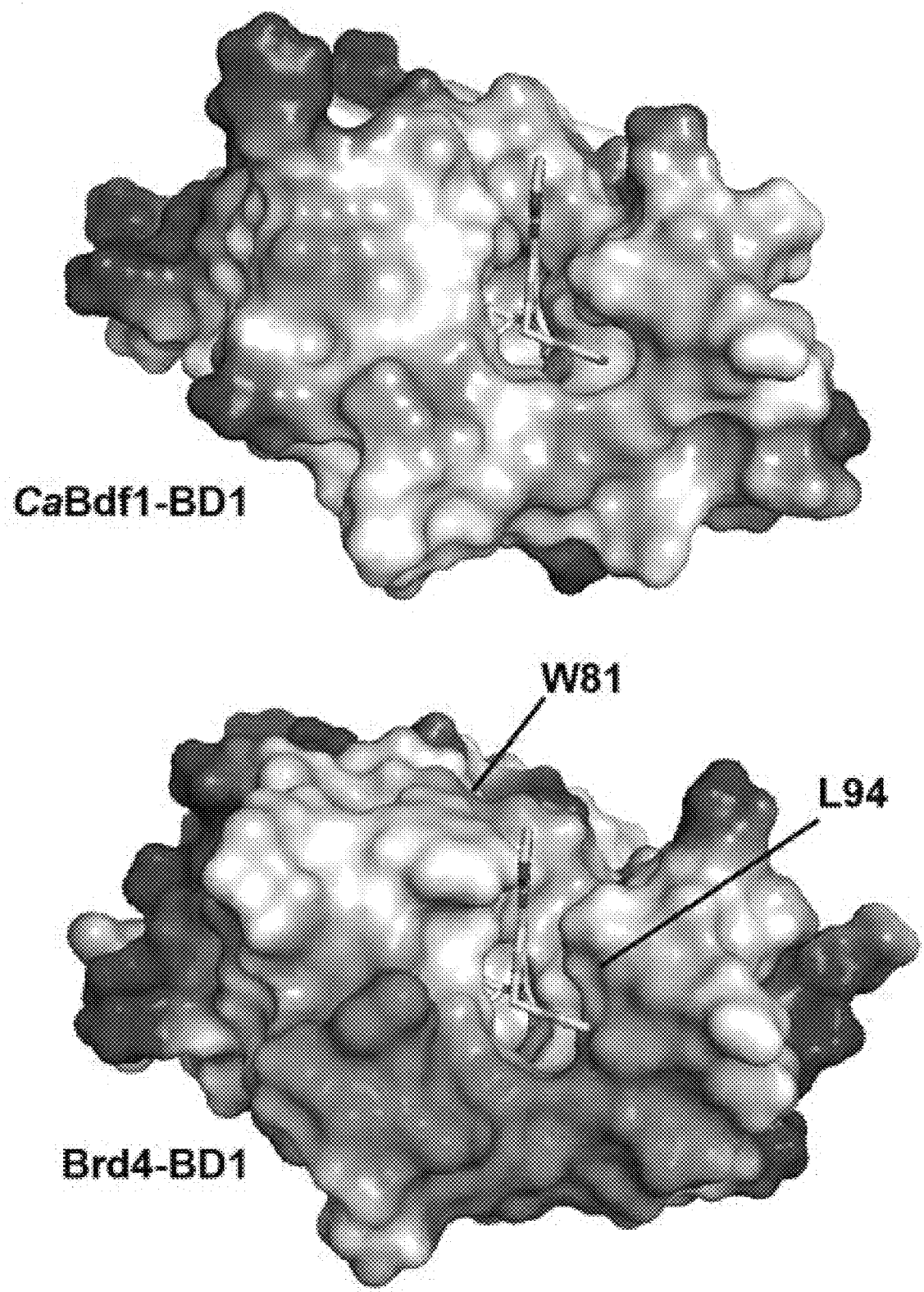

To establish proof-of-principle, we set out to identify a small molecule inhibitor that would selectively target *C. albicans* Bdf1 BDs without inhibiting human BET BDs. We used our HTRF inhibition assay to screen a chemically diverse library of 80,000 compounds, resulting in the identification of several hundred hits for each BD (FIG. 10a). Dose-response curves measured for CaBdf1 and Brd4 BDs identified approximately 100 and 44 compounds which were selective for the fungal BD1 and BD2, respectively, as defined by a >20-fold difference in $IC_{50}$ value relative to the human BD. Among these were several dibenzothiazepinone compounds, which exhibited $IC_{50}$ values between 0.4 and 7 µM toward Bdf1 BD1 but showed no or only weak inhibition of Brd4 BD1 at the highest concentration tested (20 µM) (FIG. 11).

Figure 12:
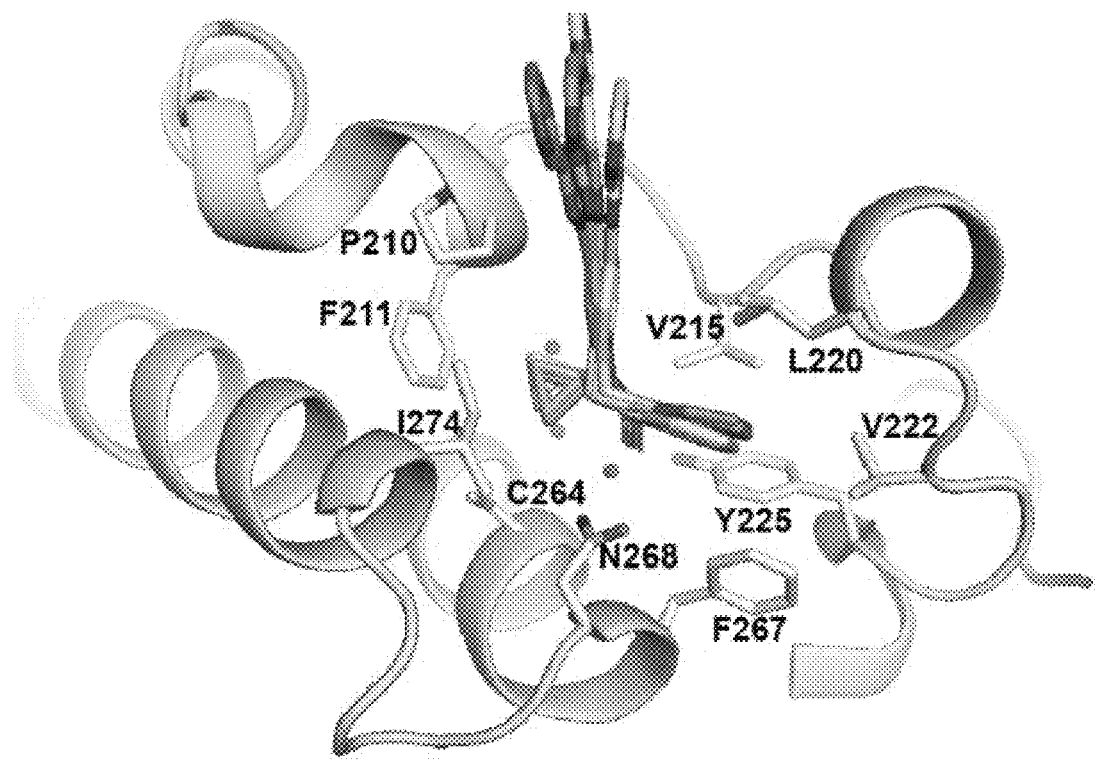
FIG. 12. Details of MS4 recognition by CaBdf1-BD1. (a) Structural alignment of the four BD1-MS4 complexes in the crystallographic asymmetric unit. (b) Residue environment of MS4 within the active site.
Figure 12:
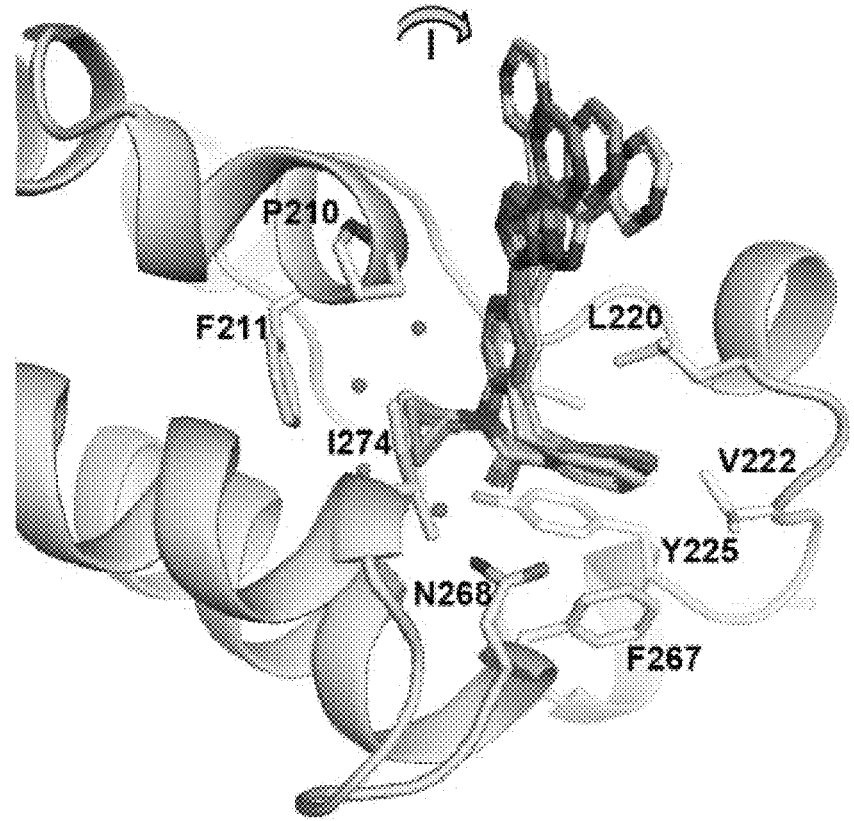
Figure 12:
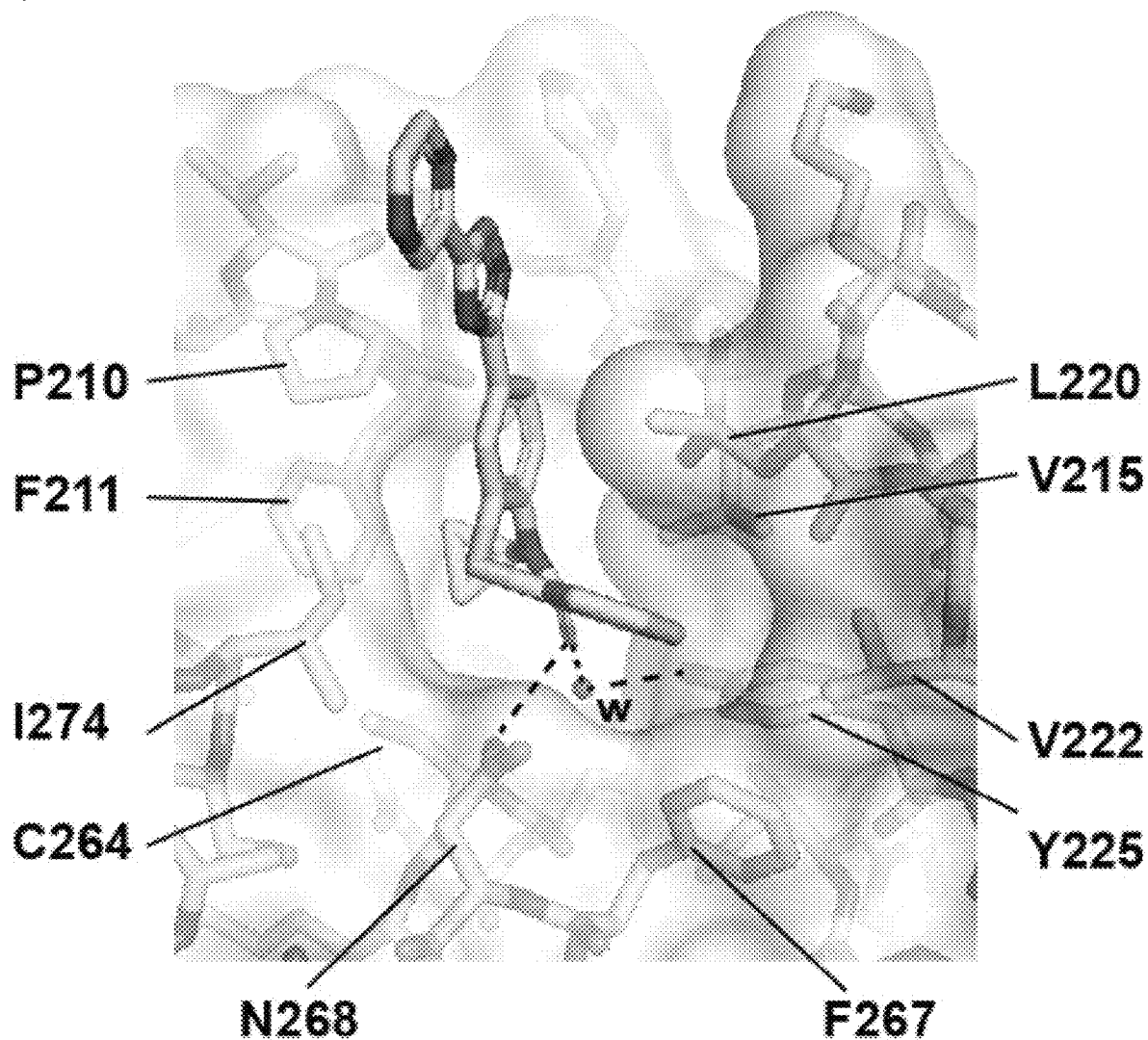

To determine the molecular basis of selectivity we determined the crystal structure of *C. albicans* Bdf1 BD1 bound to one of these inhibitors, compound MS4, which in addition to the dibenzothiazepinone scaffold bears cyclopropyl, oxadiazole and pyrazine groups (FIG. 10b). ITC measurements showed that MS4 binds CaBdf1 BD1 with a Kd of ~5 µM, consistent with the $IC_{50}$ value determined (4.3 µM). In contrast, no significant binding was detected for Brd4-BD1 and only modest inhibition was observed for CaBdf1 BD2 (FIG. 10c, 10d). The MS4-bound structure of CaBdf1-BD1 was solved at 1.7 Å resolution and contains four BD/inhibitor complexes in the asymmetric unit. The dibenzothiazepinone and cyclopropyl moieties sit deep in the ligand binding pocket and their recognition is conserved across all four complexes (FIG. 10e-f and FIG. 12).

In contrast, the oxadiazole and pyrazine groups protrude from the pocket in different orientations and mediate interactions (including crystal contacts) which vary among the four copies. The two benzene rings attached to the central thiazepinone are oriented nearly orthogonally to each other, giving the scaffold an L-shaped appearance. This moiety fits snugly into an L-shaped cavity contacting 4 hydrophobic residues (V215, L220, V222 and F267) on one side and a proline (P210) on the other. The cyclopropyl group fits into a shallow pocket defined by this Pro residue and by three other hydrophobic residues (C264, I274, F211). At the base of this cavity, residues Asn268 and Tyr225 on the BC and ZA loops form direct and water-mediated hydrogen bonds with the thiazepinone carbonyl group, respectively. The bound structure closely resembles the unbound structure of CaBdf1-BD1, with the notable exception that residue Ile274 adopts a different side chain conformation to accommodate the cyclopropyl group. Superimposing the structure of hBrd4 shows two Brd4 residues, Trp81 and Leu94, sterically hinder the binding of MS4. These residues correspond to CaBdf1 residues with smaller side chains (V209 and V222) that are compatible with MS4 binding, explaining the basis of inhibitor selectivity for the fungal BD.

Figure 13:
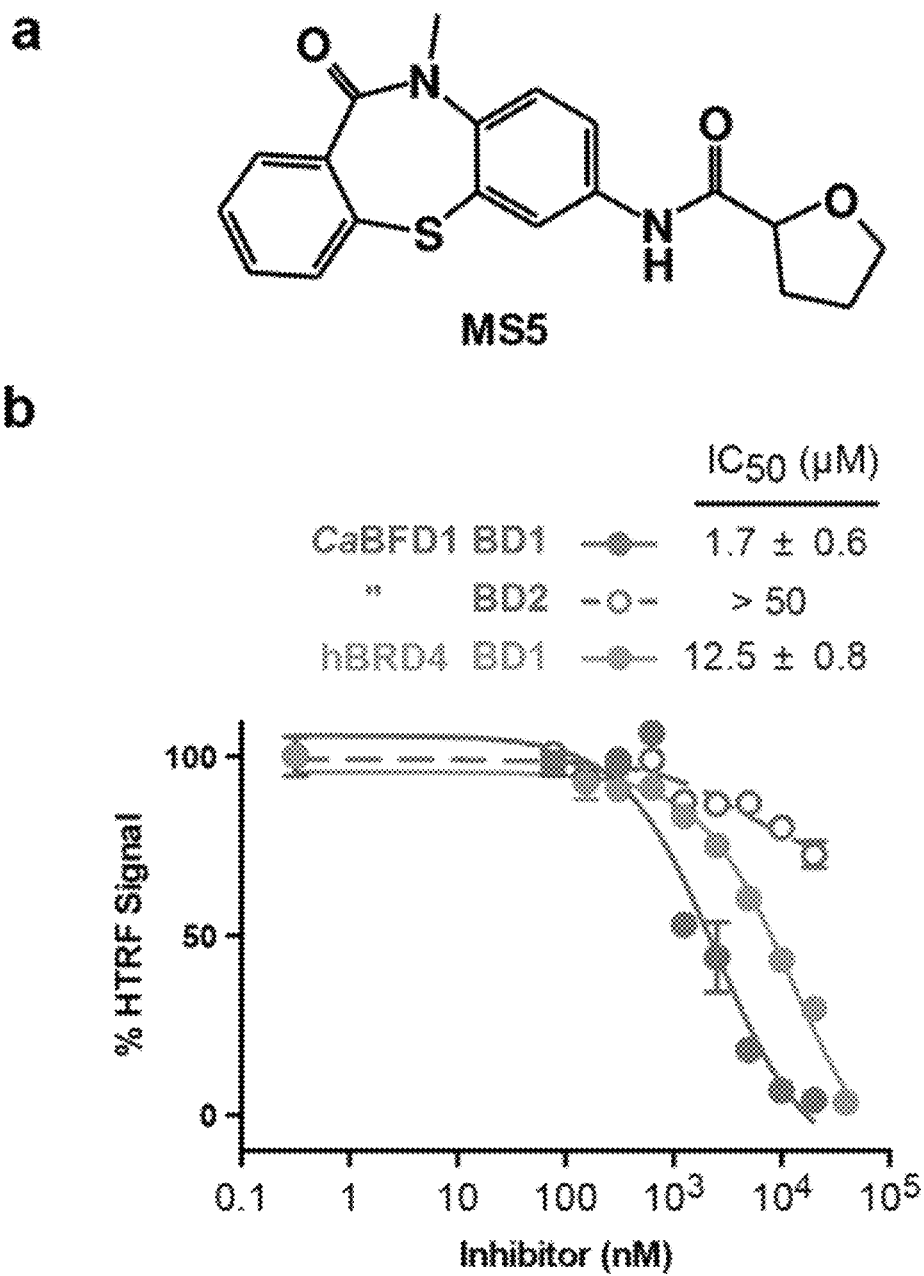
FIG. 13. Identification of a CaBdf1-BD1 inhibitor that phenocopies BD1 inactivation. (a) Chemical structure of dibenzothiazepinone compound MS5. (b) HTRF assay showing that MS5 inhibits CaBdf1-BD1 preferentially over CaBdf1-BD2 and with weak selectivity compared to hBrd4-BD1. (c) ITC experiment showing binding of MS5 towards the indicated BD. (d) Effect of MS5 on the growth of *C. albicans*. The first allele is indicated below the graph, the second is pMET-BDF1 (top) orpTetO-BDF1 (bottom). Strains were grown in the presence of doxycycline or methionine/cysteine, respectively, to repress expression from the second allele. MS5 compromises growth when CaBdf1-BD2 is inactivated by deletion or point-mutation. Statistical test is a two-sided paired t-test performed on ≥5 biological replicates (*p=0.01 to 0.05; p=0.001 to 0.01; *p<0.001). (e) Dose-response experiment showing the effect of MS5 on Bdf1 mutant strains.
Figure 13:
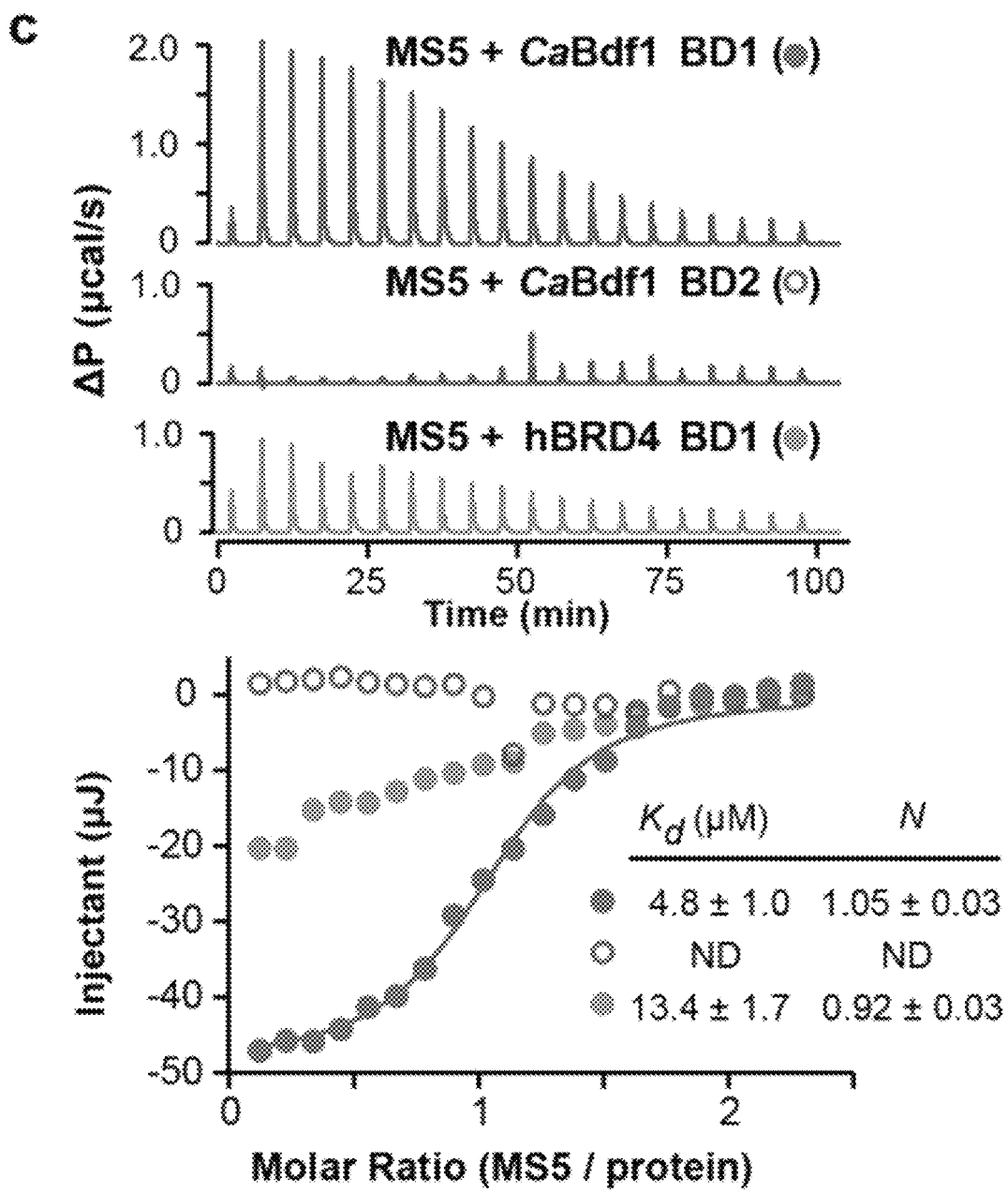
Figure 13:
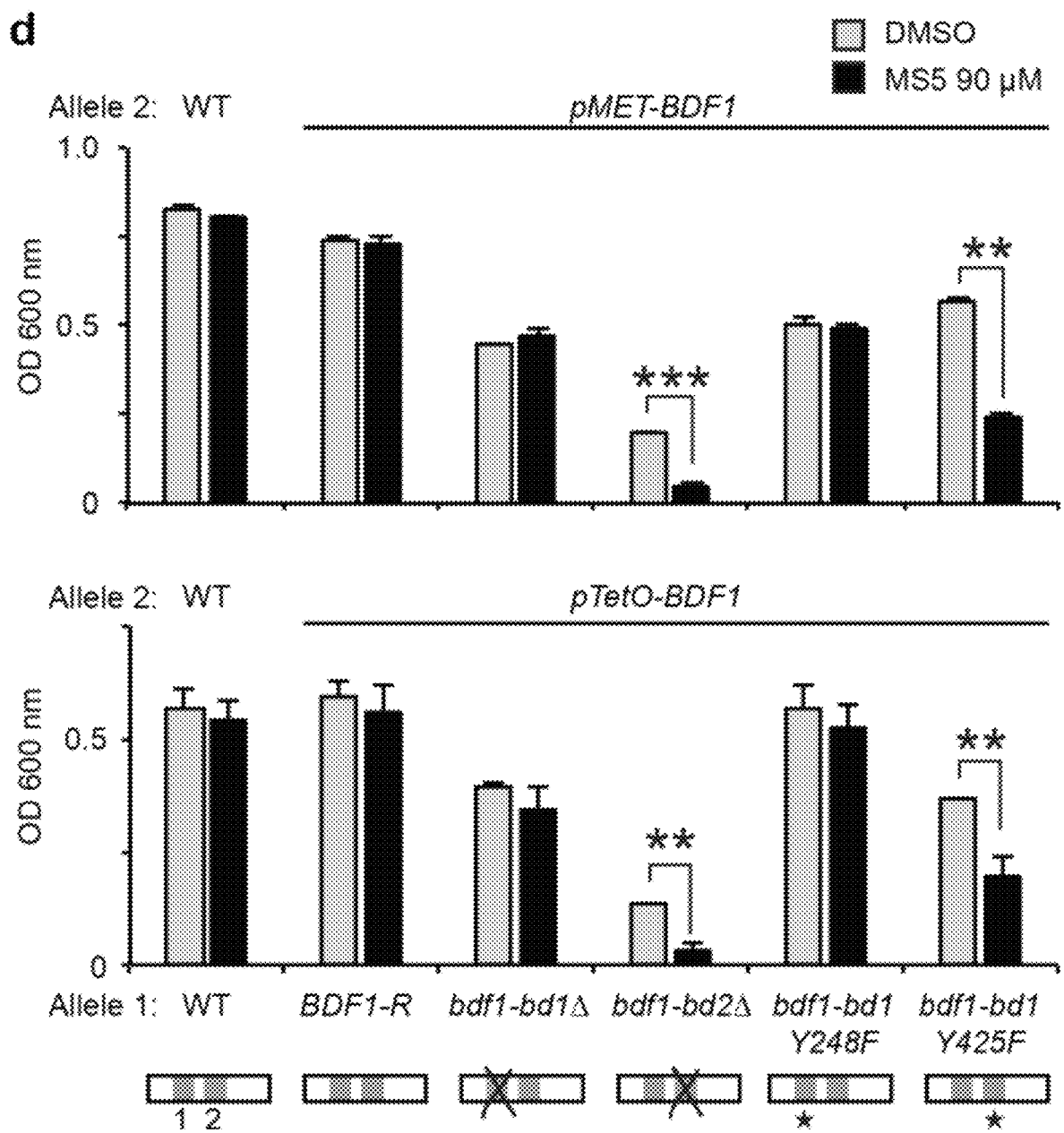
Figure 13:
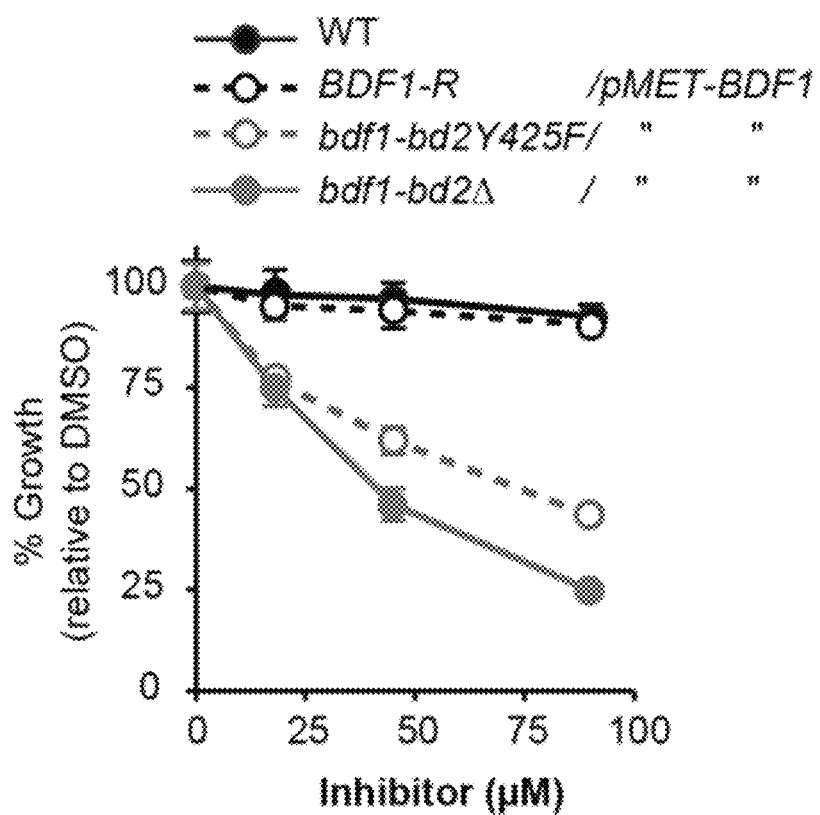

We next tested the effect of the identified hit compounds on the growth of *C. albicans* in vitro. Several compounds that showed significant selectivity towards CaBdf1, including MS4, had little effect. We therefore tested compounds that inhibited CaBdf1-BD1 with micromolar $IC_{50}$ values but which were unselective or only weakly selective for the fungal BD. These compounds include MS5, which compared to MS4, lacks the cyclopropyl group and has carboxyamidyl and tetrahydrofuran groups instead of the larger oxadiazole and pyrazine rings (FIG. 13a). HTRF and ITC assays show that MS5 inhibits CaBdf1-BD1 with low micromolar affinity, exhibits 3- to 5-fold selectivity relative to human Brd4-BD1 and has only a weak inhibitory effect on CaBdf1-BD2 (FIG. 13b, 13c). Growth assays in liquid culture show that, compared to vehicle (DMSO), MS5 has little effect on the growth of *C. albicans* strains expressing WT Bdf1 or mutant Bdf1 inactivated in the first BD, consistent with the specificity of this compound for BD1 and with the observation that a single functional copy of BD2 is sufficient to allow proper growth (FIG. 3e).

Figure 14:
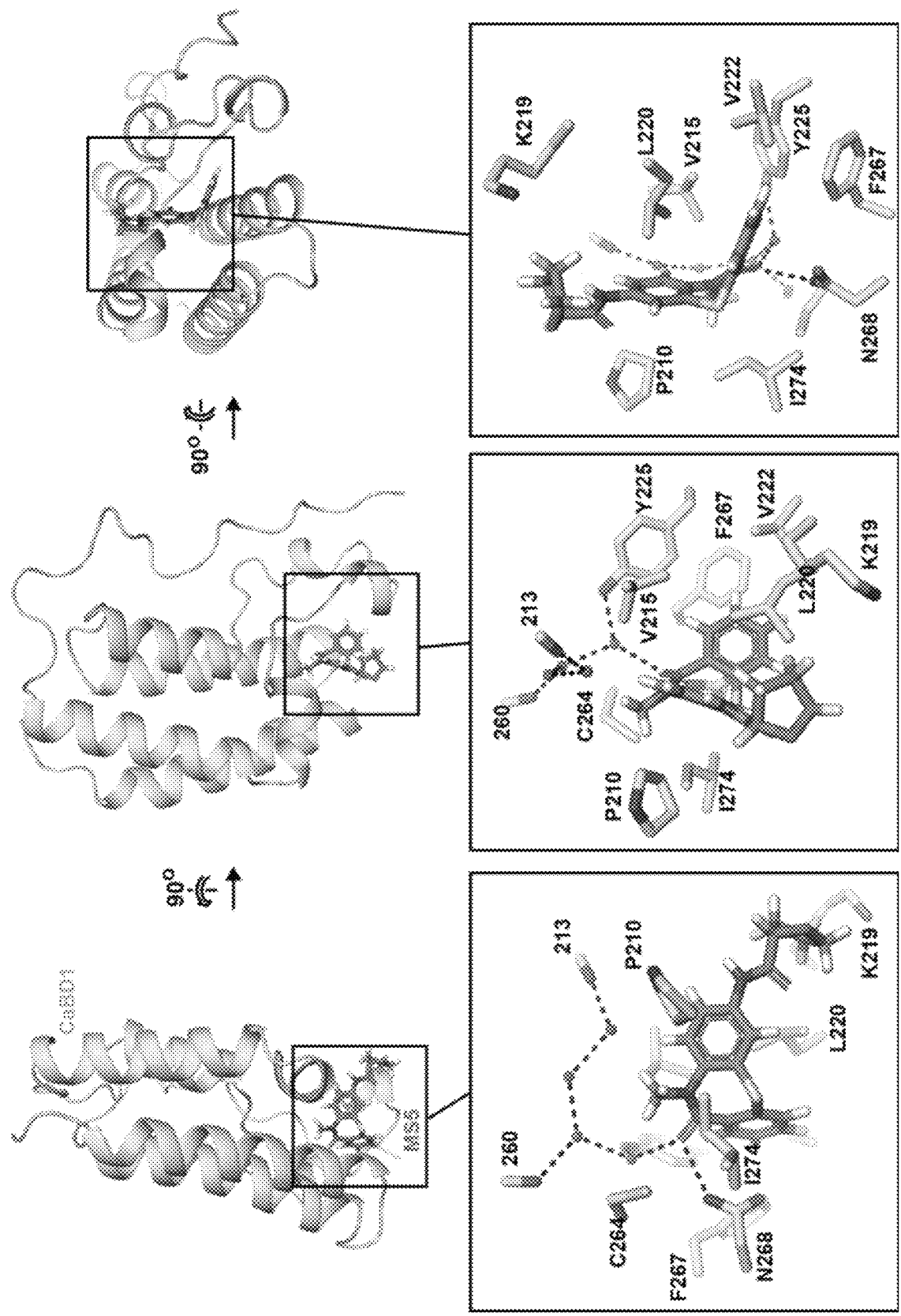
FIG. 14. MS5 recognition by CaBdf1-BD1. Three orthogonal views of the complex are shown. Insets show the residue environment of M5 within the active site.

In contrast, MS5 significantly compromised the growth of strains inactivated in BD2 (FIG. 13d). A dose-response curve revealed an $IC_{50}$ value of 40 µM, which is approximately 8-fold higher than $K_d$ determined in vitro (FIG. 13c). This discrepancy may be due to inefficient crossing of the fungal cell wall by MS5 or to metabolism/secretion of the compound by the cell. The crystal structure of CaBdf1-BD1 bound to MS5 is shown in FIG. 14. The structure explains the lack of selectivity towards hBrd4-BD1.

Figure 15:
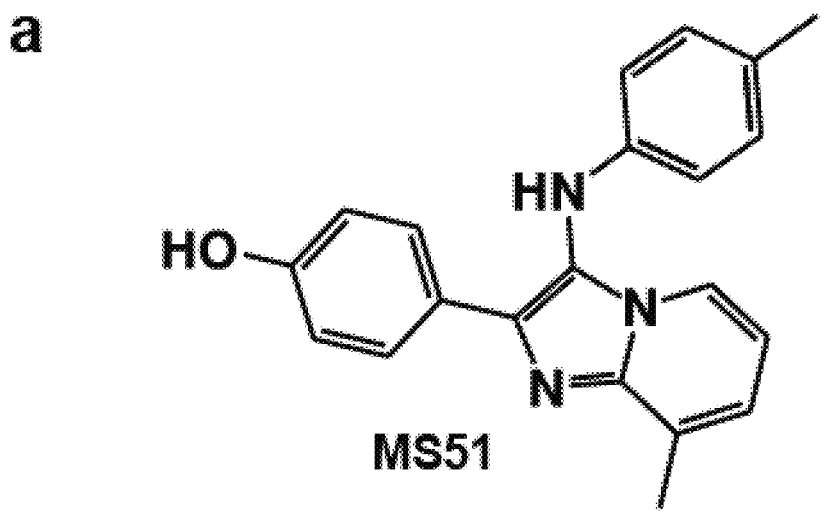
FIG. 15. Identification of a selective inhibitor of *C. albicans* Bdf1 BD2. (a) Chemical structure of compound MS51. (b) HTRF assays showing selective inhibition of CaBdf1 BD2 by MS51. (c) ITC experiment showing binding of MS51 to CaBdf1 BD1. (d) Structural basis of MS51 recognition.
Figure 15:
Figure 15:
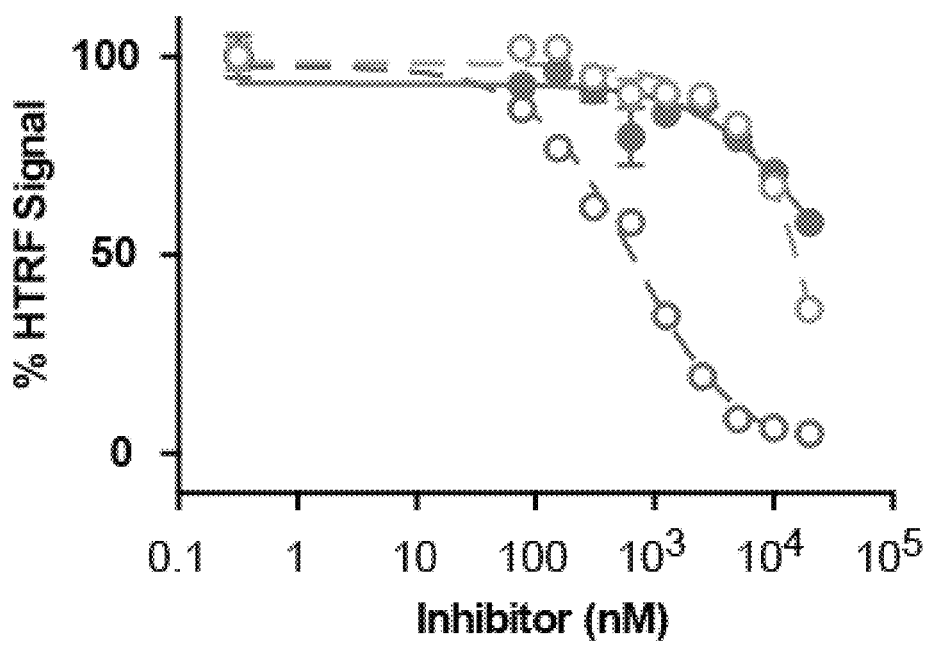
Figure 15:
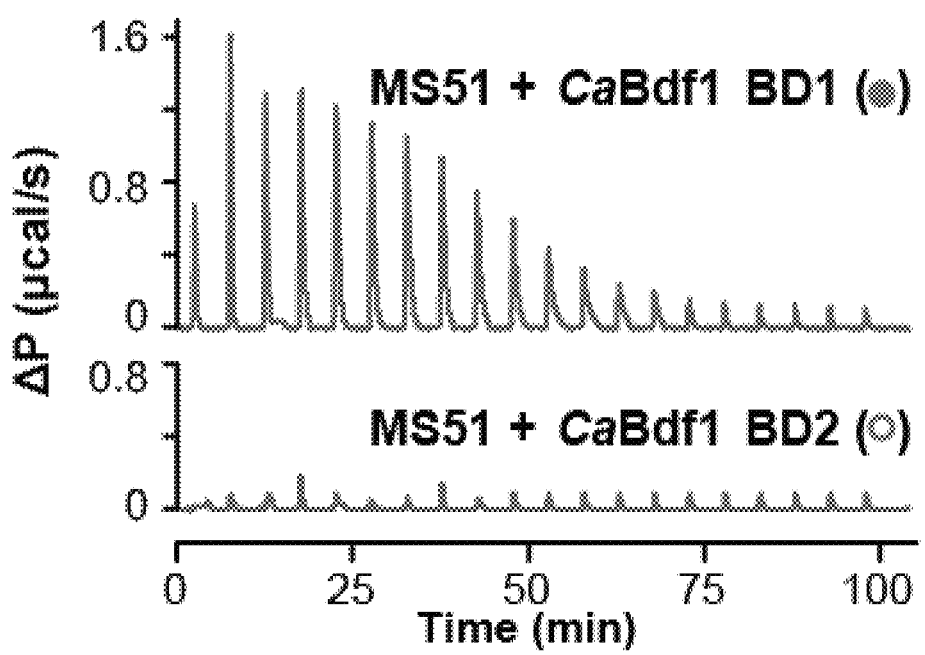
Figure 15:
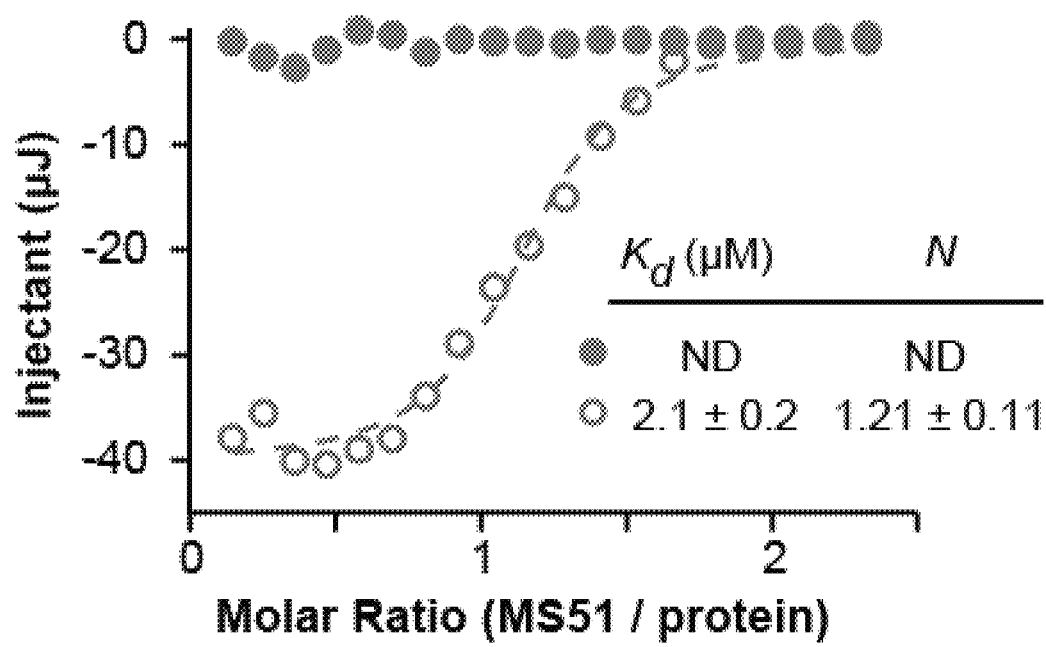
Figure 15:
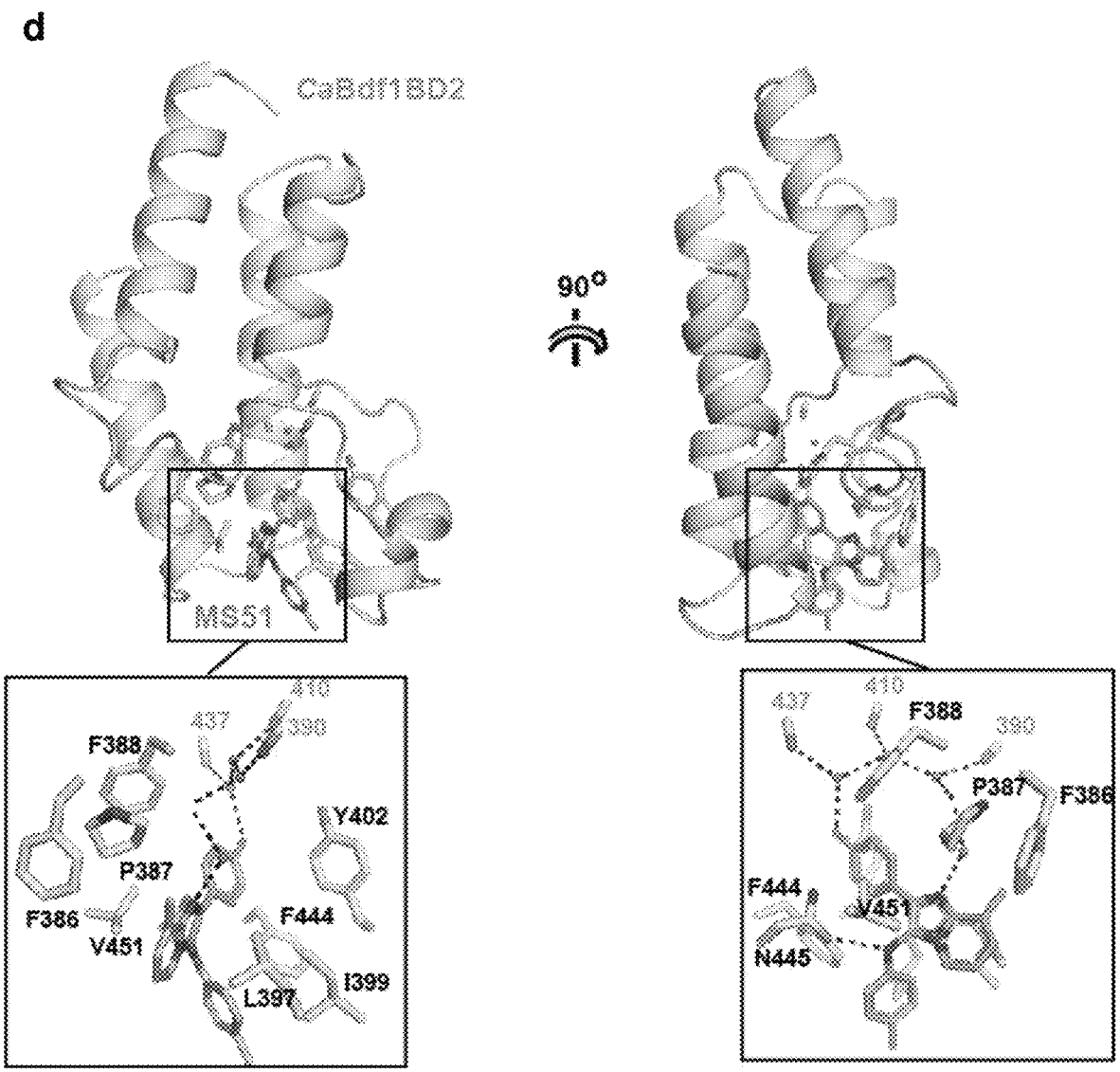

Similarly, we identified a compound, MS51, which inhibited CaBdf1-BD2 with high selectivity relative to BD1 of either CaBdf1 or human Brd4 (FIG. 15a). HTRF and ITC assays showed that MS51 binds CaBdf1-BD2 with 1-2 µM affinity (FIG. 15b, 15c). The high-resolution crystal structure of CaBdf1-BD2 bound to MS51 reveals the structural basis of binding selectivity towards the fungal domain.

Taken together, the above data show that Bdf1 BD function is required for proper growth and pathogenesis of *C. albicans*, and that these domains can be targeted with small-molecule compounds in a selective manner relative to human BDs. These findings pave the way for the development of BET BD inhibitors as a novel class of anti-fungal therapeutics.

Example 2. Preparation of Various Compounds of the Disclosure

Materials and Methods. 1-Chloro-2,4-dinitrobenzene, 2-mercaptobenzoic acid, (R)-tetrahydrofuran-2-carboxylic acid and (S)-tetrahydrofuran-2-carboxylic acid were purchased from Sigma-Aldrich. 2-Bromo-1-(4-hydroxyphenyl)ethan-1-one, 2-bromo-1-(4-fluorophenyl)ethan-1-one and 3-methylpyridin-2-amine were purchased from TCI America. P-toluidine was purchased from Alfa Aesar. 2-Bromo-1-phenylethan-1-one was purchased from Oxchem Corp. All other reagents were purchased from commercial sources and used as obtained. Compounds were synthesized as described below. $^1H$, $^{19}F$ NMR spectra were obtained on Varian 400-MR and VNMRS-600 NMR Spectrometers. The chemical shifts are relative to external hexafluorobenzene, $C_6F_6$ (δ–164.9, $^{19}F$ NMR). Multiplicities are quoted as singlet (s), doublet (d), triplet (t) unresolved multiplet (m), doublet of doublets (dd), doublet of doublet of doublets (ddd), doublet of triplets (dt) or broad signal (br). All chemical shifts are given on the δ-scale in parts per million (ppm) relative to internal CD$_2$HOD (δ 3.34, $^1$H NMR), CHCl$_3$ (δ 7.26, $^1$H NMR). $^1$H, $^{19}$F coupling constants (J value) are given in Hz. The concentration of the NMR samples was in the range of 4-6 mg/mL. Normal phase chromatography was performed using ISCO Combiflash Lumen+. UV and ELS detectors were used. Mass Spectrometry (MS) was performed on a Finnigan LCQ Deca XP Max mass spectrometer equipped with an ESI source in the negative ion mode. The IUPAC names of compounds were assigned using Chemdraw. All the NMRs were processed and interpreted using MestReNova 9.0.0.

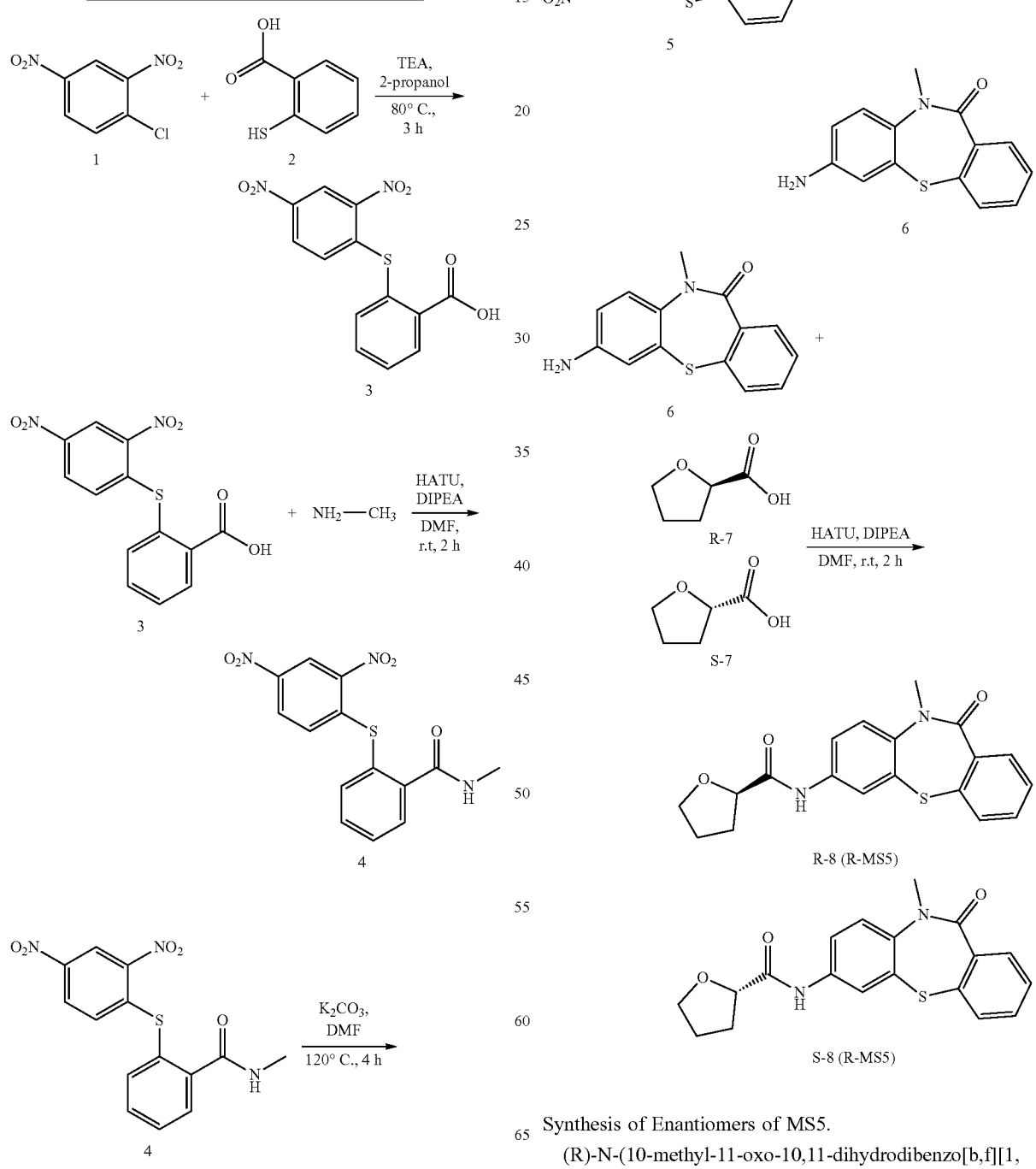

Synthesis of Enantiomers of MS5.

(R)-N-(10-methyl-11-oxo-10,11-dihydrodibenzo[b,f][1,4]thiazepin-7-yl)tetrahydrofuran-2-carboxamide:

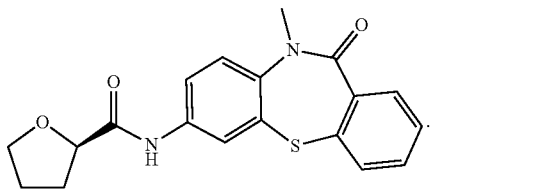

(S)-N-(10-methyl-11-oxo-10,11-dihydrodibenzo[b,f][1,4]thiazepin-7-yl)tetrahydrofuran-2-carboxamide:

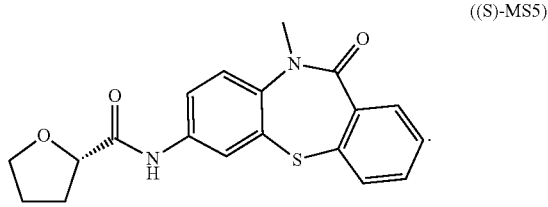 [SMILES: CN1C(=O)c2ccccc2Sc2cc(NC(=O)[C@@H]3CCCO3)ccc21]

1-Chloro-2,4-dinitrobenzene (0.5 g, 2.5 mmol, 1 equiv.) and 0.38 g (2.5 mmol, 1 equiv.) 2-mercaptobenzoic acid were added to a mixture of 0.68 mL TEA and 3.7 mL 2-propanol. The mixture was heated to 80° C. with vigorous stirring for 3 hr. The product was extracted with EtOAc (5 mL×3). The solvent was then removed under vacuum to get the product (2-((2,4-dinitrophenyl)thio)benzoic acid, 90% yield) for the next step. 0.5 g (1.6 mmol, 1 equiv.) 2-((2,4-dinitrophenyl)thio)benzoic acid was added to 8.25 mL DMF. 0.713 g (1.2 equiv.) HATU and 0.404 g (2 equiv.) DIEA were then added to the solution. 0.0586 g (1.1 equiv.) $NH_2CH_3$ was also added to the mixture. The reaction mixture was stirred vigorously at RT for 2 hr. The product was extracted with EtOAc (5 mL×3) and dried under vacuum (70% yield). 0.26 g (1 equiv.) of the product and 0.04 g (2 equiv.) $K_2CO_3$ were then placed in a 10 mL round bottom flask with 2 mL DMF. The mixture was kept at 120° C. (oil bath) with vigorous stirring for 4 hr. After solvent removal in vacuum the resulting compound was washed with DI water and EtOH and dried to get the product (49% yield). 95 mg (1 equiv.) of the resulting product was dissolved in EtOAc (3 mL) and mixture of 1 mL EtOH and 300 μL (7 equiv.) 30% HCl was then added to the solution. Finally, 0.262 g (3.5 equiv.) $SnCl_2$ was added to the reaction mixture. The mixture was heated at 80° C. with vigorous stirring for 2 hr. After reaction completion (monitored by TLC) the pH was adjusted to 11 with NaOH. Formed precipitate was washed 3 times with water and dried under vacuum. Yield 42%. Then 32 mg (1 equiv.) of the formed product and 15.44 mg (1.1 equiv.) (R)-tetrahydrofuran-2-carboxylic acid (or (S)-tetrahydrofuran-2-carboxylic acid) were dissolved in 1 mL DMF. 54.75 mg (1.2 equiv.) HATU and 31.02 mg (2 equiv.) DIEA were then added to the solution. The reaction was vigorously stirred at RT for 2 hr. Product was extracted by EtOAc (5 mL×3) and dried under vacuum. Final compound (R-MS5 or S-MS5) was obtained with 42% yield (18.4 mg).

The R-enantiomer of MS5. $^1$H NMR (600 MHz, Chloroform-d) δ 8.47 (s, 1H), 7.81 (dd, J=46.3, 2.5 Hz, 1H), 7.75-7.69 (m, 1H), 7.59 (ddd, J=49.7, 8.7, 2.5 Hz, 1H), 7.42 (dt, J=7.3, 2.1 Hz, 1H), 7.34-7.27 (m, 2H), 7.25 (d, J=2.7 Hz, 1H), 4.43 (dd, J=8.4, 5.9 Hz, 1H), 4.00 (t, J=7.2 Hz, 1H), 3.94 (q, J=7.3 Hz, 1H), 3.58 (s, 3H), 2.35 (dd, J=13.4, 7.3 Hz, 1H), 2.13 (tt, J=8.2, 2.9 Hz, 1H), 2.00-1.83 (m, 2H). Calculated for $C_{19}H_{18}N_2O_3S$: 354.10, Mass found: 355.3 (M+H$^+$); 709.0 (2M+H$^+$); 731.1 (2M+Na$^+$).

The S-enantiomer of MS5. $^1$H NMR (400 MHz, Chloroform-d) δ 8.51 (s, 1H), 7.83 (dd, J=30.2, 2.5 Hz, 1H), 7.77-7.68 (m, 1H), 7.60 (ddd, J=32.9, 8.7, 2.5 Hz, 1H), 7.47-7.40 (m, 1H), 7.34-7.25 (m, 3H), 4.44 (dd, J=8.4, 5.9 Hz, 1H), 4.02 (qd, J=7.1, 1.1 Hz, 1H), 3.98-3.89 (m, 1H), 3.59 (s, 3H), 2.85 (s, 2H), 2.42-2.30 (m, 1H), 2.20-2.08 (m, 1H), 1.94 (dtt, J=19.6, 12.6, 6.7 Hz, 2H). Calculated for $C_{19}H_{18}N_2O_3S$: Mass found: 355.6 (M+H$^+$); 377.4 (M+Na$^+$); 730.9 (2M+Na$^+$).

As would be readily recognized by one of skill in the art, substituted dibenzothiazepinones can be prepared by appropriate modification of the route and techniques described in Scheme 1. Importantly, the oxadiazole moiety is not determinative for selectivity, as several hits in this group were not selective. The most active compound bears a cyclopropyl group on the lactam nitrogen of the dibenzothiazepinone scaffold (R in Scheme 2). Several other hits also have a cyclopropyl at the same position; however, in some cases the presence of a methyl group results in higher potency.

Scheme 2. Synthesis of substituted dibenzothiazepinones.

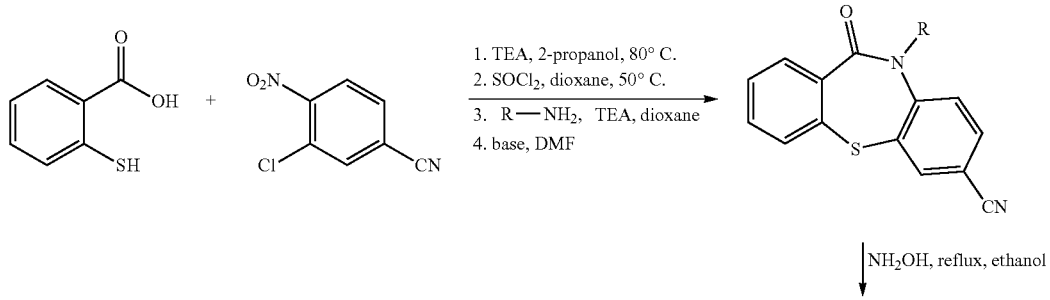

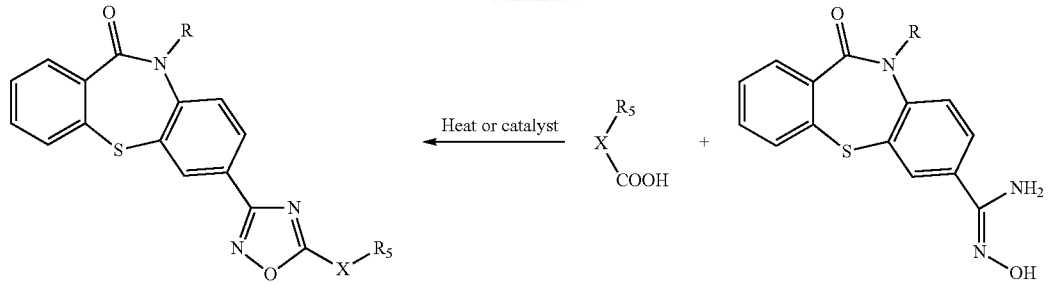

where R and $R_5$ are as defined herein, and X is a direct bond or L as defined herein (e.g., as for Formula I).

For example, 2-mercaptobenzoic acid can be reacted with 3-chloro-4-nitrobenzonitrile and various substituted amines to form the dibenzothiazepinone scaffold via denitrocyclization, followed by formation of amidoxime by reaction of nitrile moiety with hydroxylamine in a suitable solvent such as ethanol (Eloy et al., *Chem. Rev.* 1962; 62(2):155-83), and finally formation of 3,5-disubstituted 1,2,4-oxadiazole moiety by reaction of amidoxime with various substituted acids in the presence of catalysts or heat (Augustine et al., *J. Org. Chem.* 2009; 74(15):5640-3).

The highly most potent compounds in this subfamily (Scheme 2) bear an aromatic ring (—X—$R_2$) in position 5 on the oxadiazole ring that can modulate selectivity. A variety of different aromatic rings can be installed at this position (X in Scheme 2) to achieve high activity and selectivity. Further modification includes substitution on this aromatic ring. Compounds of Formula IV can be synthesized according to Scheme 2, starting from commercially available reagents and/or by techniques know to those of skill in the art.

General Procedure for Synthesis of MS51 Variation Compounds.

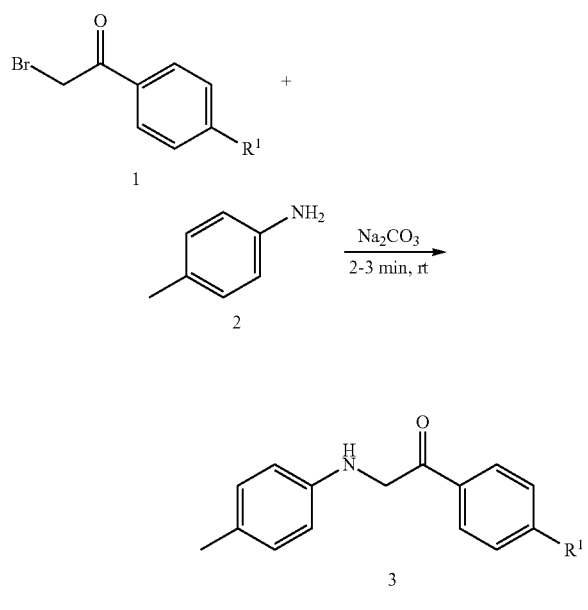

Scheme 3. Synthesis of MS-51 variation compounds.

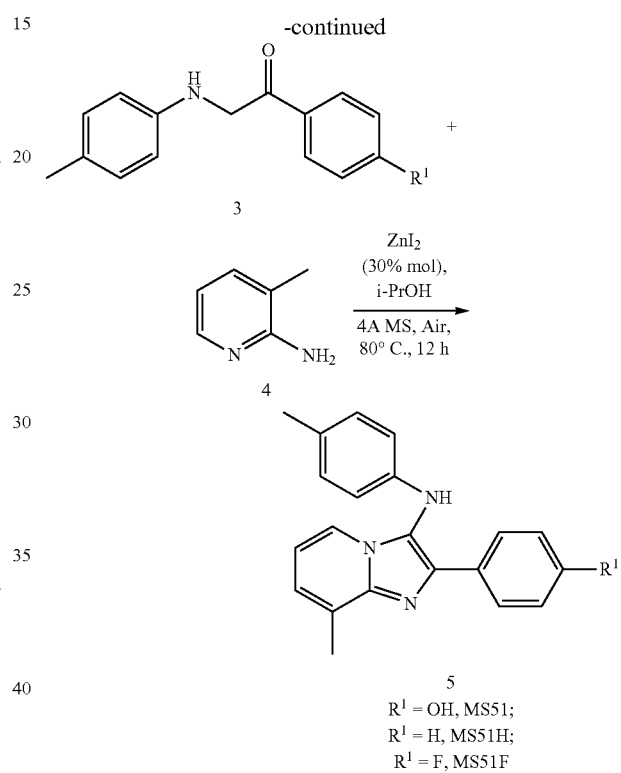

2 mmol (1 equiv) of corresponding 2-bromoacetophenone and 0.235 g (2.2 mmol, 1.1 equiv.) p-toluidine were added to a flask. 0.1 g $Na_2CO_3$ was added and the mixture was grinded for 2 min at RT until it became yellow. The crude material was washed 3 times with water and dried under the vacuum giving of solid material with yields 80-90%. 1 mmol (1 equiv.) of the solid material was then dissolved in 6 mL isopropyl alcohol and 0.108 g 3-methylpyridin-2-amine (1 mmol, 1 equiv.) was added dropwise to the solution. Finally, 0.1 g $ZnI_2$ and 0.5 g 4 Å molecular sieves were added. The mixture was heated at 80° C. with vigorous stirring for 12 hr. After reaction completion (by TLC), the product was extracted with EtOAc (5 mL×3) and washed with DI water (5 mL×3). The organic layer was dried over $Na_2SO_4$ and the solvent was removed under vacuum. The resulting product was further purified by silica gel column chromatography (0-90% EtOAc/Hexane), giving target compounds with yields 18-24%.

8-Methyl-2-phenyl-N-(p-tolyl)imidazo[1,2-a]pyridin-3-amine, MS51-H

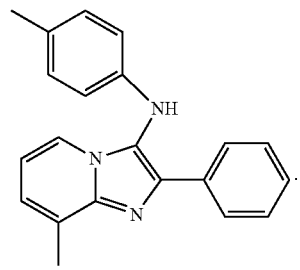

(MS51H)

$^1$H NMR (400 MHz, Methanol-d4) δ 7.97-7.91 (m, 2H), 7.88 (d, J=6.7 Hz, 1H), 7.41-7.35 (m, 2H), 7.34-7.30 (m, 1H), 7.23 (dt, J=6.9, 1.1 Hz, 1H), 6.96 (d, J=8.0 Hz, 2H), 6.89 (t, J=6.8 Hz, 1H), 6.48-6.36 (m, 2H), 2.65 (s, 3H), 2.20 (s, 3H). Calculated for $C_{21}H_{19}N_3$: 313.16 Mass found: 314.5 (M+H$^+$).

4-(8-Methyl-3-(p-tolylamino)imidazo[1,2-a]pyridin-2-yl)phenol, MS51

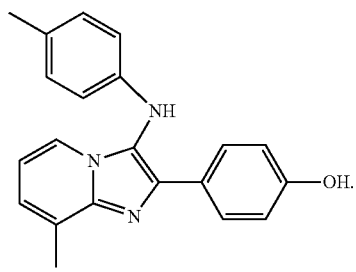

(MS51)

$^1$H NMR (400 MHz, Methanol-d4) δ 7.79 (d, J=8.5 Hz, 3H), 7.11 (d, J=6.8 Hz, 1H), 6.94 (d, J=8.4 Hz, 2H), 6.81-6.75 (m, 3H), 6.42 (d, J=8.4 Hz, 2H), 2.62 (s, 3H), 2.20 (s, 3H). Calculated for $C_{21}H_{19}N_3O$: 329.15 Mass found: 330.4 (M+H$^+$).

2-(4-Fluorophenyl)-8-methyl-N-(p-tolyl)imidazo[1,2-a]pyridin-3-amine, Also Called MS51F

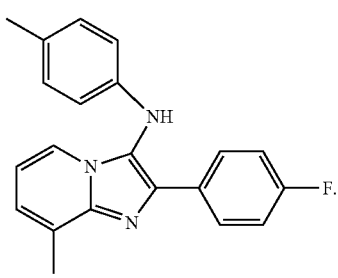

(MS51F)

$^1$H NMR (400 MHz, Chloroform-d) δ 8.01 (dd, J=8.8, 5.5 Hz, 2H), 7.69 (d, J=6.7 Hz, 1H), 7.06-6.95 (m, 5H), 6.69 (t, J=6.8 Hz, 1H), 6.49 (d, J=8.4 Hz, 2H), 2.68 (s, 3H), 2.25 (s, 3H). $^{19}$F NMR (564 MHz, Chloroform-d) δ −105.23, −106.62, −114.35. Calculated for $C_{21}H_{18}FN_3$: 331.15 Mass found: 332.3 (M+H$^+$).

Citations for Examples 1 and 2

The following publications are incorporated by reference herein in their entireties:

1 Brown, G. D. et al. Hidden killers: human fungal infections. *Sci Transl Med* 4, 165rv113 (2012).
2 Fungal_Research_Trust. in *Fungal Research Trust 20th Anniversary meeting*. (London, 2011).
3 Arendrup, M. C. Epidemiology of invasive candidiasis. *Curr Opin Crit Care* 16, 445-452 (2010).
4 Moran, C., Grussemeyer, C. A., Spalding, J. R., Benjamin, D. K., Jr. & Reed, S. D. *Candida albicans* and non-*albicans* bloodstream infections in adult and pediatric patients: comparison of mortality and costs. *Pediatr Infect Dis J* 28, 433-435 (2009).
5 Pound, M. W., Townsend, M. L., Dimondi, V., Wilson, D. & Drew, R. H. Overview of treatment options for invasive fungal infections. *Med Mycol* 49, 561-580 (2011).
6 Lewis, R. E. Current concepts in antifungal pharmacology. *Mayo Clin Proc* 86, 805-817 (2011).
7 Roemer, T. & Krysan, D. J. Antifungal drug development: challenges, unmet clinical needs, and new approaches. *Cold Spring Harb Perspect Med* 4 (2014).
8 Armstrong-James, D., Meintjes, G. & Brown, G. D. A neglected epidemic: fungal infections in HIV/AIDS. *Trends Microbiol* 22, 120-127 (2014).
9 Denning, D. W. & Bromley, M. J. *Infectious Disease*. How to bolster the antifungal pipeline. *Science* 347, 1414-1416 (2015).
10 Hnisz, D., Tscherner, M. & Kuchler, K. Targeting chromatin in fungal pathogens as a novel therapeutic strategy: histone modification gets infectious. *Epigenomics* 3, 129-132 (2011).
11 Smith, W. L. & Edlind, T. D. Histone deacetylase inhibitors enhance *Candida albicans* sensitivity to azoles and related antifungals: correlation with reduction in CDR and ERG upregulation. *Antimicrob Agents Chemother* 46, 3532-3539 (2002).
12 Pfaller, M. A. et al. Activity of MGCD290, a Hos2 histone deacetylase inhibitor, in combination with azole antifungals against opportunistic fungal pathogens. *J Clin Microbiol* 47, 3797-3804 (2009).
13 Pfaller, M. A., Rhomberg, P. R., Messer, S. A. & Castanheira, M. In vitro activity of a Hos2 deacetylase inhibitor, MGCD290, in combination with echinocandins against echinocandin-resistant *Candida* species. *Diagn Microbiol Infect Dis* 81, 259-263 (2015).
14 Kmetzsch, L. Histone deacetylases: Targets for antifungal drug development. *Virulence* 6, 535-536 (2015).
15 Nishikawa, J. L. et al. Inhibiting fungal multidrug resistance by disrupting an activator-Mediator interaction. *Nature* 530, 485-489 (2016).
16 Filippakopoulos, P. & Knapp, S. Targeting bromodomains: epigenetic readers of lysine acetylation. *Nat Rev Drug Discov* 13, 337-356 (2014).
17 Moriniere, J. et al. Cooperative binding of two acetylation marks on a histone tail by a single bromodomain. *Nature* 461, 664-668 (2009).
18 Filippakopoulos, P. et al. Histone recognition and large-scale structural analysis of the human bromodomain family. *Cell* 149, 214-231 (2012).

19 Brand, M. et al. Small Molecule Inhibitors of Bromodomain-Acetyl-lysine Interactions. *ACS Chem Biol* 10, 22-39 (2015).
20 Shi, J. & Vakoc, C. R. The mechanisms behind the therapeutic activity of BET bromodomain inhibition. *Mol Cell* 54, 728-736 (2014).
21 Schaefer, U. Pharmacological inhibition of bromodomain-containing proteins in inflammation. *Cold Spring Harb Perspect Biol* 6 (2014).
22 Gallenkamp, D., Gelato, K. A., Haendler, B. & Weinmann, H. Bromodomains and their pharmacological inhibitors. *ChemMedChem* 9, 438-464 (2014).
23 Ladurner, A. G., Inouye, C., Jain, R. & Tjian, R. Bromodomains mediate an acetyl-histone encoded anti-silencing function at heterochromatin boundaries. *Mol Cell* 11, 365-376 (2003).
24 Matangkasombut, O. & Buratowski, S. Different sensitivities of bromodomain factors 1 and 2 to histone H4 acetylation. *Mol Cell* 11, 353-363 (2003).
25 Matangkasombut, O., Buratowski, R. M., Swilling, N. W. & Buratowski, S. Bromodomain factor 1 corresponds to a missing piece of yeast TFIID. *Genes Dev* 14, 951-962 (2000).
26 Kobor, M. S. et al. A protein complex containing the conserved Swi2/Snf2-related ATPase Swr1p deposits histone variant H2A.Z into euchromatin. *PLoS Biol* 2, E131 (2004).
27 Govin, J. et al. Systematic screen reveals new functional dynamics of histones H3 and H4 during gametogenesis. *Genes Dev* 24, 1772-1786 (2010).
28 Fu, J. et al. The Yeast BDF1 Regulates Endocytosis via LSP1 Under Salt Stress. *Current microbiology* (2015).
29 Liu, X. et al. Genetic and comparative transcriptome analysis of bromodomain factor 1 in the salt stress response of *Saccharomyces cerevisiae*. *Current microbiology* 54, 325-330 (2007).
30 Durant, M. & Pugh, B. F. NuA4-directed chromatin transactions throughout the *Saccharomyces cerevisiae* genome. *Mol Cell Biol* 27, 5327-5335 (2007).
31 Lygerou, Z. et al. The yeast BDF1 gene encodes a transcription factor involved in the expression of a broad class of genes including snRNAs. *Nucleic Acids Res* 22, 5332-5340 (1994).
32 Chua, P. & Roeder, G. S. Bdf1, a yeast chromosomal protein required for sporulation. *Mol Cell Biol* 15, 3685-3696 (1995).
33 Liu, X. et al. Bdf1p deletion affects mitochondrial function and causes apoptotic cell death under salt stress. *FEMS Yeast Res* 9, 240-246 (2009).
34 Roemer, T. et al. Large-scale essential gene identification in *Candida albicans* and applications to antifungal drug discovery. *Molecular microbiology* 50, 167-181 (2003).
35 Xu, Q. R. et al. Molecular genetic techniques for gene manipulation in *Candida albicans*. *Virulence* 5, 507-520 (2014).
36 Vidler, L. R., Brown, N., Knapp, S. & Hoelder, S. Druggability analysis and structural classification of bromodomain acetyl-lysine binding sites. *J Med Chem* 55, 7346-7359 (2012).
37 Lai, W. C., Sun, H. F., Lin, P. H., Ho Lin, H. L. & Shieh, J. C. A new rapid and efficient system with dominant selection developed to inactivate and conditionally express genes in *Candida albicans*. *Curr Genet* 62, 213-235 (2016).

Example 3. Preparation of Dual Warhead Compounds

Because *C. albicans* strains inactivated in only one Bdf1 BD retain some viability, a monotherapy strategy targeting CaBdf1 may require the inhibition of both BDs to be highly effective, at least for *C. albicans*. Monotherapy may, however, be effective for *C. glabrata* and other species. Additionally, inhibition of a single BD, preferably BD2 in the case of *C. albicans*, may be effective in a combination therapy strategy against, e.g. a fluconazole-resistant *Candida* strain. CaBdf1 can also be inhibited via a single compound that targets both BDs (e.g., compounds of Formula IV). Such dual-warhead BET inhibitors that simultaneously engage both BDs within a single BET protein will be highly effective for treating a variety of fungal infections.

Multivalent small-molecule drugs are innovative solution for proteins that offer two proximal and druggable binding sites, leading to exceptionally potent net overall binding of host and guest. This so-called avidity effect can significantly exceed the sum of its contributing components, resulting in orders of magnitude increase in binding relative to the affinity associated with the individual interactions. The linker length of compound of Formula IV and points of attachment can be optimized by varying the length of the linked that links the two heterocyclic moieties. We have designed novel dual-warhead CaBdf1 inhibitors (A1 and B1) which combine the dibenzothiazepinone (Formula I) and imidazopyridine (Formula II) pharmacophores in the correct spatial relationship. We have docked "Janus inhibitors" A1 and B1 separately to the CaBdf1 BD1 and BD2 binding pockets. Both compounds showed excellent ICM binding scores (Molsoft ICM Pro, ligand docking) and ideal fits into their respective pockets.

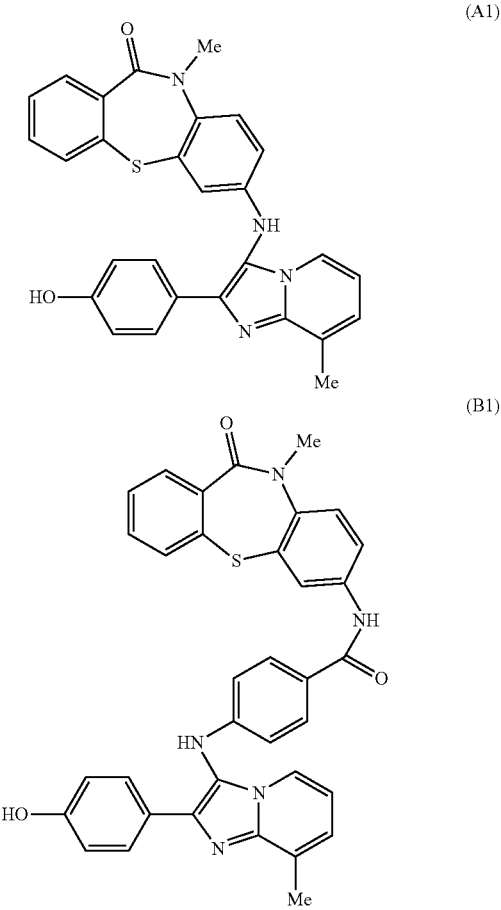

The prototype dual-warhead inhibitor (B1) can be synthesized via conjugation of 7-amino-10-methyldibenzo[b,f][1,4]thiazepin-11(10H)-one 6 (Smirnov et al., *J. Het. Chem.* 2007; 44(6): 1247-51) and 4-((2-(4-hydroxyphenyl)-8-methylimidazo[1,2-a]pyridin-3-yl)amino)benzoic acid 7 (Scheme 3-1).

unsatisfactory yields, standard protecting groups can be installed at the onset of the synthesis and removed at the end (see Wuts, *Greene's Protective Groups in Organic Synthesis*. 5th Ed: Wiley; 2014).

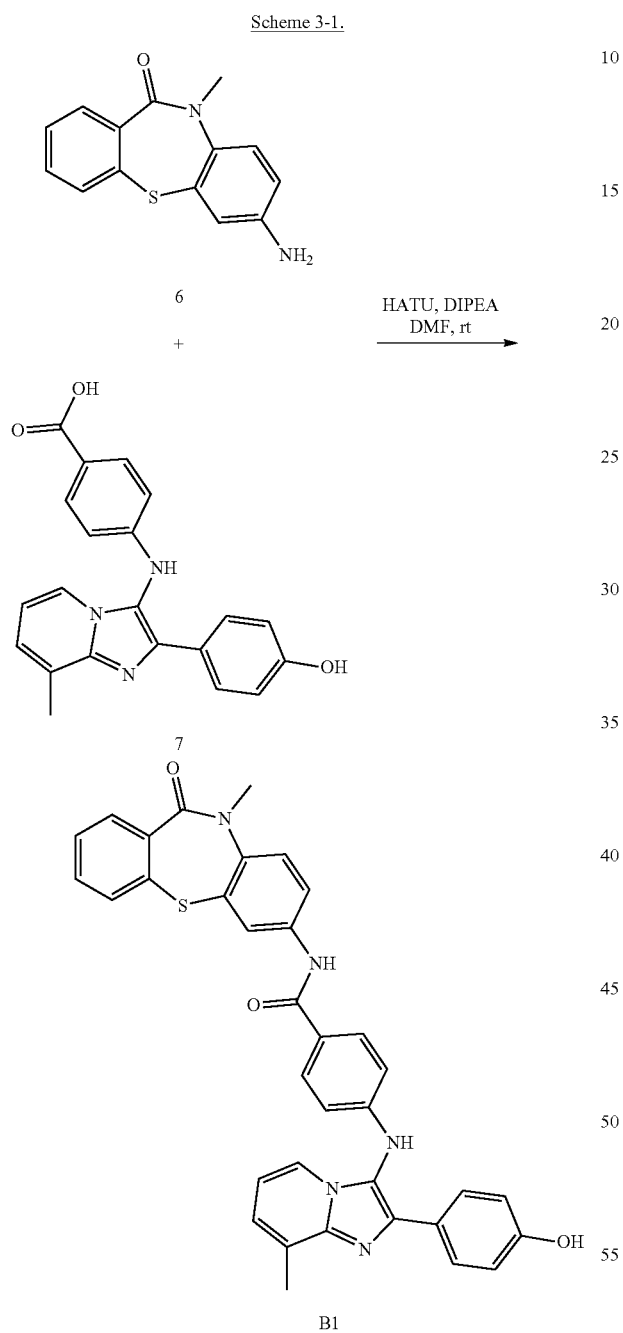

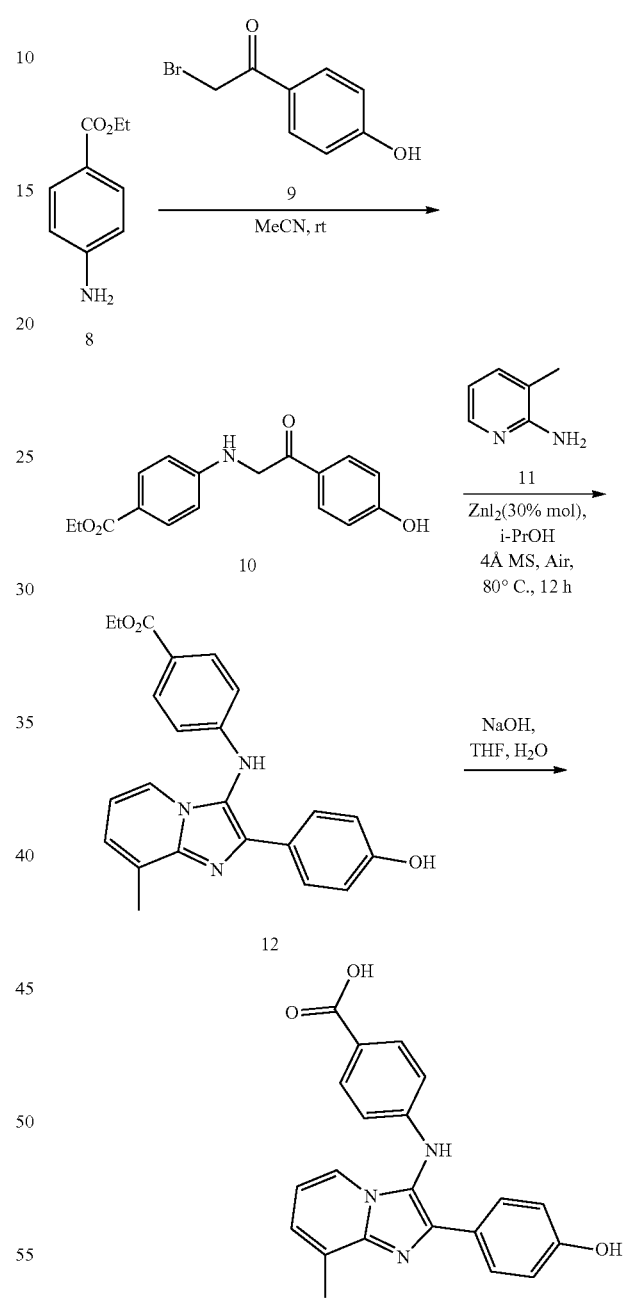

Compound 7 can be synthesized from reagents available commercially by adapting methods developed by Lakner (Lakner et al., *Synthesis-Stuttgart* 2009(12): 1987-90) and Han (Han et al., *Synthesis-Stuttgart* 2016; 48(3):351-6), as depicted in Scheme 3-2. The final inhibitor B1 can then be prepared via HATU-mediated amide bond formation between 6 and 7 (Scheme 3-1). Alternatively, if the unprotected phenol or secondary amine present in 7 results in The synthesis of A1 can utilize the same route to 3-aminoimidazopyridines 12. The known synthon 6 (Smirnov et al., *J. Het. Chem.* 2007; 44(6):1247-51) can be reacted with α-bromoketone 9 to form the α-aminoketone 13, which can be converted into A1 via zinc iodide catalysis following the literature method (Scheme 3-3) (Lipinski, *Drug Discov. Today Technol.* 2004; 1(4):337-41).

Scheme 3-3.

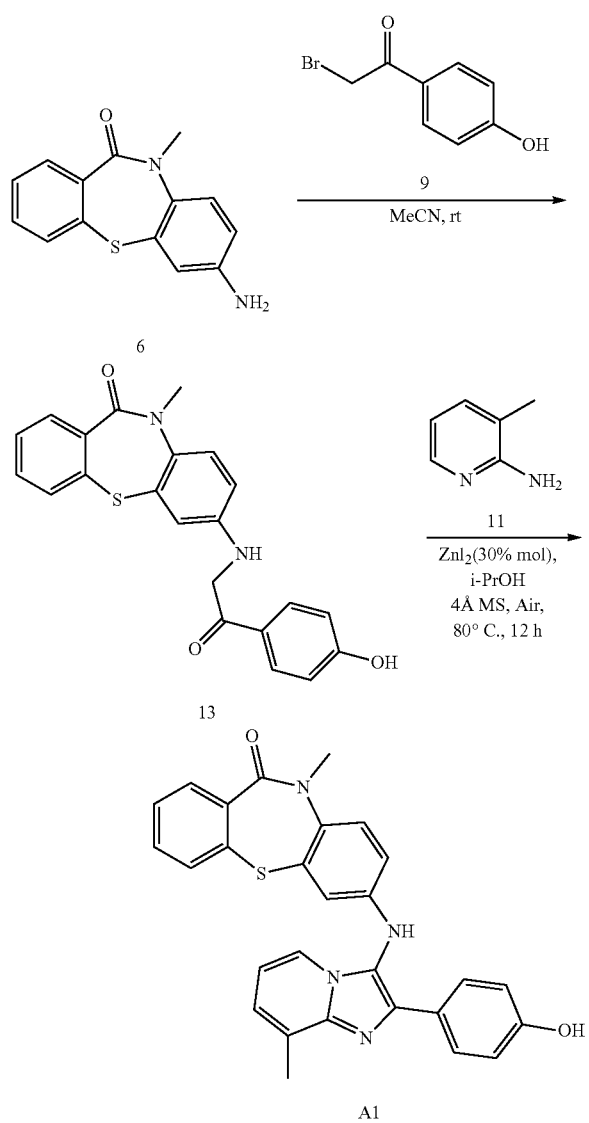

Example 4. Pharmaceutical Dosage Forms

The following formulations illustrate representative pharmaceutical dosage forms that may be used for the therapeutic or prophylactic administration of a compound of a formula described herein, a compound specifically disclosed herein, or a pharmaceutically acceptable salt or solvate thereof (hereinafter referred to as 'Compound X'):

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/mL) | mg/mL |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

| (vi) Aerosol | mg/can |
|---|---|
| 'Compound X' | 20 |
| Oleic acid | 10 |
| Trichloromonofluoromethane | 5,000 |
| Dichlorodifluoromethane | 10,000 |
| Dichlorotetrafluoroethane | 5,000 |

| (vii) Topical Gel 1 | wt. % |
|---|---|
| 'Compound X' | 5% |
| Carbomer 934 | 1.25% |
| Triethanolamine (pH adjustment to 5-7) | q.s. |
| Methyl paraben | 0.2% |
| Purified water | q.s. to 100 g |

| (viii) Topical Gel 2 | wt. % |
|---|---|
| 'Compound X' | 5% |
| Methylcellulose | 2% |

-continued

| (viii) Topical Gel 2 | wt. % |
|---|---|
| Methyl paraben | 0.2% |
| Propyl paraben | 0.02% |
| Purified water | q.s. to 100 g |

| (ix) Topical Ointment | wt. % |
|---|---|
| 'Compound X' | 5% |
| Propylene glycol | 1% |
| Anhydrous ointment base | 40% |
| Polysorbate 80 | 2% |
| Methyl paraben | 0.2% |
| Purified water | q.s. to 100 g |

| (x) Topical Cream 1 | wt. % |
|---|---|
| 'Compound X' | 5% |
| White bees wax | 10% |
| Liquid paraffin | 30% |
| Benzyl alcohol | 5% |
| Purified water | q.s. to 100 g |

| (xi) Topical Cream 2 | wt. % |
|---|---|
| 'Compound X' | 5% |
| Stearic acid | 10% |
| Glyceryl monostearate | 3% |
| Polyoxyethylene stearyl ether | 3% |
| Sorbitol | 5% |
| Isopropyl palmitate | 2% |
| Methyl Paraben | 0.2% |
| Purified water | q.s. to 100 g |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Compound X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

Additional Embodiments of the Invention

As described herein, the present application describes the atomic resolution crystal structures of *Saccharomyces cerevisiae* and *Candida albicans* Bdf1 BD1 and BD2 in their apo form (i.e. without a ligand) and *Candida albicans* Bdf1 BD1 and BD2 in complex with a selective inhibitor. These structures showcase the features of the pocket, and the interaction of a selective inhibitor with the pocket. Accordingly, these structures provide a method to identify novel small molecules and compositions that can be utilized as agents to treat pathogenic fungal infections. Examples of such fungi include, but are not limited to, *C. albicans* and *C. glabrata* (the latter for which *S. cerevisiae* is a good model organism). A similar approach can be applied to identify antifungal agents for other fungi containing Bdf1.

In one aspect, a method of identifying an antifungal compound is provided. The method includes: a) comparing three-dimensional field patterns of members of a small molecule library to a reference three-dimensional field pattern of an inhibitor of an essential fungal protein, wherein the reference three-dimensional field pattern is obtained from a crystal structure of the inhibitor complexed with an inhibitor-binding region of the essential fungal protein; b) identifying one or more putative antifungal compounds from the members of the small molecule library based on the three-dimensional field pattern comparisons; and c) testing one or more of the compound's antifungal activity to identify one or more antifungal compounds having antifungal activity, including compounds that selectively inhibit fungal versus human BET proteins, and compounds that selectively inhibit either BD1 or BD2 of a fungal BET protein, or both BD1 and BD2 of a fungal BET protein.

Alternatively, the method includes creating an in vitro binding assay, such as an homogeneous time-resolved fluorescence (HTRF) assay, for screening a chemical library using High Throughput Screening (HTS) techniques known to the state of the art, comprising a fungal protein essential for transcriptional regulation, or a functional subdomain thereof, and the natural peptide substrate for the fungal protein, with provision for detecting and quantifying specific inhibition by a known small molecule in said chemical library, and further provision for counter-screening to establish selectivity for the fungal protein relative to homologous human proteins or their corresponding functional subdomains. In some embodiments, the subdomain comprises one or more than one bromodomain.

In the method, the inhibitor binding region can be a bromodomain of fungal Bdf1 protein, and the antifungal compounds can have greater binding activity to fungal Bdf1 compared to the BET proteins of human or other animals.

In any of the methods, a putative antifungal compound, antifungal compound, or compound that inhibits a bromodomain of fungal Bdf1 protein, can be a compound of a formula of one of the embodiments below, a combination thereof, or a physiologically or pharmaceutically acceptable salt or prodrug thereof.

Further aspects of the invention include the following enumerated embodiments.

Embodiment 1

A method of identifying an antifungal compound, comprising:

comparing three-dimensional field patterns of members of a small molecule library to a reference three-dimensional field pattern of an inhibitor of an essential fungal protein, wherein the reference three-dimensional field pattern is obtained from a crystal structure of the inhibitor complexed with an inhibitor-binding region of the essential fungal protein;

identifying one or more putative antifungal compounds from the members of the small molecule library based on the three-dimensional field pattern comparisons; and testing one or more compound's antifungal activity to identify one or more compounds having antifungal activity;

or comprising:

creating an in vitro binding assay, such as an HTRF assay, for screening a chemical library using High Throughput Screening techniques known to the state of the art, comprising a fungal protein essential for transcriptional regulation, or a functional subdomain thereof, and the natural peptide substrate for the fungal protein, with provision for detecting and quantifying specific inhibition by a known small molecule in said chemical library, and further provision for counter-screening to establish selectivity for the fungal protein relative to homologous human proteins or their corresponding functional subdomains;

wherein the subdomain optionally comprises one or more than one bromodomain.

Embodiment 2

The method of embodiment 1, wherein the essential fungal protein is fungal Bromodomain factor 1 (Bdf1) and its inhibitor binding region is a bromodomain.

Embodiment 3

The method of any preceding embodiment, wherein the antifungal compounds have greater binding activity to fungal Bdf1 compared to Bromodomain and Extra-Terminal (BET) proteins of human or other animals.

Embodiment 4

A method of reducing or impairing the growth of a fungal culture, comprising exposing the culture to at least one compound that inhibits one or both bromodomains of fungal Bdf1 protein.

Embodiment 5

The method of embodiment 4, wherein the compound has greater binding activity to fungal Bdf1 compared to BET proteins of human or other animals.

Embodiment 6

A method of treating a fungal infection in a subject in need thereof, comprising administering to the subject at least one antifungal compound that inhibits one or both bromodomains of fungal Bdf1 protein.

Embodiment 7

The method of embodiment 6, wherein the compound has greater binding activity to fungal Bdf1 compared to BET proteins of human or other animals.

Embodiment 8

The method of embodiment 6, wherein the compound is effective against a *Candida* species that is resistant to other antifungal drugs.

Embodiment 9

The method of embodiment 6, wherein the compound is administered with another antifungal drug.

Embodiment 10

The method of any one of embodiments 4-9, wherein the at least one antifungal compound is provided as a pharmaceutical composition comprising a physiologically or pharmaceutically acceptable carrier.

Embodiment 11

The method of any one of the preceding embodiment, wherein the putative antifungal compound or antifungal compound of embodiments 1-3, or the at least one compound of embodiments 4-10, is any compound of the following formula (I), a combination thereof, or a physiologically or pharmaceutically acceptable salt or prodrug thereof:

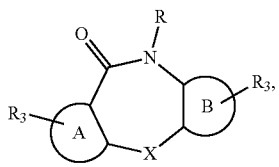

(I)

wherein:
X is C, O, N or S;
Ring A and Ring B are each independently a substituted or non-substituted aryl or a substituted or non-substituted heteroaryl;
R is —$(CH_2)_n$-L, wherein n is 0-4 and L is H, halogen, $R_1$, —COO—$R_1$, —CO—$R_1$, —CO—$N(R_1R_2)$, —$S(O)_2$—$R_1$, —$S(O)_2$—$N(R_1R_2)$, —$N(R_1R_2)$, —$N(R_2)COR_1$, a substituted or non-substituted aryl, or a substituted or non-substituted heteroaryl, wherein
$R_1$ and $R_2$ are each independently selected from the group consisting of:
(i) H, halogen, a substituted or non-substituted aryl or a substituted or non-substituted heteroaryl;
(ii) a substituted or non-substituted heterocycloalkyl; and
(iii) a C1-C8 alkyl, C2-C8 alkenyl or C2-C8 alkynyl, each comprising 0, 1, 2, or 3 heteroatoms selected from the group consisting of O, S, and N; or a substituted or non-substituted C3-C12 cycloalkyl or substituted or non-substituted C3-C12 cycloalkenyl;
each $R_3$ is independently selected from the group consisting of:
(i) H, a halogen, a substituted or non-substituted aryl, or a substituted or non-substituted heteroaryl;
(ii) a substituted or non-substituted heterocycloalkyl;
(iii) a C1-C8 alkyl, C2-C8 alkenyl or C2-C8 alkynyl, each comprising 0, 1, 2, or 3 heteroatoms selected from the group consisting of O, S, and N; or a substituted or non-substituted C3-C12 cycloalkyl or substituted or non-substituted C3-C12 cycloalkenyl; and
(iv) OH, or a substituted or non-substituted amine, ether, amide, or ester.

Embodiment 12

The method of any one of the preceding embodiments, wherein the putative antifungal compound or antifungal compound of embodiments 1-3, or the at least one compound of embodiments 4-10, is any compound of the following formulas (II) or (III), a combination thereof, or a physiologically or pharmaceutically acceptable salt or prodrug thereof:

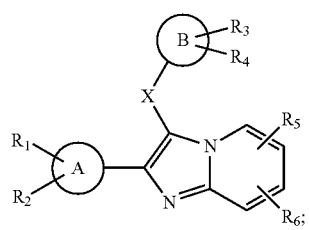

(II)

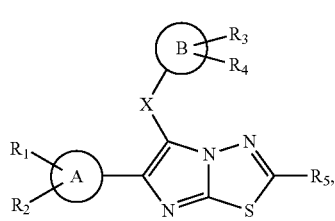

(III)

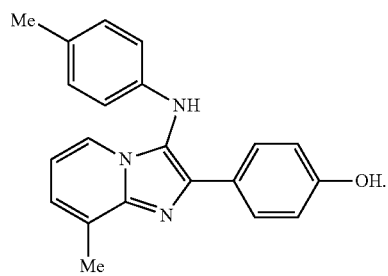

wherein:

X is NH, NHC(O), O or S;

Ring A and Ring B are each independently a substituted or non-substituted aryl or a substituted or non-substituted heteroaryl;

$R_1$, $R_2$, $R_3$ and $R_4$ are each independently H, Alk, OH, $NH_2$, NHAlk, OAlk, halogen, cycloalkyl, C(O)OH, C(O)OAlk, $C(O)NH_2$, C(O)NHAlk, $S(O)_2OH$, $S(O)_2NH_2$, or $S(O)_2NHAlk$, wherein Alk is a substituted or non-substituted $C_1$-$C_4$ alkyl;

$R_5$ is H, Alk, OH, $NH_2$, NHAlk, OAlk, halogen, cycloalkyl, C(O)OH, C(O)OAlk, $C(O)NH_2$, C(O)NHAlk, $S(O)_2OH$, $S(O)_2NH_2$, or $S(O)_2NHAlk$, wherein Alk is a substituted or non-substituted $C_1$-$C_4$ alkyl or $R^1$, where $R^1$ is piperidin-1-yl, morpholino or another nitrogen containing heterocyclic substituent; and $R_6$ is H, Alk, OH, $NH_2$, NHAlk, OAlk, halogen, cycloalkyl, C(O)OH, C(O)OAlk, $C(O)NH_2$, C(O)NHAlk, $S(O)_2OH$, $S(O)_2NH_2$, or $S(O)_2NHAlk$, wherein Alk is a substituted or non-substituted $C_1$-$C_4$ alkyl.

Embodiment 13

The method of embodiment 11 or 12, wherein the compound of the formulas (I)-(III) has greater binding activity to fungal Bdf1 compared to BET proteins of human or other animals.

Embodiment 14

The method of embodiment 11 or 12, wherein the compound of the formula (I) is N-(10-methyl-11-oxo-10,11-dihydrodibenzo[b,f][1,4]thiazepin-7-yl)tetrahydrofuran-2-carboxamide, and/or has the following structure:

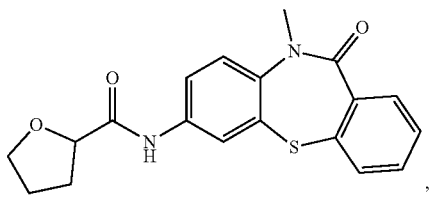 [SMILES: CN1C(=O)c2ccccc2Sc2cc(NC(=O)C3CCCO3)ccc21]

and the compound of the formula (II) is 4-(8-methyl-3-(p-tolylamino)imidazo[1,2-a]pyridin-2-yl)phenol, and/or has the following structure:

Embodiment 15

The method of embodiment 14, wherein the compound of the formula (I) is the R or S enantiomer thereof.

Embodiment 16

The method of embodiment 12, wherein the compound of the formula (III) is 1-methyl-N-(2-(piperidin-1-yl)-6-(p-tolyl)imidazo[2,1-b][1,3,4]thiadiazol-5-yl)-1H-pyrazole-5-carboxamide, and/or has the following structure:

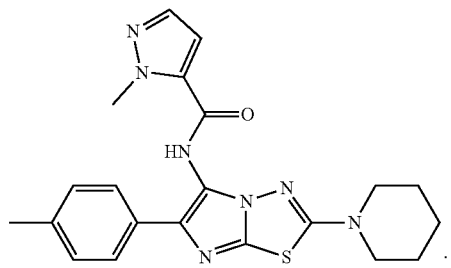 [SMILES: Cc1ccc(-c2nc3sc(N4CCCCC4)nn3c2NC(=O)c2ccnn2C)cc1]

Embodiment 17

The method of any preceding embodiment, wherein the putative antifungal compound or antifungal compound of embodiments 1-3, the at least one compound of embodiments 4-10, or the compound of the formulas a formula of one of the embodiments, is any compound or small molecule listed in FIG. 3, 6, 9, 11-13, 18, 21 or 22 of U.S. Provisional Patent Application No. 62/366,973, or the compound listed in embodiment 14 or 15, or a combination thereof, or a physiologically or pharmaceutically acceptable salt or prodrug thereof.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A compound selected from the group consisting of MS4 and MS5:

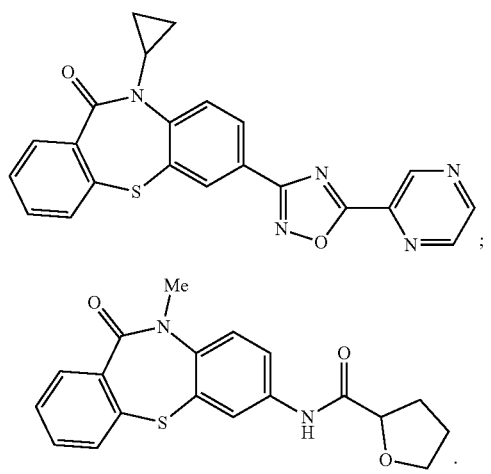

2. A pharmaceutical composition comprising a compound of claim 1, a second antifungal drug, and a pharmaceutically acceptable diluent, excipient, or carrier.

3. A pharmaceutical composition comprising a compound of claim 1 and an antifungal adjuvant.

4. The pharmaceutical composition of claim 3 wherein the antifungal adjuvant is an essential oil or an essential oil extract, wherein the essential oil or essential oil extract is selected from the group consisting of sweet orange, *Mentha arvensis*, peppermint, cedarwood, lemon, *Eucalyptus globulus, Litsea cubeba*, clove, spearmint, nutmeg, cinnamon, basil, bay leaf, and eugenol.

5. A method of treating a fungal infection in a subject in need thereof comprising administering to the subject an effective antifungal amount of a compound that inhibits one or both fungal bromodomain proteins, wherein the compound is a compound of claim 1 and the fungal infection is thereby treated.

6. The method of claim 5 wherein the compound is administered, concurrently or sequentially, in combination with a second antifungal drug.

7. The method of claim 6 wherein the second antifungal drug is amphotericin, anidulafungin, caspofungin, clotrimazole, fluconazole, flucytosine, itraconazole, ketoconazole, micafungin, miconazole, posaconazole, or voriconazole.

* * * * *